United States Patent [19]

Damjanovic

[11] Patent Number: 5,011,608
[45] Date of Patent: Apr. 30, 1991

[54] BIOGENIC AMINE ASSAY USING HPLC-ECD

[76] Inventor: Dragana Damjanovic, 10101 Saskatchewan Drive, Apt. 1601, Edmonton, Alberta, Canada, T6E 4R6

[21] Appl. No.: 273,449

[22] Filed: Nov. 18, 1988

[51] Int. Cl.$^5$ ............................................. B01D 15/08
[52] U.S. Cl. .................................. 210/656; 210/635; 210/198.2; 436/111; 436/161; 436/816; 436/901
[58] Field of Search ...................... 210/198.2, 635, 656; 436/106, 111, 112, 161, 816, 901; 73/61.1 C; 422/70

[56] References Cited

U.S. PATENT DOCUMENTS

| | | | |
|---|---|---|---|
| 4,313,828 | 2/1982 | Brownlee | 210/198.2 |
| 4,863,873 | 9/1989 | Matson | 204/153.1 |
| 4,908,322 | 3/1990 | Jacobson et al. | 436/112 |

OTHER PUBLICATIONS

"Ion Pair Chromatography of Organic Compounds", by Eksborg, Lagerström, Modin and Schill, Journal of Chromatography, vol. 83, pp. 99-110, (1973).

"Optimized Isocratic Conditions for Analysis of Catecholamines by High Performace Reversed-Phase Paired-Ion Chromatography with Amphoteric Detection", by Moyer and Jiang, Journal of Chromatography, vol. 153, pp. 365-372, (1978).

"Catecholamine Measurements in Plasma by High-Performance Liquid Chromatography with Electrochemical Detection" by Hjemdahl, Methods in Enzymology 142: 521-534, 1987.

"Practical Observations and Sources of Error in Assays of Plasma Catecholamines by 'High-Performance' Liquid Chromatography with Elecrochemical Detection" by Nyyssonen and Parviainen, Clinical Chemistry 33(10): 1938-1939, 1987.

"Instability of Calibration Curves of Liquid-Chromatographic Techniques with Electrochemical Detection: Role of the Detector" by Masse, Leclerc and Pouliot; Clinical Chemistry 34(3): 599, 1988.

"Review. Investigations of Catecholamine Metabolism Using High-Performance Liquid Chromatography, Analytical Methodology and Clinical Applications," by Krstulovic; Journal of Chromatography 229: 1-34, 1982.

"Effect of Pretreating Samples with Boric Acid Before Liquid-Chromatographic Determination of Urinary Catecholamines" by Degel, Zuman et al; Clinical Chemistry 33(1): 108-112, 1987.

"Simple and Fast Solvent Extraction System for Selective and Quantitative Isolation of Adrenaline, Noradrenaline and Dopamine from Plasma and Urine" by Smedes, Kraak and Poppe; Journal of Chromatography 231: 25-39, 1982.

"Editorial Review. Noradrenaline Release and Sympathetic Nervous System Activity" by Esler, Hasking et al; Journal of Hypertension 3: 117-129, 1985.

(List continued on next page.)

Primary Examiner—Richard V. Fisher
Assistant Examiner—Neil M. McCarthy
Attorney, Agent, or Firm—Burns, Doane, Swecker & Mathis

[57] ABSTRACT

A method for assaying compounds belonging to the group biogenic amines and including catecholamines, indoleamines, their metabolites and derivatives, and other small molecular weight compounds using a boric acid extraction method followed by high pressure liquid chromatographic separation in conjunction with electrochemical detection. The method utilizes high purity chemical and liquid components, a microparticulate-silica bonded phenyl stationary phase in the chromatography column and special cleaning and maintenance measures for the various components of the assaying apparatus which result in reduced baseline noise and allow the electrochemical cell to be operated at a sensitivity of one nanoamp or less full scale deflection on a continuous basis.

60 Claims, 8 Drawing Sheets

OTHER PUBLICATIONS

"Simultaneous Determination of Catecholamiens and Serotonin by Liquid Chromatography, After Treatment with Boric Acid Gell" by Imai, Ito et al.; Clinical Chemistry 34(3): 528–530, 1988.

"Liquid Chromatographic Measurement of Catecholamines and Metabolites in Plasma and Urine" by Foit, Kimura et al; Clinical Chemistry 33(12): 2209–2213, 1987.

"Radioenzymatic Assay of Catecholamines in Plasma After a Preliminary Solvent Extraction Compared with an Analoqous Liquid-Chromatographic Method" by Feoli, Bijault and Dehennin; Clinical Chemistry 34(2): 341–344, 1988.

"Determination of the Biogenic Amines and Their Major Metabolites in Single Human Brain Tissue Samples Using a Combined Extraction Procedure and High-Performance Liquid Chromatography with Electrochemical Detection" by Herregodts and Michotte; Journal of Chromatography 345: 33–42, 1985.

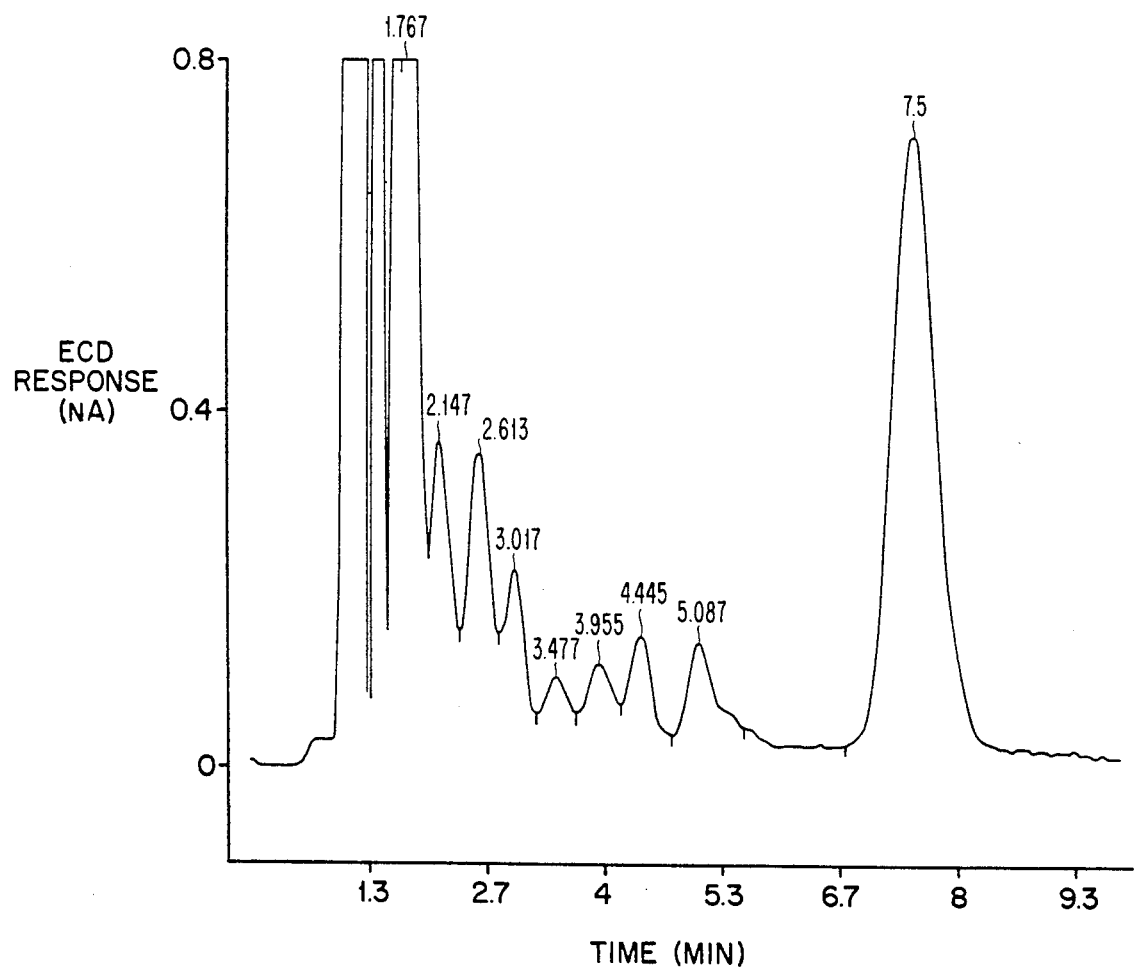

BIOGENIC AMINE ASSAY USING HPLC-ECD

BACKGROUND OF THE INVENTION

The present invention concerns a human plasma catecholamine assay which employs high pressure liquid chromatography with electrochemical detection (HPLC-ECD) after prior extraction of the catecholamines from plasma using the boric acid method of Smedes et al (J. Chromatogr. 231:25-39, 1982). The novel aspects of the method include the unique combination of equipment used in the assay, the chromatography conditions and the maintenance procedures developed to sustain the assay at a high level of sensitivity over a prolonged period of time.

Catecholamines are members of a family of molecules referred to as biogenic amines which include indoleamines, their metabolites and derivatives. In animals, catecholamines (CAs) act as neurotransmitters and hormones. Molecules possessing similar structures are also found in plants but their exact function in vivo has not yet been fully elucidated. CA-like derivatives of certain plants comprise clinically important drugs (e.g. ephedrine and reserpine). It is emphasized that the procedures described herein are equally effective on all biogenic amines derived from a multiplicity of sources (including physiological fluids other than plasma, tissue extracts and synthetic materials).

The molecules which can be detected by the assay techniques described herein include sympathomimetic amines such as amphetamines and their derivatives, indoleamines and their derivatives, the belladonna alkaloids and their derivatives, neuroleptic and non-neuroleptic analgesics, certain anesthetics, many antihistamines, anti-adrenergic drugs, xanthines, opioids (and their derivatives and antagonists), tricyclic antidepressants, tranquilizers, $\beta$-blockers, and so on. In short, many nervous system-active substances and other putative neurotransmitters are functional derivatives of the catecholamine nucleus and, as such, are amenable to the analysis procedures described herein.

The following discussion will focus on the study of catecholamines (CAs) in resting human plasma as the model system because this particular analysis presents the greatest analytical challenge. The methods described herein can also be used to detect the naturally occurring metabolites and derivatives of the principal CAs. Such metabolites are found concurrently in plasma and other physiological fluids; however, because these compounds are inherently more stable and present in higher concentrations than the plasma CAs, their analysis is considerably easier to perform and will not be discussed herein. The instability and low concentration of plasma CAs have made their analysis very difficult and the reliability and accuracy of methods developed previously have been the subject of controversy. The invention described herein has overcome the earlier problems encountered in the assay of plasma CAs.

1. Introduction

One entity responsible for the maintenance of vertebrate life is the central nervous system (CNS). The CNS communicates with the body of the organism by means of the peripheral nervous system. The CNS receives information regarding both sensation and organ function along afferent pathways and it sends instructions to the body on the efferent circuits.

Transmission of information is an electrochemical process: nerves propagate signals electrically along their own length. When these signals reach their target (be it another nerve cell or a target tissue) the nerve ending releases chemical signals which diffuse to the target and combine with it, thereafter eliciting responses from it. Compounds belonging to this special group of chemicals (which nerves use to relay information) are known as neurotransmitters. The electrical nerve signal itself is known as an action potential and has a duration of about one millisecond. Each action potential releases a quantum of neurotransmitter and information is coded by the frequency and pattern of the electrical impulses.

One part of the CNS, namely the autonomic nervous system (ANS), is primarily responsible for the day-to-day maintenance of a variety of critical, physiological functions and balances in the mammalian body. The ANS is a self-regulating system. It functions by means of a balance between two neural networks which can be viewed as an "accelerator" and a "brake". That is, instructions are sent via the two neural networks in an "ON-OFF" code with the end result being an integration of the signals received (most structures are innervated by both networks). Generally speaking, "OFF" instructions are sent down parasympathetic nerves (using the neurotransmitter, acetylcholine) and "ON" instructions are sent down sympathetic nerves (using the catecholamines). The designation "catecholamine" refers to a compound composed of a catechol nucleus (a benzene ring with two adjacent hydroxyl groups) and an amine-containing side chain. [The parent compound is $\beta$-phenylethylamine.] The most important CAs known to occur in humans are dopamine (DA), noradrenaline (NA) and adrenaline (A).

The parasympathetic nervous sytem is concerned with the functions of conservation and restoration of energy (i.e. vegetative aspects of day-to-day living) and is organized for discrete and localized action rather than mass response. It will slow down the heart rate (hence the "brake" analogy), lower the blood pressure, stimulate gastrointestinal movements and secretions, aid in absorption of nutrients, protect the retina from excess light and empty the urinary bladder and rectum.

The sympathetic side of the ANS is concerned with the expenditure of energy and the coordination of processes which allow the organism to deal with stress (hence the "accelerator" analogy). The most important neurotransmitter of this system is noradrenaline (or, "norepinephrine") and the network is often referred to as the adrenergic system. Among other effects, the sympathetic nervous system (SNS) accelerates the heart, raises the blood pressure, dilates the bronchioles, inhibits peristalsis of the intestines, causes the breakdown of glycogen into glucose and the liberation of free fatty acids (thereby supplying energy), and shifts blood to skeletal muscle. These actions may be significantly modified by the liberation of adrenaline (or "epinephrine") from the adrenal medulla into the blood stream. Hence, the "sympathoadrenal system" is organized in such a way so that the structures which it innervates can be orchestrated simultaneously and with great force. It is to be appreciated that, in mammals, an action potential can travel as fast as 120 meters/second along a nerve fibre whose diameter is, in turn, measured in angstroms. The nerve cell body ranges in length from 10-300 $\mu$m in vertebrates, to 300-800 $\mu$m in certain invertebrates, and the fibres which conduct the action potentials are no larger than 20 μm in diameter in vertebrates. The sympathoadrenal system is "on" all the time but the degree of activity varies from moment to moment and from organ to organ.

It will be obvious from the preceding discussion that NA and A are intimately involved in the day-to-day maintenance of normal vertebrate life. These two CAs are also thought to play a role in many pathological processes which disrupt the function of the structures and/or organs modulated by them. In the CNS, dopamine functions as a neurotransmitter but is of interest in the periphery mainly as a precursor of NA. Therefore, quantification of NA and A would, at least potentially, provide an intimate window into the state of an organism from a sympathetic nervous system point of view. As well, periodic monitoring of NA and A would yield a dynamic assessment of that state. Thus, the importance of the quantification of NA and A as a clinical and research tool cannot be overstated.

From an experimental point of view, there are a number of possible approaches to accomplishing the task of quantifying NA and A. The neurotransmitter outflow of sympathetic nerves spills over into the various physiological fluids (including blood plasma, urine and cerebrospinal fluid). The assaying of these fluids for their catecholamine content can provide information generally not available through other techniques. For example, while it is technically possible, to a limited extent, to study the sympathetic nerves to skin and skeletal muscle by microneurographic electrophysiological methods, the nervation of internal organs is not accessible for such testing. However, the variations in sympathetic neurotransmitter activity of internal organs may be assessed by biochemical means, namely by the measurement of the CA content of physiological fluids. Each of these fluids is in a constant state of flux and dynamic changes can be monitored within each one. By so doing, it should be possible to at least infer information regarding the level of nerve activity in the organ of interest and under the conditions of study. The monitoring of blood plasma levels of CAs offers the current best solution to assessing the state and activity of certain internal organs and systems from a sympathetic nervous system point of view. However, to provide meaningful data from assays of plasma CAs, it is necessary to balance the dichotomy of physiological dynamicism and methodological limitations.

Heretofore, severe limitations have been placed on the ability to quantify the concentrations of plasma catecholamines due in part to the ethereal quality of the catecholamines themselves. They are small compounds (less than 200 molecular weight) and are inherently unstable, having a half-life in plasma of only about two minutes. Furthermore, CAs are present in extremely minute quantities, viz., picograms per milliliter of plasma. For these and other reasons, methods for quantifying CAs have been slow in development.

The assessment of catecholamines in plasma is also constrained by the dynamic nature of the human nervous system. Some of the limitations imposed thereby are, first, that the assessment (in whatever form it might assume) cannot disrupt normal function or in any way alter it (i.e. affect the sympathoadrenal system, or "accelerator"); secondly, by implication, the technique must be as non-invasive as possible and be repeatable and reproducible; thirdly, it should be as realistic as possible in terms of having a minimum of special equipment and/or handling requirements.

The following summary of the life cycle of catecholamines is given in the interest of providing a background as to the significance and interpretation of the assay techniques described thereafter.

2. Synthesis and Release of Catecholamines

Catecholamines are produced and released into physiological fluids through the following mechanism. From a geographical point of view, nerves lie in very close proximity to blood vessels throughout the body. The amino acid tyrosine leaves the blood and enters the nerve fibre terminal varicosity by a special concentrating mechanism. Tyrosine is then converted in the cytoplasm to L-Dopa by the enzyme tyrosine hydroxylase (which is found only in CA-producing cells). This reaction proceeds very slowly in vivo and is considered to be the rate-limiting step in the biosynthesis of the CAs. Tyrosine hydroxylase is inhibited by CAs and this feedback inhibition appears to be important in controlling the rate of biosynthesis of NA in the sympathetic nerves. L-Dopa is, in turn, rapidly decarboxylated to dopamine by the enzyme dopa decarboxylase. The dopamine then enters minute, granulated vesicles (400–600 Å size) in the sympathetic nerve terminals where it is finally hydroxylated by dopamine-β-hydroxylase (DβH) to L-norepinephrine. DβH is found only in cells that produce NA. The NA remains protected and inactive inside these storage vesicles until liberated by a nerve impulse. The vesicles move to the surface of the cell membrane in response to an action potential and expel their contents into the synaptic cleft at the nerve ending in a process known as exocytosis. The neurotransmitter diffuses across the gap to combine with specific receptors on the post-synaptic membrane and thereby elicits responses in the post-synaptic target (or effector) cell.

The nature of the response varies according to the type of effector cell contacted: the cell could be a vascular smooth muscle cell, myocardial cell, adipocyte, myometrial cell, hepatocyte or another neuron. The extent of the physiological response of the target cell to secreted or injected CA will depend upon (1) the actual fraction of CA delivered to the target cell, (2) the ability of the cell to inactivate the delivered CA, and (3) the sensitivity (including receptor and post-receptor properties) of the target cell to the CA. This is how the "fine-tuning" and coordination of so many diverse cell types and structures is possible to effect simultaneously.

Inactivation of the CAs can occur by several different pathways. The primary one is re-uptake back into the same nerve varicosity which only moments before had released them. Once back inside the terminal, the CA molecules are re-stored in the vesicles and thus recycled. This is a highly specific, high-affinity and very rapid process called "Uptake 1" (or, Neuronal Uptake). Under normal conditions, this pathway predominates. When very high levels of CA are released—by, for example, continuing stimulation of the adrenal medulla or intravenous injection of CA—then a significant proportion will be removed by re-uptake into non-neuronal tissues such as muscle, connective tissue, liver and kidney. This is called "Uptake 2" (or, Extra-Neuronal Uptake) and in this case, the CA molecules are catabolized by enzymes. The two principal enzymes which digest the CAs are monoamine oxidase (MAO) and catechol-O-methyltransferase (COMT). The metabolic products formed include normetanephrine, metanephrine, VMA (3-methoxy-4-hydroxy-mandelic acid), MHPG (3-methoxy-4-hydroxyphenylglycol), DOPAC (3,4-dihydroxyphenylacetic acid), HVA (homovanillic acid), DOPET (3,4-dihydroxyphenylethanol), 5-HIAA (5-hydroxyindoleacetic acid), and DOPEG (3,4-dihydroxyphenylglycol). Some of these compounds can, in turn, be conjugated to their respective sulfates and glucuronides.

Primarily because of the efficiency of these uptake mechanisms, only a small fraction (perhaps 10-20%) of the physiologically active CA released by the terminals reaches the receptors on the target cells and activates them. Considering the sweeping powers of the CAs to turn cells on and off, it is appropriate that only small amounts of these compounds are needed to mediate their effects.

3. Significance of Plasma Catecholamine Studies

As was indicated earlier, nerves lie in close proximity to blood vessels; therefore, neurotransmitter spillover will rapidly appear in the blood stream. The same is true of extracellular and cerebrospinal fluids. In accordance with the preceding discussion on the metabolism of CAs, one would also expect to find CA metabolites from neuronal and non-neuronal tissue, in turn, spilled over into these fluids. Radiotracer studies have demonstrated that this is indeed the case.

Urine, on the other hand, is essentially an ultrafiltrate of plasma and is collected over a period of several hours. Compounds in urine depict activities taking place throughout the body, including the brain. For this reason, CA metabolites (as opposed to the parent molecules) predominate in the urine and thus represent an integrated image of many events which took place in the past. Metabolites are usually more stable than the parent molecule and this is especially true in the case of CAs. Additionally, CA metabolites in urine have time to accumulate to the nanogram per mL concentration range as opposed to plasma CA levels which are in the picogram per mL range.

The choice of which physiological fluid to sample for CAs is based on the kind of information about the body that is required. If one is attempting to obtain an answer to a question regarding the function of the CNS then analysis of cerebrospinal fluid is preferred. However, the routine periodic sampling of cerebrospinal fluid (CSF) is neither ethical nor practical; therefore, this is not a solution that can be applied to the problem of the state of the SNS except under special circumstances (e.g., during neurosurgery).

If, on the other hand, one is only interested in global trends in the adrenergic system (such as the secretion of CAs during the night as an indication of an active pheochromocytoma), then urinalysis can provide an adequate assessment.

If an immediate answer as to the state of the adrenergic nervous system is required (such as prior to, and following, surgery or after a myocardial infarction), then clearly a sample of plasma should be assayed. Most often, a plasma assessment is preferred because of the dynamic nature of the SNS. In both research and clinical situations, one is trying to gain information about a system that is highly influenced by the state of the organism at that point in time and in that particular state of health. Under the background of a constantly shifting scale, it is more physiologically relevent to catch this dynamicism at the time, and under the conditions, it takes place rather than attempting to infer information about events past at an unspecified location.

However, it must be emphasized that only a very small amount of CA diffuses away from the synaptic cleft and into the circulation. The actual amount of CA escaping from any one organ or structure will be the integrated result of a number of contributing factors. These include the sympathetic nerve firing rate, the density of the sympathetic nerves in that organ or area, the mass of the organ, the width of the synaptic cleft, the capacity of neuronal and non-neuronal tissue for re-uptake and/or enzymatic degradation, the permeability of the local capillaries to the CAs, and the blood flow through the organ. Obviously, these parameters will also vary tremendously between organs and according to need over time. It is known that the half-life of NA in plasma is approximately 2 minutes; therefore, if it is desired to know what is happening within a structure (from a sympathetic nervous system point of view), blood should be sampled periodically over some unit of time (e.g., every six minutes for an hour).

It is important to realize that the CAs which escape into the bloodstream (and other physiological fluids) are not at liberty to float freely: most are in fact conjugated to sulfate molecules. Only a small proportion of the total amount of any CA (perhaps 10 to 20%) exists in plasma in the free, i.e., unbound, non-derivatized form. [In the case of dopamine, this proportion is even lower (i.e. 5%).] It is this free amount of CA that is of interest in clinical and research medicine. The exact function of the sulfoconjugated CAs is not known and the mechanisms of the equilibria which create and maintain this pool remain to be elucidated. It has, however, been demonstrated that it is the amount of free CAs which fluctuates in response to stimuli; therefore, measurement of this fraction constitutes a valid appraisal of CA dynamics.

Having established that one wishes to know the CA content of plasma, the problem remains of the choice of location(s) for such a sample. Logically, it would have to be from the venous outflow of the organ (or system) being studied. This requires that the assumption be made that no NA came into the organ (on the inlet, or arterial side) and that the organ did not extract any NA that may have been present there. These may or may not be safe assumptions. In any event, selective catheterization of individual organs is not practical. What is practical is a venous blood sample from a peripheral vein. Because many organs are necessarily spilling excess CAs into the blood from a wide range of physiological tasks, it would seem that such a blood sample would not provide any useful information. Fortunately, it does. The venous blood levels of NA and A do parallel the known level of sympathetic tone in a number of clinical and experimental situations [Ref.: Esler, Hasking et al, J. Hypertension 3:117-129, 1985.]. Even though what is being sampled is some net result of events occurring throughout the body (including the brain) the blood levels of NA and A do fluctuate in a coherent fashion. For example, at rest, the normal plasma level (blood being part cells and part fluid, i.e., plasma) of NA is about 150-300 pg/mL (picograms per milliliter) and A is about 25-75 pg/mL. However, during exercise, these values can climb to 5,000 pg/mL NA and 1,500 pg/mL A.

Occasionally, it has been reported that a patient with a tumor of the adrenal medulla, known as a pheochromocytoma, will have plasma levels of NA of 10,000 pg/mL and A of 4,000 pg/mL. This latter amount of epinephrine is essentially lethal, as is the tumor if allowed to grow unchecked. Since these changes from resting values are at the level of orders of magnitude, they would not often be confused with normal physiological concentrations of CAs. Therefore, it is safe to conclude that in most settings by measuring plasma levels of CAs in peripheral blood, a useful index of SNS activity is obtained. Only under special circumstances is it possible to study regional sympathetic response patterns, as represented by CA overflow, through sampling of blood from selected vessels.

It should be borne in mind that epinephrine is mainly synthesized as a hormone in the adrenal medulla. Therefore, any increase in the concentration of epinephrine in plasma will indicate increased adreno-medullary secretion. Norepinephrine, on the other hand, is primarily a neurotransmitter released by post-ganglionic sympathetic nerve endings. At low nerve impulse rates, about 90% of the norepinephrine released by the nerve terminal is removed by re-uptake (Uptake 1) back into the same nerve terminal. It is only at high nerve impulse rates (or inadequacy of the re-uptake system) that higher amounts of norepinephrine can escape into the bloodstream. It follows that this is the explanation for the low, resting concentrations of norepinephrine and epinephrine that are normally encountered. Thus plasma CA measurements will be a more reliable index, or accurate indicator, of adrenergic activity when the adrenergic stimulus is more intense.

The measurement of plasma levels of CAs is always accompanied by the simultaneous collection of other physiological data such as heart rate, blood pressure, oxygen consumption and the like. Taken in isolation, CA concentrations are usually relatively meaningless. Furthermore, it is vital that in any study of sympathetic nervous system function, individual subjects act as their own controls because CA responses are so individually tailored to the needs of a single organism.

The exact factors responsible for the maintenance of the dynamic equilibrium of CA levels in plasma, their mechanisms of action and the magnitude of their effects on plasma CA levels is a separate issue from the fact that CAs appear in plasma at all. It is precisely because of the methodological limitations which have heretofore existed in this field that the amount of actual (as opposed to apparent) information on CA dynamics is scant. Controversies persist because definitive studies cannot be performed without standardized analytical techniques which are available to laboratories in many centres with different research foci. [Ref.: Hjemdahl, Acta Physiol. Scand. Suppl., 527: 43-54, 1984.] For these reasons, the full characterization of CA metabolism and function remains to be performed.

Finally, it must be borne in mind that the assay, as described herein, will refer only to analysis of plasma samples obtained from subjects who are drug-free. That is, they have not taken drugs (defined as any foreign substances) which would either interfere with the functioning of the body in vivo (i.e. the synthesis, release and metabolism of the CAs) or with the performance of the assay (e.g., the separation of the peaks of interest on the chromatogram).

4. Summary of Catecholamine Assay Techniques

The discussion hereinafter will be concerned with the elucidation of the levels of CAs found in human plasma samples. This model (i.e., human plasma CAs) is used because this particular analysis presents the greatest analytical challenge. It is stressed that structurally similar compounds, their derivatives and metabolites, obtained from other sources, can also be assayed utilizing the methods described herein but such compounds and their assay will not be described.

Each one of the catecholamines (i.e., A, NA and DA) has different physiological and physicochemical properties. This latter characteristic has been exploited to develop assay techniques. Historically, these assays have proven to be a challenge both from the point of view of the compounds being tested and from the point of view of the technology available.

As mentioned above, catecholamines are small molecules (less than 200 molecular weight) with very subtle structural differences; they are normally present in very low quantities in plasma (picograms of the native CAs in plasma versus nanograms of stable metabolites in urine or nanograms of CAs in tissue) and have a very short half-life (less than two minutes) in plasma. Furthermore, CAs are unstable molecules which decompose in alkaline solutions, upon exposure to light, and even if brought to temperatures greater than $+5°$ C. Obviously, before plasma CAs can be measured, they must first be stabilized, separated from the other constituents of plasma and from each other, and finally, they must be "visualized" in some quantifiable fashion. Whatever methodology is chosen to achieve this end must also be reproducible and reliable.

Stabilization of the CAs in a blood sample is most easily achieved by collecting the blood into a chilled, silicone-lined tube; the blood sample should be placed on ice and in the dark as soon as it has been collected. It is important that the plasma be separated from the cellular fraction of blood as soon as feasible because red blood cells contain catabolic enzymes such as catechol-o-methyltransferase. Depending on the assay technique to be used, (a) chemical stabilizer(s) may be added to the plasma. If it cannot be assayed immediately, the plasma sample must be frozen at $-70°$ C. or lower.

Having stabilized the plasma, the CAs must then be separated away from the other constituents of the plasma. Blood plasma is a complex matrix comprising thousands of molecules of many different chemical types, molecular sizes and structures. In the case of the unstable CA molecules, it is essential that the extraction and quantification processes be as brief and as accurate as possible. A plethora of methods have been tried in an attempt to divorce the CAs away from the other constituents of plasma or else to quantify them, in situ. as expeditiously as is practical. These methods have achieved varying degrees of success and will be reviewed hereinbelow in terms of the availability of new technologies so as to put the present invention in context with this field of analysis.

Prior to the mid-1950's, the only way to find out whether or not plasma contained any CAs was to use a bioassay. In these techniques, crude extracts of plasma were injected into a small mammal (e.g., a rabbit) and heart rate was monitored. While these tests were sensitive, they gave little specific information regarding the actual amount or type of CA present. Furthermore, reproducibility depended entirely on the skill of the operator and was not transferable.

Since the 1950's, there have been three major revolutions in available technology and all have resulted in improved CA assays. These methods represent attempts to improve the specificity and sensitivity of CA measurements while reducing the amount of interference by other compounds. They are:

(A) Development of the fluorometric assay (mid-1950's to mid-1960's);

(B) Development of the radioenzymatic assay (mid 1960's to mid-1970's);

(C) Development of an assay utilizing high pressure liquid chromatography with electrochemical detection (HPLC-ECD) (late 1970's to present).

Other methods of separation and detection of CAs have been tried, including Gas Chromatography-Mass Spectrometry (GCMS), radioimmunoassays and a variety of techniques employing detection of the CAs by electron-capture detectors, ultraviolet absorption and fluorescent spectroscopy but none of these has, to date, proven to be of practical value. [Ref.: Holly and Makin, Anal. Biochem. 128(2):257-274, 1983.]

The use of monoclonal antibodies for the isolation of CAs from plasma has so far been unsuccessful due to the lack of specificity of the antibodies produced. Recently, the CA receptor was successfully cloned and it is hoped that this product will eventually be made available for CA assays. However, any resulting specific assay technique(s) remain(s) to be developed. Therefore, the three assay methods in the above list represent the practical advances, to date, for the quantification of CAs.

To put the significance of the present invention (an HPLC-ECD plasma CA assay) into perspective, the following is a short review of the fluorometric and radioenzymatic assay methods.

(A) Fluorometric Assay

The fluorometric assay is based on the fact that CA molecules possess natural fluorescence. The CAs and their metabolites have characteristic emission spectra which can be exploited, to some extent, to differentiate between them. The idea behind an assay based on this fact was to be able to detect levels of CAs in physiological samples with a minimum of pretreatment (i.e. isolation from plasma). Normally, the plasma was only deproteinized prior to analysis. However, not only is the native fluorescence of the CAs very weak and non-specific, but these molecules are present in such low concentrations in plasma that they can barely be detected by available instruments. This limitation can be overcome by the derivatization of the CAs to larger molecules which have strong native fluorescence (for example, trihydroxyindoles and o-phthalaldehyde have been used) thereby rendering the CAs more visible and facilitating their detection.

One of the major advantages of this method is that it is quick to perform and comprises relatively few steps; additionally, the equipment required is inexpensive and readily available. Among the major disadvantages of this type of assay is the complication that plasma contains many compounds (other than those of interest) and some of these are susceptible to the isolation and concentration procedures employed. Such compounds may also fluoresce, thereby invalidating the assay. Many common foods, such as bananas, chocolate and coffee, and frequently prescribed drugs, such as antibiotics, fall into this category.

Furthermore, even with derivatization, the concentrations of CAs in resting plasma are so low as to be undetectable. An additional problem with the derivatization is that the molecules thus created are very unstable and must be constructed and quantified under strictly controlled conditions or else they will, literally, disappear from the detection system. It is also not possible to differentiate between the CAs (DA, NA, A); therefore, the assay can only quantitate the total amount of CAs present rather than characterize their individual concentrations. In time, the assistance of alumina extraction, isotope-labelling and chromatographic separation were added to the fluorometric procedure but neither the specificity nor the sensitivity of this assay method could be significantly improved without heroic efforts. All of these restrictions also have implications for the reproducibility of the method, which is limited. These limitations have precluded the utility of this method to measurements of plasma CA levels. Therefore, this assay is largely reserved for the analysis of urine samples which contain nanogram quantities of CA metabolites (i.e. $1 \times 10^{-9}$ grams of stable metabolites).

Hospital laboratories often maintain a fluorometric assay for total urinary CAs to use as a screen for the above-mentioned type of life-threatening tumor of the adrenal medulla (pheochromocytoma). This tumor secretes extremely high levels of CAs thereby facilitating the diagnosis. In this instance, information regarding urinary levels of CA metabolites can be very useful.

The recent introduction of laser technology to the field of fluorescence detection is expected to improve the sensitivity of this assay method (see below). However, the problems of the stability of the analate, specificity, sensitivity, and reproducibility of the fluorometric assay must still be overcome.

(B) Radioenzymatic Assay (REA) of Plasma Catecholamines

Clearly, the fluorometric assay does not constitute a resolution of the problems of effectively extracting, separating and detecting the individual CAs of human plasma. The next major attempt at solving these problems entailed the enzymatic conversion of the CAs to their more stable metabolites. It could be arranged that the metabolites thus formed were radiolabelled thereby simplifying quantification once the molecules had been separated from the plasma and from each other. This separation was effected by the use of chromatography. Until the advent of HPLC-ECD technology, the radioenzymatic assay method was the most useful means by which to quantify plasma CAs. It is instructive to subsequent discussions herein to clarify the basic principles of chromatography before the details of this assay are reviewed. (Both the radioenzymatic and HPLC-ECD catecholamine assays utilize chromatography.)

SUMMARY OF THE PRINCIPLES OF CHROMATOGRAPHY

Chromatography is a technique whereby the constituents of a mixture can be separated from each other by the exploitation of subtle differences between their physicochemical properties even if the molecules are very similar to one another. A chromatographic system is composed of at least two main parts: a mobile phase and a stationary phase. Typically, the mobile phase (MP) is a gas or a liquid that is carrying the mixture to be separated over an immobile surface, the stationary phase (SP). The components of the mixture exhibit differential degrees of interaction with the SP: some of them are attracted to the SP and retained by it while other analates are not, and continue to flow through the system at essentially the same velocity as the MP. It is exactly this differential interaction at the mobile-stationary-phase interface that effects the separation of even closely related compounds. This interplay can be controlled by manipulation of the physicochemical properties of the mobile and stationary phases and thereby affect the rates at which particular substances introduced into the chromatographic system will pass through it and will be separated from one another. It is worth noting that the actual properties which control the interaction(s) between the MP and SP include absorption and adsorption, solubility, molecular shape and size, ionic charge and specific binding affinity. In this way, subtle separations become possible and a wide variety of applications becomes feasible.

Chromatographic techniques can be classified in one of two ways: either on the basis of the interactions taking place (e.g., partition chromatography, steric exclusion chromatography, etc.) or on the basis of the physical state of the mobile and stationary phases (e.g., gas-liquid, liquid-liquid, liquid-solid, etc., chromatography). This latter method is more common and has, in fact, been further simplified to designate only the type of stationary phase employed. For example, in the case of types of liquid chromatography (LC): a mixture of components is separated into its constituent compounds by flowing a liquid MP over a solid SP. The SP could be either paper, or a coated glass or plastic plate, or a tube ("column") packed, for example, with a bonded silica material, the latter configuration effectively constitutes an immobilized liquid. The name of the chromatography would be paper, thin layer and column liquid chromatography, respectively. Due to recent advances in the technology of columns, this last field has expanded so much that methods are now referred to by the type of column employed (e.g., reverse phase or ion exchange chromatography).

The radioenzymatic assay (REA) that is often employed for human plasma CA measurements uses thin layer chromatography (TLC), a type of liquid-solid chromatography. In TLC, silica gel (or some other adsorbent) is spread as a thin layer (e.g., 0.25 mm) over a glass or plastic plate (typically 20×20 cm size). Pre-coated plates with a variety of adsorbents are available commercially. The plates (SP) are usually scored along the vertical axis to create individual channels that do not overlap with each other. The mixture to be separated is spotted or streaked onto a channel near the bottom edge of the plate and allowed to dry. The plate is then placed inside a closed glass tank which has a 1 cm deep layer of liquid MP (specially formulated for the separation to be effected) lying at the bottom of it. The MP migrates up the plate by capillary flow.

Each of the components within the sample will have a different degree of interaction with the silica/alumina particles (either associating with the particles and being detained by them or else being unattracted to them and passing them by). Riding on the flowstream of the MP, the sample thus becomes separated into zones of compounds. These migrating zones of individual components of the sample mixture are known as bands. The migration of a band through the column is known as the elution of a compound.

The separation of the compounds of the mixture is stopped by taking the plate out of the tank at the predetermined time. The MP is allowed to evaporate from the plate and the compounds of interest are now separated from each other in individual bands which can either be visualized with the aid of dyes or ultraviolet light or be detected by radioactivity or chemical reactivity. The distance of a band from the origin of the plate is characteristic for each compound and is the basis for its identification. If further purification or quantification is desired, the silica gel can be scraped off the plate (in individual bands), the compounds can be lifted from the silica and subjected to further reactions.

A detailed description of another type of chromatography (paired-ion partition chromatography) is included below along with the discussion on the components of the HPLC system.

It is important to appreciate that chromatographic systems can only separate finite numbers of molecules out of a mixture before they become overloaded. Therefore, chromatography is usually used after some selective, pre-purification of the sample of interest has been performed. Biological matrices are particularly complex and if not adequately pre-treated, can reduce the efficacy of a chromatographic system and/or altogether destroy the system. It is the goal of clinical chemistry to create a "black box" which will accept an untreated physiological sample at one end and which will release a selective analysis of any desired compound in that sample at the other end of the machine. Until such time as this dream becomes a reality, intermediary steps between the source of the sample and the analysis of any particular compounds contained therein will be necessary.

The REA represented a significant improvement over the fluorometric method because of its use of isotopes to create stable metabolites which could then be extracted from plasma without fear of losing a labile derivative; these metabolites could then be isolated from each other by the use of chromatography, and, finally, quantified in a reproducible fashion. The metabolites were a secure representation of the concentration of the native CAs in the sample and a high level of sensitivity could be achieved by the method.

More specifically, the CAs are converted to their more stable metabolites by the action of their natural enzyme, catechol-O-methyltransferase (COMT). The metabolites are rendered visible by the use of $^3$H-S-Adenosyl-L-Methionine, or $^3$H-SAM, as the (radioactive) methyl group donor which is supplied to the enzyme reaction. The radio-labelled metabolites are then extracted from plasma using organic solvents and separated by TLC. Each band on a plate contains one of the CAs, now stabilized and radioactively "tagged"; these can be scraped off and subjected to further reactions, as necessary. If desired, the DA can be directly quantified from the radioactivity found in its band by putting the band (silica and all) into liquid scintillation counting fluid and counting the emulsion. $^3$H-Normetanephrine and $^3$H-metanephrine are normally further purified by conversion to $^3$H-vanillin by reaction with periodate. The radioactivity of the vanillin is measured and calculations are performed to give the concentration of the original compounds in the plasma. [Ref: Newsholme and Taylor, Biochim. Biophys. Acta 158:11-24, 1968 for the principle underlying this method; and as examples of assays: Peuler and Johnson, Life Sci. 21:625-636, 1977; and Hörtnagl, Benedict et al, Br. J. Clin. Pharmacol. 4:553-558, 1977.].

The pharmaceutical firm, Upjohn, has patented a radioenzymatic CA assay and commercialized it in kit form. See U.S. Pat. Nos. 4,288,542; 4,287,368; 4,284,587; 4,242,456; and, 4,242,222.

The major advantages of the radioenzymatic method are that it requires less than one milliliter of plasma to perform the assay (in duplicate), and that the low resting levels of CAs in human plasma can be detected.

The disadvantages of the radioenzymatic method are numerous. For one thing, until recently, the COMT used in the first part of the assay had to be isolated in the researcher's own laboratory. The isolation technique is lengthy and laborious, with no guarantee of success. It is also unpredictable, giving limited control over yield and activity of the enzyme. Furthermore, the assay itself has many complicated steps, requires many pieces of equipment and may take as long as two and a half days to complete. Lastly, the procedure demands a high degree of technical skill on the part of the operator. Predictably, the assay is also expensive to maintain.

Even if all of the above factors could be controlled, the radioenzymatic assay has two weak points that lie outside of the control of the operator: the quality of the $^3$H-SAM is critical to the success of the assay [Ref.: Mason and Weinkove, Clinica Chimica Acta 136:1-11, 1984; Oldham, Int. J. Appl. Rad. Isot. 21(7):421-429, 1970], as are the TLC plates. Unfortunately, these are both commercial items and thus subject to the vagaries of commercial quality-control. Over a longer period of time, it often happens that things go wrong at the manufacturing level (particularly with the $^3$H-SAM, a very unstable product) and a laboratory can be shut down for months, with no solution in sight. This has proven unacceptable to individuals and institutions which would otherwise use the assay on a regular basis. Therefore, the REA does not present a practical solution to the problem of measurement of plasma CA levels.

(C) Summary of High Pressure Liquid Chromatography (HPLC) Equipment

The appearance of new, HPLC-ECD technology in the late 1970's allowed circumvention of some of the above problems and CA assays utilizing the new techniques were developed concurrently with the release of the new technology. HPLC offers the possibility of rapid analysis of samples and yields excellent resolution of compounds and precise quantification in a reliable and reproducible system. Additionally, HPLC does not require the compounds of interest to be derivatized prior to analysis. Unfortunately, the technology of sensitive detectors has not kept pace with the development of HPLC systems and there is still no universal detector available which can take full advantage of the separative capabilities of these columns.

To clarify subsequent discussions on the specific aspects of CA assays using HPLC-ECD (ECD, Electrochemical Detection) technology, a generic summary of the method and materials it utilizes will be presented.

In traditional liquid chromatography, a hollow glass or metal tube is filled ("packed") with a slurry (the SP). The mixture to be separated, dissolved in a MP, is layered on top of the slurry (or, chromatographic bed) and flows through it by the force of gravity and the pressure of the solvent reservoir above it. Dimensions of such columns and the nature of the components of their SP are highly variable. While this type of chromatography is a powerful separation technique, it is also very slow (requiring up to 6 hours to complete a single "run") and is not readily amenable to automation. It was discovered that separations could not only be accelerated but also improved if the size of the particles that made up the chromatographic bed was reduced from $>100$ $\mu$m to 5-40 $\mu$m; and thereby significantly increasing the amount of surface area available for the chromatography. The smaller particle sizes also entailed a five- to ten-fold reduction in the diameter of the columns (typical dimensions : 30 cm$\times$4.0 mm, L.$\times$I.D.) thereby imposing a need for special pumps to drive the MP through the matrix of the SP (which had now acquired a considerable resistance to flow). A new generation of high pressure pumps was developed to deal with these mechanical challenges. These pumps have gone on to lend their name to a new type of chromatography: high pressure (or, high performance) liquid chromatography, or HPLC.

HPLC systems are of particular interest to biomedical analyses because they permit the simultaneous separation and quantification of trace amounts of physiologically significant compounds.

Normally, there are at least six components to the HPLC system:
(a) Solvent (mobile phase) reservoir(s)
(b) Pump
(c) Injector (i.e. a means by which to introduce the sample to be analyzed into the system)
(d) Column (containing the stationary phase)
(e) Detector
(f) Data recorder(s)
Each of these components will be described in turn.

SOLVENT (MOBILE PHASE) RESERVOIR(S)

The solvent reservoir contains the special mobile phase which has been selected for optimal separation of the compounds of interest. The composition of the mobile phase will also be determined by the choice of column which, in turn, is determined by the physicochemical properties of the compounds to be isolated from one another, and by the choice of detectors. The most commonly used detectors are ultraviolet absorption and electrochemical.

Because of the scale at which the HPLC-ECD apparatus operates, it is extraordinarily sensitive to dissolved gases and particulate matter. The flowpath of the mobile phase (MP) is equipped with a variety of microscopic filters designed to protect the column and detector farther downstream. Special attention must be also be paid to the quality of the constituents of the MP so that contaminants are not inadvertantly introduced into the system. This restriction applies to all chemicals, solvents and water used to create the MP. For reasons discussed more fully hereinafter in connection with the detailed description of the invention, it is important that the chemicals which comprise the mobile phase be of the highest purity available. If the MP is aqueous-based, the water must also be ultrahigh purity: namely, Type I Reagent Grade Water with a preferred resistivity of at least 18 M$\Omega$. Before it enters the HPLC system, the mobile phase must be membrane-filtered and degassed (i.e., have all dissolved air removed), and it must be maintained particle- and gas-free during use.

HPLC systems can be equipped with a differential array of mobile phases, specifically programmed by an electronic control unit and designed to elute a range of compounds from a single column or even a series of columns.

PUMP

The pump must be able to deliver constant, reproducible, pulseless flow of mobile phase (pulled from a reservoir) through the entire HPLC-ECD system. Therefore, the usual practice is to have a double, reciprocating pump (that is, with two pump heads) and to install one or more pulse dampeners. The dependability of the unit itself is usually determined by its manufacturer and there are many good machines to choose from today.

It will be appreciated that these pumps are highly miniaturized for the purpose of pumping fluids of variable viscosities through very narrow bore stainless steel tubing capable of withstanding pressures as high as 6000 psi. Typically, the outer diameter of this tubing is 1.6 mm and the inner diameter is either 0.51 mm (considered a "large" tube) or 0.23 mm (considered a "normal" size tube). Furthermore, all materials inside the pump which come in contact with the mobile phase must be completely inert, and are usually made from special steel alloys, teflon or PTFE. The valves and pistons present a special challenge: not only must they be chemically inert but they must also be able to withstand the rigors of sustained function at that scale. The valve parts (for example, the ball and seat) are made of synthetic ruby and sapphire, respectively, and the piston rod is sapphire.

These pumps can now be microchip-controlled and have become much more dependable than was possible in the past. However, they do require special handling and maintenance. For example, because the system is closed and is running at high pressure, it must be maintained free of leaks; leaks disrupt flow and are manifested as baseline noise (defined hereinbelow). Therefore, the compression fittings in the system must fit snugly and be properly aligned. This can be ensured by the use of tubing which has perpendicularly cut edges and the proper positioning of ferules on the tubing.

A other important source of difficulty with this equipment is air: Any air bubbles formed within the pump would both disrupt laminar flow and partially block the fine tubing and microscopic filters of the pump by creating eddy currents around the gas bubble. Similarly, any particles which came through the system would quickly clog tight junctions and corners and, again, disrupt flow or stop it altogether, causing damage to the pump itself or other components (of the system) farther downstream. It is for this reason that these pumps have a myriad of special filters throughout the flowpath of the mobile phase; these filters are designed to trap particles and/or tiny air bubbles which have accumulated. This problem (i.e., MP quality) alone is a serious issue in the maintenance of dependable, long-term function of these pumps.

INJECTOR

The injector is the component which gives the operator access to the column, and thus must be able to deliver the entire sample (i.e., the mixture of compounds to be separated) to the column without losses of sample or addition of air. Again, as with the pumps, the technology that makes up these units has improved dramatically in recent years and injectors have become quite dependable. The improved technology is directly responsible for making this the simplest part of the HPLC system to maintain.

COLUMN (CONTAINING STATIONARY PHASE)

The sample mixture to be analyzed is introduced by the injector into the flowstream of the MP to be separated into its constituents by the column, preferably as completely as possible. Therefore, the column will be the final determinant of the success and extent of separation of the compounds in the mixture to be analyzed. In an effort to protect the column, a pre-column (called a guard-column, or guard-filter) is often placed before the main column as a precaution against extraneous materials (e.g., proteins) causing stripping of the packing material and/or loss of resolution.

A variety of materials are available as column packings including silica, alumina, charcoal and organic polymers, but silica is the most versatile and the most widely utilized. Silica packings are available in three main types of particles: (a) macroparticulate—particles are generally spherical, completely porous and $>40$ $\mu$m in size; (b) microparticulate—particles are spherical or irregularly shaped, completely porous and 3–10 $\mu$m in size; (c) pellicular—in this case, glass beads, 20–60 $\mu$m size, are coated with a porous layer of silica.

Columns made of the microparticulate silica material offer the greatest flexibility, have the highest chromatographic efficiencies (i.e., attainment of adequate resolution of mixtures thereby giving the observed well-defined narrow peaks described below) and the greatest loading capacities (the smaller the particle size, the greater the theoretical plate count.) Furthermore, an analysis can be completed within a short period of time (generally less than 30 minutes and often less than ten). This latter characteristic simplifies the development of optimal separation conditions for a given separation and permits rapid analysis or diagnosis of problems.

Having been introduced by the injector into the flowstream of the MP, the sample mixture is separated into its components/constituents on the column. Each of the components within the sample will have a different degree of interaction with the column (either associating with the particles and being detained by them or else being unattracted to them and passing them by). Riding on the flowstream of the MP, the sample thus becomes separated into zones of compounds. These migrating zones of individual components of the sample mixture are referred to as bands. The migration of a band through the column is known as the elution of the compound (as in TLC). The band eventually migrates out of the column and through a detector; the detector is, in turn, connected to some recording device which registers a deflection of a pen as each band passes over the detector's active surface. The tracing resulting from the elution of a single band is known as a peak.

These microparticulate beds allow many different types of chromatography to exploit the HPLC systems. For example: the HPLC-version of liquid-solid chromatography involves the use of the native silica particles as the SP (this is simple absorption-chromatography). However, in liquid-liquid HPLC, the particles of the silica have had a liquid chemically bonded to their surface thereby allowing ion-exchange or partition chromatography. It is these "bonded-phase" packings which are responsible for the expansion of the utility of HPLC systems into not only medicine but also other applications which present special chromatographic challenges. Bonded-phase columns are mechanically stable and able to withstand the high pressures of HPLC; they are chemically stable and therefore very versatile; plus, they have relatively long lifetimes and provide excellent and rapid chromatographic separation. Equally obviously, HPLC offers much greater control over the chemistry of the separation than the mass action effects of TLC do.

One type of bonded-phase HPLC, "reverse-phase," has become particularly popular. The name stems from the fact that the bonded SP is non-polar while the MP is polar, in contrast to the traditional configuration of these two phases in liquid-liquid chromatography. The most commonly used bonded, reverse-phase packing materials are different alkyl chains, e.g., a C18 hydrocarbon chain, linked to the silica. Solutes are separated on the basis of hydrophobic interactions with the column. Elution is accomplished by polar mobile phases and occurs in decreasing order of polarity of solutes. The chromatography conditions can be altered around these columns in such a way as to allow for tremendous variability in the kinds of compounds separated from individual mixtures and between mixtures. These reverse-phase columns can even withstand changes in mobile phase composition during a single chromatographic run thereby allowing for extensive programming of separations, if necessary. Reverse-phase chromatography now accounts for 75% of all liquid chromatography.

Reverse-phase HPLC is best-suited to the separation of non-ionic compounds but most biologically significant molecules have ionic, or ionizable, functional groups. These render the molecules polar and do not permit retention to take place on reverse-phase columns. It is possible to circumvent this problem by adding a suitable, large, organic counterion to the MP to form an ion-pair with these ionic functional groups. This is called "paired-ion partition chromatography." Obviously, a high degree of selectivity can be achieved by alterations in the composition of the MP so as to maximize this interaction. The significant factors to be manipulated include: the nature and concentration of the counterion (for basic compounds such as the CAs, alkyl sulfonates are used), the pH of the mobile phase (low pH encourages ionization of bases and thus aids the formation of the ion-pair), the polarity of the solvent used in the MP (addition of methanol, for example, to an aqueous MP aids the partition process by counteracting the effect of the counterion and thereby "speeding up" the separation) and, to some extent, the nature of the SP backbone. In summary, all of the above factors must be taken into consideration when a column is being chosen for a specific separation.

DETECTORS

The bands of solutes eventually migrate out of the column and through a detector which must give a quantifiable response to the compounds in each band. The detector is, in turn, connected to a recording device which provides a permanent record of the events which have taken place at the active surface of the detector. The central problem in biomedical and biochemical investigations is the ability to monitor the minute amounts (i.e. pico-, or femto-gram level) of biologically active compounds. With respect to HPLC, this translates into a need for detection systems with sufficient sensitivity for the analates (i.e. the compounds being analysed), linearity over the physiologically relevent concentration range and compatibility with the chromatographic system. As yet, there is no universal detector for HPLC. In the case of the analysis of catecholamines, to the present time, only two detectors fulfill these requirements: the fluorometric and the electrochemical detectors.

The fluorometric detectors that are used in conjunction with HPLC equipment were simply the next generation of the detectors encountered in the evolution of fluorometry. These detectors have proven to be of considerable value in clinical chemistry but their utility in CA assays has, so far, been severely limited for all of the same reasons as previously discussed in conjunction with the fluorometric CA assay. Even though HPLC offers the detector a more highly purified analate than was possible with previous isolation techniques, the problems of cross-fluorescence by interefering compounds, sensitivity, and reproducibility remain. Selective derivatization to strongly fluorescing compounds, either pre-, or post-column, can overcome some of these problems but adds others. These include the fact that derivatization complicates the analytical procedure considerably and introduces another potential source of error into the assay procedure. Another interesting twist is that any oxygen remaining in the MP that is introduced into the HPLC system may actually quench the fluorescence of these derivatized compounds.

Recently, laser technology has become available in the field of fluorescence detection. It is expected that lasers will also be available for the detection of ultraviolet absorbance. However, the utility of either of these detection modes in complex analyses of structurally similar and molecularly unstable compounds, such as the CA, has yet to be established. As was the case with each of the previous waves in detector technology, analysis of the higher concentrations of the biogenic amines and their metabolites in tissue and urine samples will probably precede the availability of the detector for the plasma analysis.

On the other hand, the technology surrounding electrochemical detectors (ECD's) is rapidly changing and offers a practical solution to some of the classic problems encountered in biomedical analyses.

Electrochemistry is concerned with the interconversion of chemical and electrical energies. That is, chemical changes may be produced by electricity (as in the case of electrolysis) or electricity may be produced by chemical events (such as takes place in a battery). For the latter, electricity (i.e., energy in the form of electricity) flows to or from the system in which the chemical events are occurring; therefore, it is critical that the system consist largely of electrical conductors or be a conductor itself. There are two types of conducting materials—electronic and electrolytic—and some materials exhibit both kinds of conduction. Generally, the most common electronic conductors are metals (such as gold, silver, mercury, platinum) and the most common electrolytic conductors are solutions of acids, bases and salts. The electricity which flows through electronic conductors (i.e. metals which are electrically conducting) is due to a stream of electrons; therefore, no net transfer of mattter occurs. In the case of electrolytic conductors (i.e. the salt solutions), the carriers of the electricity are ions and, in response to a potential gradient, a transfer of matter takes place.

Normally, electrochemical systems consist of both types of electrical conductors: if electricity is passed through such a system (i.e. it would have to pass through the metal or "working electrode"), a quantifiable chemical reaction occurs at the interface between the two types of conductors. This reaction is referred to as an electrochemical reaction and is further characterized as oxidation or reduction depending on whether the generated flow of electrons is to or from the electrolytic carrier (i.e. the salt solution), respectively. The flow of electrons so generated is directly proportional to the concentration of the compound which is the source of these electrons. The tendency of a compound to be oxidized or reduced in response to an electrical field is referred to as its electroactivity. This tendency can be capitalized upon to create detection systems capable of quantifying analate(s) of interest for the purposes of chemical analysis. This phenomenon is exploited by the field of voltammetry, one version of which is solid electrode voltammetry. The detection systems thus created operate on the basis of diffusion-limited electrochemical phenomena.

To be compatible with liquid chromatography, an electrochemical detector (ECD) must be placed in a configuration that is suitable to the scale at which the chromatographic column operates. Furthermore, to be effective in any particular HPLC system, the ECD, in turn, requires that the MP be electroconductive (because the MP is effectively one of the components of the electrochemical reaction); the working electrode surface must be chemically inert; and, the analate(s) to be quantified must be electroactive and ionizable in the chosen MP composition (this latter characteristic is a requirement of the conditions of separation by the column). It is important to appreciate that the working electrode (WE) is also the site of the electrochemical reaction of the analate.

The most common juxtaposition of the critical components of an ECD cell that is encountered in biomedical analyses is the thin-layer type comprising three electrodes connected to a stable power supply and an electronic control board. The column effluent (MP plus or minus analate) is directed to a small, flat compartment (typical volume: 10 $\mu$L) within a sandwich of Kel-F plastic. One side of this compartment is embedded in it a planar, working electrode which is held at a fixed potential (e.g. +0.6 V) by the power supply. The working electrode is usually made of carbon (either as carbon paste or glassy carbon). As the analate passes over the WE surface, it is oxidized (or reduced) in response to the electrical field and generates a current which is quantified by the electronics.

However, the resistance of the mobile phase (i.e. the electrolytic conductor) changes constantly as it passes through the HPLC system and over the WE; this, in turn, affects the potential of the working electrode and affects its ability to quantify an analate. To compensate for this, an auxiliary electrode is used and is held constant relative to a reference electrode (usually Ag/AgCl). Any variation between the known value of the reference electrode and the measured value of the auxiliary electrode is due to the iR drop in the compartment (where "i" is the current passing through "R", the uncompensated resistance) caused by the MP. This discrepancy can be compensated for electronically and eliminated. This allows the WE to maintain a constant potential regardless of variations in the resistance of the solution (i.e., the electrolytic conductor is not constant) and ensures that any additional current that is generated in the cell will come largely, if not exclusively, from the analate of interest.

The electrical current (measured in nanoamperes) resulting from the oxidation (or reduction) of the analate is converted to a voltage and amplified by the electronics of the detector. This voltage is then quantitated by a data-recording device and reported as a peak height and/or analate concentration. The current produced in the cell is directly proportional to the concentration (that is, the number of molecules flowing by the WE) of the analate(s) in the solution. The range switch on the operating controls of the ECD determines the sensitivity of the output of the WE: graded selections are available from 0.1 to 500 nA Full Scale Deflection (F.S.D.). A setting of 5 nA means that a 2.5 nA output signal would correspond to a recorder pen deflection of one-half full-scale.

The signal generated by the MP (and controlled by the auxiliary and reference electrodes) is the source of the "baseline output" that is referred to in discussions of the output of the HPLC-ECD system. It is important to appreciate that any current produced by the analate as it, in turn, passes over the WE surface will be superimposed on this tonic signal (recall that the MP is a vital part of the electrochemical reaction and is constantly flowing through the electrochemical compartment in a wet system, i.e. liquid chromatography). Obviously, the ability to discriminate the current produced by an analate will depend on the quantity of background signal generated by the MP; the less background signal present, the more visible will be the current from the analate. In fact, the stability, linearity, reproducibility and utility of an electrochemical detector depends entirely on the control of this background signal.

The characteristic electroactivity of a compound offers a certain basis for discrimination but this is insufficient to ferret out individual components of a complex mixture. This latter issue is the function performed by chromatography. The role of the electrochemical detector (ECD), then, is to quantify individual compounds once they have been isolated by the chromatography. It is expected that future technology in this area will permit the characterization of the individual components of a complex mixture without the need for prior separation but this is not yet available. It is noted that this type of direct analysis of complex mixtures is offered by the field of polarography but the equipment has not yet been adapted for the analytical challenge of the low levels of physiologically significant molecules encountered in biochemistry. At the moment, only inorganic and selected organic analyses can be performed with current polarography machines.

There are, in fact, two types of electrochemical detectors: the coulometric and the amperometric. The coulometric detector permanently oxidizes 100% of the molecules in the flowstream passing over the working electrode and therefore generates a much larger current than the amperometric detector, which only oxidizes about 10% of the molecules. In practice, the higher yield of the coulometric detector does not seem to improve its sensitivity because the background noise level is also significantly increased. This results in a poor signal:noise ratio thereby nullifying any benefits from the larger signal. Alternatively, the amperometric detectors permit collection of most of the analate following its passage through the cell and thus further purification is possible, if necessary. Therefore, the amperometric detector is most often encountered in biomedical applications.

Electrochemical detectors are commercially available from, inter alia, Bioanalytical Systems (BAS) [Bioanalytical Systems Inc., W. Lafayette, Ind. 47906.] (amperometric) and ESA [ESA, Inc., Bedford, Mass. 01730.] (coulometric).

DATA RECORDERS

An HPLC-ECD system produces data as a variable response over a unit of time: this is most easily represented in a Y vs. X format. The actual amount of time required for an individual compound to pass through the system is called its retention time. In physical terms, this is the amount of time between injection of the sample and its passage over the WE. Under a standardized set of chromatographic conditions, this time is so specific that it can be used to identify eluting compounds; hence, pumps which can supply reliable flow of mobile phase are very important. As explained above, the magnitude of the ECD's response to the molecules flowing over it is directly proportional to the quantity of the molecules present (i.e., in that chromatographic band).

Normally, the ECD response is displayed on a strip chart recorder as a sequential series of peaks comprising the chromatogram. The desired peak shape (i.e. the profile of a chromatographic band passing through the detector) is Gaussian. To quantitate this chromatographic data, either the area or the height of each individual peak is calculated and simple mathematics (with reference to standards) converts this back to concentration per milliliter of plasma. The linear range of the detector must be established so that unknown samples can be quantified realistically. The aim of the chromatography is to optimize the separation between peaks (known as resolution) so as to make this quantification as accurate as possible.

In recent years, automatic data processing of peaks by advanced digital integrators has become available. The accuracy and reproducibility of the data produced by the integrator depends entirely on the accuracy and precision of the chromatography. However, the utility of these integrators in CA assays has been limited by the available software and its corresponding inability to deal with the complex chromatographic conditions of this analysis.

Identification of the peaks on the chromatogram is on the basis of retention time, as was the situation in TLC. In the case of HPLC systems, a library of retention times of compounds (standards) which are structurally related to the analates of interest and present in the sample matrix is established prior to the start of the analysis of unknown samples. However, it must be emphasized that the coincidence of the retention time of a component of the sample mixture with the retention time of a previously injected standard compound is not proof of the identity of the unknown component. Complete characterization of every peak on the chromatogram entails collection of the effluent of the column and subjecting each peak to extensive analysis. This analysis could include GC-MS, determination of relative current ratios ($\phi$), enzymatic peak shift, and fluorescence emission spectra. [Ref.: Brown, Hartwick and Krstulovic, pg. 307-335 in: Biological and Biomedical Applications of Liquid Chromatography II; Vol. 12, Chromatographic Science Series, Edited by Hawk, Marcel Dekker, Inc., New York, 1979.] Obviously, it is impractical to perform such comprehensive analyses on every peak of every chromatogram on an on-going basis. Therefore, these studies are performed on the peaks of interest when the analytical procedure is first being established in the laboratory and at regular intervals thereafter as a quality-control measure. This point will be considered further hereinbelow.

OVERVIEW OF HPLC-ECD CATECHOLAMINE ASSAYS

The introduction of ECD's sensitive enough to detect even resting levels of CAs has resulted in reverse-phase HPLC-ECD becoming the preferred method for analyzing plasma extracts for CA concentration. [Ref.: Holly and Makin, Analytical Biochem. 128(2):257-274, 1983.]. The entire assay (including extraction, chromatography and detection) requires, at most, two hours to complete the analysis of one blood sample, from frozen plasma to finished chromatogram. Trouble-shooting is thus greatly simplified by the speed of the procedure and the small number of intermediary steps. This offers a significant advantage over previous assay methods (e.g., REA) which required up to two days to complete and in which trouble-shooting was an extremely laborious undertaking.

However, the HPLC-ECD method has also had a number of problems; these include the maintenance of a number of complex instruments which can be capricious when required to work at their limits of capacity on a continuing basis, as is required by human plasma CA assays. The main elements of the assay are: extraction of CAs from plasma (chemical process); separation of the CAs from each other (by HPLC); and, detection and quantitation of the individual compounds (by ECD and an integrator, respectively).

EXTRACTION OF CATECHOLAMINES

Quantification of CAs in an HPLC-ECD system requires that the CAs first be extracted and concentrated from plasma. This is a limitation partly imposed by the choice of chromatographic methods and partly by the inherent complexity of the plasma: the column requires a small volume injection (e.g. 50 $\mu$L) of a highly concentrated sample. Obviously, if the column is chosen for its ability to discern between molecules of small and very similar molecular weights (for example, 175 to 225), the column will not be able to handle very large (for example, 500,000) molecular weight molecules (e.g. proteins) without sustaining damage to the chromatographic bed. Furthermore, the smaller the injection volume, the narrower will be the peak on the chromatogram and the greater will be the resolution because of improved separation and hence the more accurate, sensitive and reproducible the quantitation will be.

Producing as "clean" a sample for injection as possible is important because this part of the assay often determines the ultimate success of the entire procedure. Desirable properties of a good extraction technique include: specificity for the analate(s) of interest and removal of interfering compounds (this not only prevents overloading of the column but also assists resolution of the analates by the column); concentration of the sample into as small a volume as is practical; and transfering the analates into the most appropriate carrier solution in preparation for separation and detection by the HPLC-ECD system.

A variety of approaches to the extraction of the analates of interest from a complex matrix are possible. For example, compounds of interest can be divorced from the matrix by chemical extraction, by concentration on a column, by precipitation out of the matrix or by precipitation of the rest of the matrix away from the compounds of interest.

In catecholamine analysis, the options for removing and concentrating the CAs out of plasma include activated alumina (effectively, a precipitation technique) and a boric acid extraction technique (a chemical extraction). The chronic problems with either of these alternatives are specificity, efficiency and reproducibility. That is, the object is to take out only the CAs, preferably to the full extent that they are present in plasma and to that same extent on a day-in, day-out basis. Additionally, the extraction technique must deliver the sample to the separation step of the assay (i.e. the HPLC-ECD system) in the most appropriate solvent. In practice, this is an ambitious goal.

Activated alumina was first used in CA assays in the early 1960's. [Ref.: Anton & Sayre, J. Pharmacol. Exp. Therapeut. 138:360-375, 1962.]. The idea behind the method is that activated alumina particles will differentially adsorb CA molecules (from urine or plasma) which can then be eluted from the alumina. The actual procedure is quite simple: acid-washed alumina is added to an aliquot of plasma; the mixture is shaken together for a time; then the plasma is removed (either by centrifugation or elution); the alumina is washed with water to remove unwanted materials; and, finally, the CAs are eluted from the alumina with a perchloric acid solution which can then be directly injected into the HPLC system. In practice, while this procedure is very brief, it is not very successful.

Firstly, alumina will grasp many things from plasma besides just CAs. The exact physicochemical basis for this attraction is neither known nor controllable. Secondly, the efficiency of the technique is very low, viz., only 40 to 60% of the CAs present in plasma will actually be extracted. Furthermore, the perchloric acid carrier solution imposes limitations on the chromatographic separation conditions which can be used (i.e., to only those which will tolerate the acid).

The reproducibility of the technique is the worst problem: batches of alumina vary tremendously in their efficiency. No matter how large a stock of a "good" batch of alumina is available, it will run out eventually and possibly in the middle of a series of experiments or analyses. Neither is the alumina's behavior over time predictable, even if a batch has been declared suitable at the outset. Individual batches are not necessarily inert or stable in the laboratory environment. The material itself is very capricious and difficult to handle uniformly and there is a good deal of "folk-lore" associated with the treatment methods for the alumina.

Inter-laboratory differences in techniques as well as results obtained using alumina vary tremendously. This latter problem may be caused by the fact that the characteristics of the alumina available on the scientific marketplace vary with location. Some European laboratories, for example, consistently report better results with alumina than anyone else, and there is no way to determine if the alumina itself is the cause or if variation in techniques utilized is responsible for the discrepancy.

Numerous attempts have been made to solve these problems, with the result that additional complexities were created in the process. For example, the alumina extraction has been coupled to a radioenzymatic assay in the hope that the recovered yield could be improved. However, alumina is not an inert material: it inhibits COMT (the enzyme used in the REA) thereby, if anything, reducing the yield from the assay. [Ref: Gauchy, Tassin et al, J. Neurochem. 26:471–480, 1976.]. Alumina was also found to interfere with the fluorescence detector if all of it was not removed from the solution. With the development of the ECD's, it was hoped that these and other problems could be circumvented. Unfortunately, this has not proven to be the case because alumina is also incompatible with optimal operation of the ECD (described more fully hereinbelow).

The chemical extraction of CAs from physiological fluids using boric acid was investigated in the late 1970's as an alternative to precipitation of CAs with alumina. [Ref.: Molnar and Horvath, Clin. Chem. 22(9):1497–1502, 1976; Horvath, Melander and Molnar, J. Chr. 125:129–156, 1976; and Molnar and Horvath, J. Chr. 145:371–381, 1978.] The method involves the extraction of the CAs from plasma in an organic solvent by the use of ion-pair formation with diphenylborate. It is also simple to perform and requires only about one half-hour to proceed to completion. The recovery of CAs from plasma is very high (80 to 100%) and the method is very reproducible. [Ref.: Smedes, Kraak and Poppe, J. Chr. 231:25–39, 1982.]

Variations on this theme are performed using boric acid gels but these methods have been more difficult to control than the Smedes et al method. Furthermore, to date, these gels have been used largely in conjunction with fluorometric assays; as such, they are subject to the same limitations as all fluorometric methods. The utility of immobilized boric acids in HPLC-ECD methods and any special advantages conferred by them to plasma CA assays has yet to be demonstrated.

Intra-, and inter-assay variability of the boric acid extraction can be monitored and standardized by adding a known amount of an internal standard to the plasma prior to extraction.

Lastly, it is important to appreciate that because boric acid extraction of the CAs from plasma is on the basis of chemical structure, any other molecules present in plasma which have a similar structure will also be extracted. [The critical structure in common is a benzene ring with two adjacent hydroxyl groups]. Commonly used drugs such as ephedrine will also follow the CAs out to the chromatogram and interfere with their separation. Before any extraction procedure can be utilized on a regular basis, the degree of cross-contamination by interfering substances must be established and controlled. Among other factors, this is also the reason that the assay procedure described herein has such wide applicability, i.e. it is useful in the analysis of any CA-like molecule from a multiplicity of sources.

HPLC SEPARATION OF CATECHOLAMINES:

Once the CAs have been extracted and concentrated from the plasma, they must then be separated from each other and quantified. The two most critical aspects of this part of the CA assay involve (a) the column and chromatographic conditions, and (b) the detector.

With respect to the column and chromatographic conditions, the selection of the components of the stationary and mobile phases is critical.

As discussed hereinabove, reversed-phase HPLC technology is advantageous for separating CAs from one another. In the case of the special requirements of CA assays, the only stationary phases which have proven effective are reverse-phase, irregular, 10 $\mu$ (or less), bonded $C_8$, bonded $C_{18}$ and bonded Phenyl packings. The Phenyl packings are ideally suited for CA separation from a theoretical point of view but have heretofore not been used widely for this purpose. One of the constraints on the use of any HPLC column is that these columns are generally not able to withstand more than about 3500 psi of operating pressure.

One of the restrictions of the smaller particle sizes for the stationary phase of HPLC columns is that more care must be exercised with the solvents used to run the system and with the sample which is injected onto it. For example, it is of critical importance that the sample (i.e. analate to be quantified) be completely dissolved in the carrier solution; and, all of the fluids which enter the column must be particle-free. This imposes the restriction that the sample must be soluble in the solvent which is suitable to the column. Partial solubility is ultimately manifested as long, tailing peaks and, in turn, poor resolution of the peaks on the chromatogram; incomplete recovery of sample from the column, a contaminated column and a passivated detector may also occur. These problems may also result from an overloaded column, or a column with a mechanical defect (such as a disturbed bed or non-homogeneous packing material) and/or non-equilibrium of the sample molecule (i.e. incomplete ionization of the analate by the mobile phase).

Certain restrictions to the composition of the mobile phase are immediatedly imposed by the choice of column and detector to be used in the HPLC system. For example, the electrochemical detector requires a conductive MP and the reversed-phase column requires an aqueous mobile phase (rather than one based on organic solvents). The exact composition of a MP for any given separation is determined first by the needs of the HPLC-ECD hardware and secondly, by a series of tests. These tests are designed to determine the effect of varying the exact composition and concentrations of the components of the MP on the CA peaks from the point of view of the separation of the CAs from each other and from the solvent front.

The base of the mobile phase must be an aqueous salt solution made from a common buffer material such as potassium phosphate and set to a pH which can not only maximize the ionization of the CAs and the counterion but which will also allow the column to function optimally. For example, various reversed-phase columns can operate in the pH 2 to 7 range but the actual effective operating pH of any particular system is determined by a variety of factors [For a more detailed discussion of these factors, the reader is referred to Moyer and Jiang, J. Chr. 153:365–372, 1978.]. The ionic conditions created by the chromatographic system are one of the most critical determinants of effective separation by this type of column. When the operating conditions are being chosen, it must also be taken into consideration that prolonged exposure of a reversed-phase column to aqueous-solvent solutions of high pH will lead to dissolution of the chromatographic bed. It is also important to ensure that the mobile phase is maintained de-gassed prior to and during its passage through the apparatus: not only would air disrupt flow through the system and affect the detector but it would also alter the pH of the MP thereby altering the separation characteristics of the column.

The CAs are bases (whereas their metabolites are acids) and are hydrophilic (that is, they ionize easily and stay in the water phase). The native CA molecules are not well-retained on a reversed-phase column, which is non-polar. It is possible, however, to alter the chromatographic conditions so as to overcome this problem yet still retain the advantages offered by reversed-phase columns. This is accomplished by the use of the so-called paired-ion partition chromatography techniques, clarified in 1973 by Eksborg et al, [J. Chromatogr. 83:99–110, 1973. and Anal. Chem. 45(12):2092-2100, 1973]. Specifically, the CA molecules are encouraged to form ion-pairs with large, organic counterions (called ion-pair reagents or ionic surfactants) in an aqueous mixture set at a pH value which will maximize this tendency.

The counterion (that is, an ion of the opposite charge to the CA) is lipophilic and interacts with the column thereby indirectly increasing the interaction of the CAs with the column and allowing separations to take place. This tendency can be modulated by alterations in the concentration and structure of the counterion chosen. For basic compounds, such as the CAs, an alkyl sulfonate (for example, heptane sulfonic acid) is used as a counterion. It is pointed out that the exact mechanism of ion-pair formation and/or the interactions with column is unknown. [Ref.: Krstulovic, J. Chr. 229:1-34, 1982.]. Fine control of the retention of the counterion-CA pair is ultimately achieved by the addition of an organic solvent to the mobile phase which counterbalances the retention on the column induced by the counterion. Most often, this translates into a small percentage of the mobile phase being composed of acetonitrile or methanol.

Another important problem in the choice of mobile phase compositions is that the CAs are very sensitive to heavy metal ions; these ions will chelate CAs out of solution and enhance their decomposition. The MP's which are normally used for separation of CAs are acidic and therefore, relatively corrosive in the HPLC system. The net result of this is liberation of heavy metal ions from the machinery. This is another one of the reasons that the materials which make up the HPLC system must be chemically stable and inert: i.e. the apparatus needs crystalline and teflon parts in those areas of the system which experience the greatest amount of mechanical wear and which will be coming into contact with the MP.

It is of critical importance to filter the MP both prior to and during its passage through the system to prevent it from picking up stray metal filings (microscopic-sized) and depositing them on the column and permitting interaction with the CAs. As an added precaution, the mobile phase usually contains a chelator of heavy metal ions such as EGTA ethylenebis-(oxyethylenenitrilo)-tetraacetic acid or EDTA (ethylenediamine)-tetraacetic acid) to bind any heavy metal ions which happen to come through from the injector or the pumping system.

Clearly, a regular maintenance routine must be instituted to maintain the HPLC-ECD system free of particles and air which would not only damage the column and passivate the working electrode but could also destroy the CAs. One aspect of the maintenance procedure is a periodic, systematic wash of the HPLC-ECD hardware (including or excluding the column). It is exactly this wash sequence which is the least well-known aspect of maintaining an HPLC system functioning optimally. Without it, the entire HPLC-ECD system could easily cease to function on a regular basis.

ELECTROCHEMICAL DETECTION OF CATECHOLAMINES:

As discussed hereinabove, fluorescence detectors have been used with HPLC for CA assays. However, the mere measurement of native fluorescence of picogram quantities of catecholamines for their quantification does not yield acceptable results. Enhanced sensitivity of detection can be achieved by derivatizing the catecholamines to more strongly fluorescent molecules such as trihydroxyindole or o-phthalaldehyde. Used in conjunction with HPLC, these derivatizations can be performed either before or after separation of the catecholamines by the column. However, this complicates the HPLC system and imposes limitations on the choice of options for the separation conditions. Furthermore, there remains the issue of dealing with other constituents of plasma which may fluoresce naturally or which will also be derivatized. Considering these complications, the reproducibility problems associated with the method, and the fact that this type of assay requires one to two milliliters of blood per sample, clearly this is not the optimal detection system with which to search for catecholamines in human plasma.

It has become obvious that electrochemical detectors (ECDs) offer a practical solution to the problem of detecting very low concentrations of electroactive, physiologically significant compounds. [Ref.: Kissinger, Bruntlett and Shoup, Life Sci. 28:455-465, 1981.] Several aspects of the use of ECDs in the quantification of human plasma CAs are discussed below.

Fortunately, CAs readily form o-quinones under the influence of an applied voltage and can be detected by ECDs. [Ref: Sternson, McCreery et al, Electroanal. Chem. Interfac. Electrochem. 46:313-321, 1973.]. Because of the level of sensitivity possible for the new electrochemical detectors and, therefore, the freedom from the need to derivatize the CAs prior to their quantification, this has become the favored detection mode to use in HPLC catecholamine assays. The actual detection limits of the electrochemical cell are determined by, among other things, the chromatographic efficiency, the detector's conversion efficiency and the baseline noise. Unfortunately, these parameters are not independent and many factors relevant to the successful use of the ECD in CA assays are pertinent to this discussion.

The use of an electrochemical detector has certain implications for the HPLC system because it imposes a variety of restrictions on it. For example, the ECD requires a conductive mobile phase; therefore, the organic solvent MPs used in normal-phase chromatography are not compatible with this mode of detection. Reversed-phase columns are the only ones which are suitable for this detector. The composition of the working electrode (WE) must also be compatible with the MP; for example, a WE made of carbon paste would be damaged by acetonitrile in a MP.

It is important to consider that the ECD produces the final result of the cumulative effect of the processes of extraction, separation, detection and quantitation of the analate of interest from the matrix of origin. The chromatogram contains all of the information regarding not only the analate but also the events which occurred during its isolation. Any interferences or difficulties which occurred during any step or part of the assay procedure will leave a trail of electroactive molecules which will be manifested on the ECD's output recording. Therefore, careful attention must be paid to all signals generated by the HPLC-ED system because they provide information about the state of the system and the success of the assay.

It must be borne in mind that the ECD is attempting to measure the potential difference between the working electrode and something in the solution going by it. However, the mobile phase is itself always going by the WE; the MP is conductive and it carries things which will ionize in response to the electrical field created by the ECD cell. All of these things will generate a tonic, "background" current which is compensated for by the auxiliary electrode. The current generated by an analate in the flowstream will, by definition, be superimposed on this background current produced by the MP. Clearly, the actual amount of background current will determine the functional range and sensitivity of an ECD. Therefore, it is of critical importance to an analytical procedure to reduce the extent of this background current (referred to as "the baseline" recording) because it obviously interferes with the signal generated by the analate. In fact, there are a number of signal types emanating from the system which must be monitored continuously.

The baseline recording produced by the ECD is defined as the tracing seen on a strip chart (or similar) recorder when the HPLC-ECD system is operating under baseline conditions. These conditions imply that the system is running at the normal analytical operating speed (about 2.4 to 2.8 mL/min. of mobile phase, saturated with helium, flowing through the system) and at the selected operating pressure (about 2400-2800 psi) with the detector cell set and equilibrated to 1 nA F.S.D., without any injections having been made. The baseline recording thus reflects tonic, background signals from the detector cell; this background has been generated by the mobile phase and the entire HPLC system up to that point. A "good" baseline signal is one which appears as essentially a stable, horizontal line on a strip-chart recorder and does not drift and has minimal, shallow waves on it.

After an ECD cell is connected to an HPLC system and turned on, it takes about 48 to 72 hours of running at full operating speed and pressure for it to achieve this baseline state of equilibrium within the system. The achievement, and maintenance, of this equilibrium state is one of the most critical aspects of the use of an ECD and one of the least well-understood. It must be reiterated that the dynamic state of the baseline will determine the sensitivity, reproducibility and utility of the cell. Optimal function of the working electrode must first be attained and subsequently maintained. Once a cell has equilibrated within the system, it is not turned off (except during repairs to the system); this is especially true if the cell is being run at high sensitivity levels. In biomedical applications, this is invariably the case.

To be able to detect the minute levels of CAs present in resting human plasma, the HPLC-ECD system must be set at, or near, its maximal sensitivity. Resting plasma CA concentrations are approximately 150-300 pg/mL NA, 20-75 pg/mL A, and perhaps 0-100 pg/mL DA. Besides the fact that these are exceedingly small amounts, the CA molecules are not highly electroactive, i.e. CAs have only two protons each to donate in response to an electrical field. Within an HPLC-ECD system, this translates into an extremely small pen deflection on a strip-chart recorder even when the detector is set at the highest, convenient sensitivity level, for example, at one nano-amp (1 nA) F.S.D..

An injection of a standard solution of CAs which represents a plasma concentration of two or three times the resting value yields peaks of the following size at 1 nA F.S.D.: 500 pg NA is a peak of only about 65% F.S.D.; 100 pg A is a peak of only 9% F.S.D.; 200 pg DA is a peak of only 9% F.S.D. If the graph part of the chart paper is 12.5 cm. wide and the baseline is 0.5 cm. above the bottom of the paper, 10% F.S.D. is a peak only 0.8 cm. high.

However, even under conditions of a maximal exercise stimulus when normal human plasma CA concentrations are maximal, the highest range setting ever needed on the ECD to visualize the CAs is 2 nA F.S.D. The reason for this lies in the facts of the extraction procedure, i.e. how the CAs are concentrated from plasma. It must be borne in mind that once the CAs have been extracted from plasma, an injection is made of only a fraction of the total amount of the CAs actually present because a limited volume of the extract is analysed by the HPLC-ECD system. No practical method yet exists by which only CAs are removed from a sample of plasma and concentrated into a very small volume (e.g. 50 μL) all of which could then be available for analysis. [Some kind of on-line separation technique could be the one possible method to assay all of the CAs in a sample volume given that any and all handling of the sample leads to losses of analate.] If only a very small amount of analate is present at the beginning (as is the case with the CAs in resting human plasma), then the effect of losses, in transit to a quantification technique, are thus magnified and more serious.

Even if the plasma contained 6000 pg/mL NA and 1000 pg/mL A, extraction of CAs from two mL of plasma into 250 μL of acetic acid and injection of 50 μL of that, in turn, would only contain 400 pg A to be separated by the column: at 2 nA F.S.D., this is a peak that is only 2 centimeters high (at most); the corresponding NA would be off-scale at this setting (2400 pg NA corresponds to a peak height of 65% F.S.D. at 5 nA).

It is important to understand that the range setting on the ECD affects not only the physical size (on the paper trace) of the output but also the sensitivity of the cell itself. That is, the stability of the detector cell at a range setting of 5 nA is considerably higher than the stability of the cell at 1 nA. Therefore, it is the range setting which can be reasonably maintained that will determine the functional sensitivity of the ECD. The use of dedicated integrators for handling the output of the HPLC-ECD system has altered, somewhat, the need for the restriction of obtaining peaks that are on-scale. The reason is that the integrator can monitor the actual current (i.e. analog signal) being produced at the working electrode surface and convert that into a digital peak. The information is preserved as a voltage change over time and the computer uses it to calculate the peak height (or area); these data are then stored, permanently. Therefore, the actual "picture" (i.e. the real-time recording trace of events) of the chromatogram is not necessary. However, the integrator cannot assist with the chromatographic challenges of maintaining stable WE function at 1 nA nor can it compensate for an inability to do so.

An important complication to these issues is the presence of baseline noise. It must be remembered that the chromatogram produced by the extracted CAs will be superimposed on the signal that is tonically generated by the HPLC-ECD system. Obviously, the size of the background signal will affect the discrimination of the peaks of interest on the chromatogram: if the peaks are only several hundred picoamperes high, a background signal of several nanoamperes would completely obliterate the data. Baseline noise is defined as the unwanted, random pattern signal (of indeterminate, and possibly multiple, origin) which appears on the steady-state, baseline recording. This would result in a "bad" baseline, defined as a baseline tracing which has many waves on it of variable magnitude and range with or without a general drift on the recording (see FIG. 3B).

Unfortunately, baseline noise can be, and normally is, generated by a wide variety of sources, including: other compounds in the plasma having a similar enough structure to the CAs so as to survive the extraction procedure; the contaminant constituents of the MP, the electrochemical cell itself (if things adhere to its surface, for example, and continue to release electrons), chemicals leached from the column or compounds being leached from the pump and injection systems, plus the summation of pump pulsations, flow cell hydrodynamics, static electricity, power line noise and electronic amplification and/or disturbance all may contribute to the "noise".

Baseline noise can also be generated indirectly by things which disrupt flow through the system. Included in these factors are dissolved gases in the mobile phase: by disrupting laminar flow through the system and ionizing at the electrode surface, they contribute to disruption of the baseline recording. Furthermore, the presence of air in the mobile phase alters the pH and conductance of the mobile phase and hence the ionization of the stationary and mobile phases; the conditions of separation are thereby altered and that imbalance is also manifested as baseline noise. Additionally, contaminants can passivate the working electrode's active surface thereby reducing its sensitivity and amplifying the effects of the baseline noise on the chromatogram. Baseline drift is caused by the presence of air in the mobile phase, solvent impurity and/or clogged filters in the flowpath of the mobile phase utimately causing disruption of flow. The other problem with dissolved gases is that they could come out of solution in the mechanical parts of the HPLC system and either disrupt laminar flow through the system, repack the chromatographic bed or, partially block the fine tubing by creating eddy currents around the gas bubbles. The net effect of all of these factors is more baseline noise.

It is also important to consider that if the detector is operating at very high sensitivity ranges such as 1 or 2 nA F.S.D., any impurities borne on the mobile phase will also be ionized and will ruin the baseline recording as well as the differentiation of the peaks on the chromatogram.

It is for these reasons that the water, and all of the other chemical constituents of the mobile phase must be of the highest purity available (i.e., contaminants reduced to parts per million (ppm) with parts per billion (ppb) desirable). In fact, the technology of making "clean" compounds has not yet caught up to these detectors fully.

Furthermore, it is imperative that the mobile phase be extensively filtered, de-gassed and maintained thus prior to and during use. This is why the apparatus must be fitted with an array of filters all along the flowstream, why the components of the MP must be ultrapure, and why the reservoir of the MP must be continuously purged with an inert gas. This is also why the injected sample (containing the unknown analate(s)) must be as free of interfering substances as possible.

Attempts have been made to minimize these problems by putting several working electrodes in series, or in parallel, but this has not yet represented a significant improvement in the limitations of CA assays. Therefore, it is common practice in HPLC assays of CAs to use amperometric detectors with only a three-electrode assembly (i.e. working, reference and auxiliary electrode). The technology which comprises these electrochemical detectors is evolving very rapidly. It is highly recommended that as each improvement is made to the machinery, it is incorporated into the methodology of the plasma CA assay.

The significance of and/or the required level of adherence to, the above-described techniques in employing HPLC-ECD technology for the analysis of the resting levels of human plasma CAs has heretofore gone unrecognized. For example, while it has generally been known that the HPLC-ECD apparatus must be kept clean, and that the materials used must be of high purity, the significance of very high levels of cleanliness and purity had not been recognized in the context of operating the electrochemical detector at a sensitivity level of one nanoamp. It is emphasized that such a sensitivity level is unavoidable for proper assaying of physiological amounts of CAs. At such a sensitivity, however, the baseline is adversely affected by impurities to an extent that continuous, optimal performance of the assay is impossible without the extraordinary measures which are the basis of the present invention. The assay techniques described herein permit the continued operation of an HPLC-ECD system at 1 nA F.S.D. for the purpose of maintaining a reliable plasma CA assay.

DISCLOSURE OF THE INVENTION

It is accordingly an object of the invention to provide a method for assaying catecholamines and other small molecular weight, physiologically significant compounds taken from the group of biogenic amines, their derivatives and metabolites, using high pressure liquid chromatography in conjunction with an electrochemical detector.

It is another object of the invention to provide a method, as above, which permits the assaying of catecholamines and related, small molecular weight physiologically significant compounds obtained from physiological fluids (including plasma, cerebrospinal fluid and urine) and tissue extracts.

It is another object of the invention to provide a method, as above, which permits the assaying of catecholamines and related, small molecular weight physiologically significant compounds obtained from other sources including prepared standard compounds of this class and compounds obtained from plant material.

It is still another object of the invention to provide a method, as above, which includes a protocol for reducing the baseline noise in the output from the electrochemical detector.

It is another object of the invention to provide a method, as above, which includes a protocol for maintaining an electrochemical detector cell functioning at one nanoamp (or less) full scale deflection for a prolonged period of time.

It is yet another object of the invention to provide a method, as above, which is capable of assaying catecholamines (including noradrenaline, adrenaline and dopamine) at resting levels typically encountered in human blood plasma.

It is another object of the invention to provide a method, as above, which is capable of extracting catecholamines from human plasma reliably and reproducibly.

It is still another object of the invention to provide a method, as above, which includes a protocol for validating the performance of the extraction method.

It is still another object of the invention to provide a method, as above, which includes a protocol for validating the performance of the apparatus used in the method.

These objects and others are achieved by a method for the assaying of catecholamines contained in blood plasma, the method comprising the steps of (a) preparing a sample suitable for assaying of catecholamines from blood plasma, (b) injecting the sample into a high pressure liquid chromatography apparatus, the apparatus including: (1) a chromatography column containing a quantity of irregular microparticulate-silica bonded phenyl groups as a stationary phase, (2) a substantially residue-free mobile phase passing through the phenyl-bonded stationary phase, the mobile phase comprising from about 20 mM to about 300 mM of a buffer having a pH of from about 2 to 7, from about 0.1 mM to about 10 mM of a chelating agent, from about 0.1 mM to about 10 mM of an alkyl sulfonate, the alkyl sulfonate having from about 4 to about 14 carbon atoms, and from about 0.5% to about 15%(v/v) organic solvent in water solution, (3) a pump for pumping mobile phase phase through the stationary phase, (4) an injector for transferring the sample into the apparatus, and (5) a guard column positioned upstream of the chromatography column through which the mobile phase passes, (c) eluting one or more catecholamines from the column, (d) transferring the eluted catecholamines into an electrochemical detector set at one nanoamp (or less) full scale deflection, (e) measuring the current output from the electrochemical detector to obtain a qualitative analysis of the catecholamines, and (f) integrating the current output from the electrochemical detector to obtain a quantitative analysis of the catecholamines, wherein the signal to noise ratio of the current output is at least 2 to 1.

The objects of the invention are also achieved by a kit suitable for use by laboratories.

BRIEF DESCRIPTION OF THE DRAWINGS

For a complete understanding of the true scope of the invention, the following detailed description should be read in conjunction with the drawings, wherein:

FIG. 5C is a recorder/integrator tracing of an example of a chromatogram produced by the injection of an extracted sample of human plasma containing an unknown quantity of catecholamines into the HPLC-ECD apparatus set at one nanoamp full scale deflection.

FIG. 7 A-D are examples of the standard curves of four catecholamines, representing the sensitivity of the electrochemical detector (in terms of microvolts output) for the catecholamines at one nanoamp full scale deflection under the operating conditions of the invention. Additionally, these curves demonstrate the varying electroactivity of the individual catecholamines.

DETAILED DESCRIPTION OF THE PREFERRED EMBODIMENTS

The present invention relates to the combination of factors and equipment which permit a catecholamine (CA) assay to be performed, using newly available HPLC-ECD technology, at an operating level that is useful to the real-life challenge of CA measurements of human plasma.

DESCRIPTION OF HPLC-ECD APPARATUS

Figure 1:
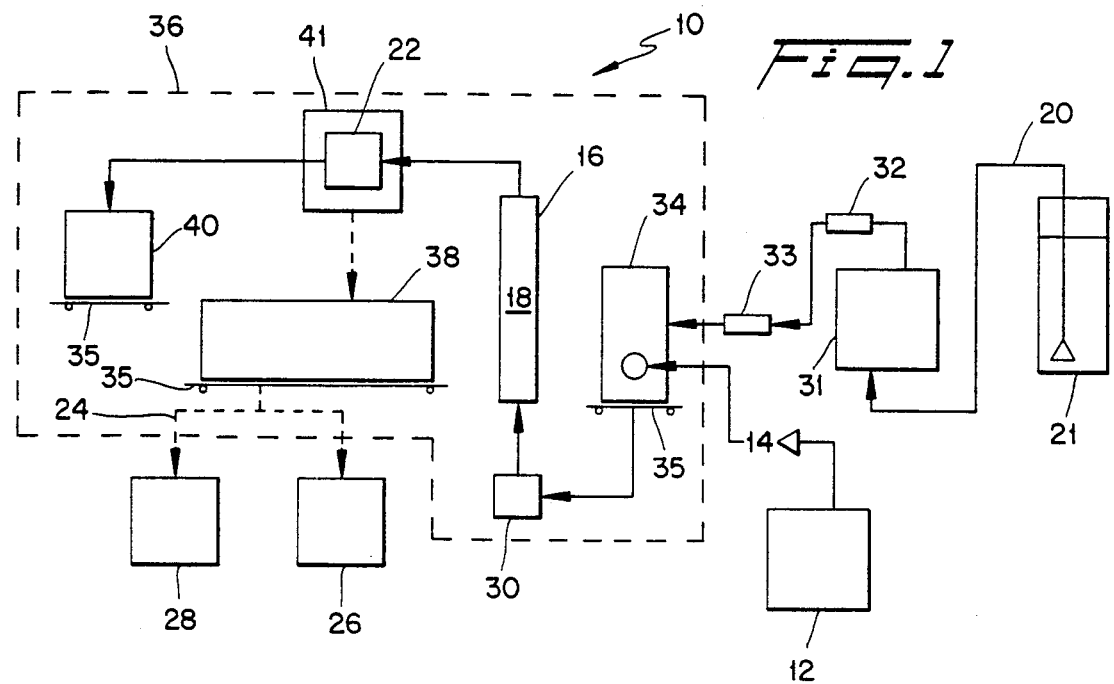
FIG. 1 is a schematic representation of one embodiment of a high pressure liquid chromatography and an electrochemical detector system of the invention.

FIG. 1 illustrates the apparatus of the invention in schematic form. The HPLC-ECD assay system, generally indicated by the number 10, includes a catecholamine extraction technique 12 which prepares a sample 14 containing CAs suitable for injection into an HPLC column 16. The column 16 contains a stationary phase 18 comprising irregular microparticulate-silica bonded phenyl groups. A mobile phase 20, purged with a noble gas and filtered in a reservoir 21, is continuously passed through stationary phase 18. The sample 14 is injected into the mobile phase 20 and is carried through the stationary phase by means of the mobile phase. Pressures in the column 16 are generally between about 2200 and about 3000 psi.

As explained previously, the various CAs have different residence times within the column, and thus each CA elutes at a characteristic time. The sample eluting from the column is fed to an electrochemical detector 22 which detects the presence of CA in the sample and outputs an electrical signal 24 which varies quantitatively with the amount of CA in the sample. This electrical output 24 is fed in parallel to a strip chart recorder 26 and an integrator 28, the latter calculating the quantity of each CA in the sample from the signal output 24.

To reduce as much as possible the presence of impurities entering the HPLC column, a guard column 30, comprising irregular microparticulate-silica bonded $C_{18}$ groups, is positioned upstream of the column 16. Thus, the mobile phase 20 must first pass through the guard column 30 prior to column 16. The mobile phase is pumped into the guard column 30 by means of a pump 31. The mobile phase passes through a pulse dampener 32 and an in-line filter 33 upstream of an injector 34. [It must be noted that pulse dampener 32 is an adjunct to the pulse dampener that is a standard (i.e., built-in) part of the pump 31. It has been found that additional pulse dampening is required to maintain satisfactory control over baseline noise at 1 nA F.S.D.] Injector 34, positioned on one or more electrical isolation platforms 35, is provided for injection of sample 14. A Faraday cage 36 surrounds the injector 34, column 16, electrochemical detector cell 22, electronic control box 38 controlling the cell 22, and waste container 40 which receives effluent from cell 22. A separate Faraday cage 41 surrounds cell 22.

The actual HPLC-ECD apparatus just described is commercially available from, inter alia, Waters Chromatography Division [Milford, Mass. 01757.].

Figure 2:
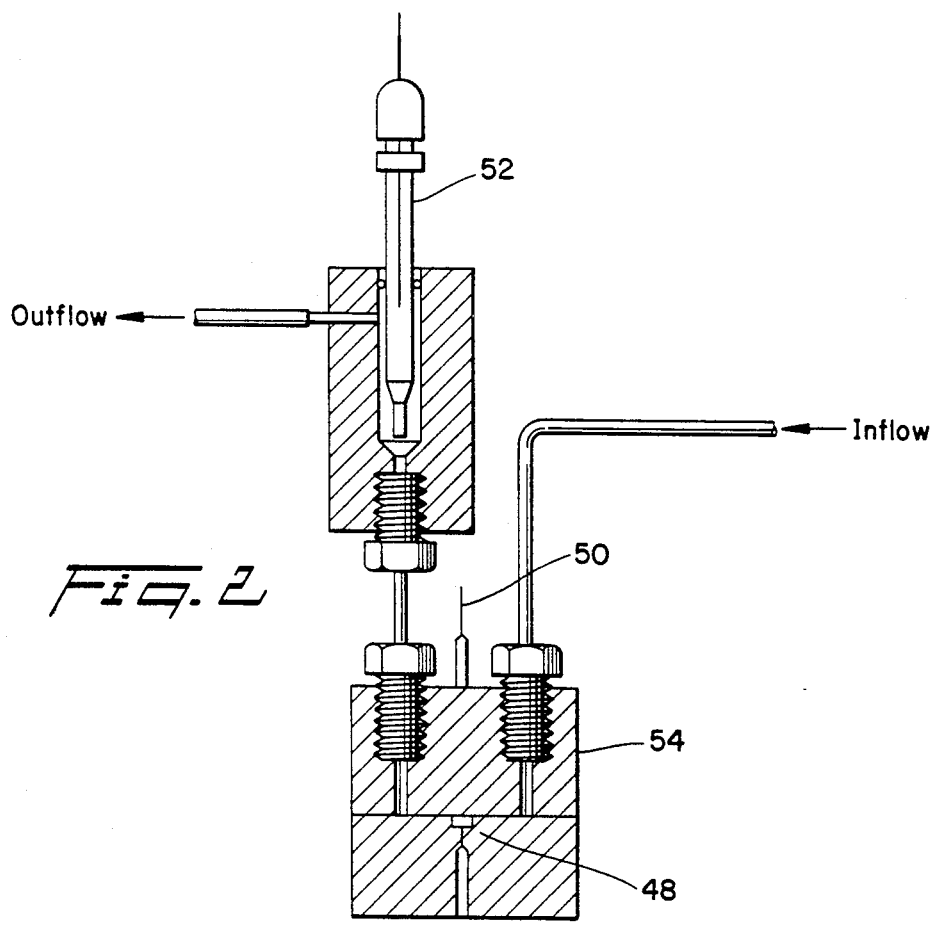
FIG. 2 is a cut-away view of the electrochemical detector cell.

A cut-away view of the electrochemical detector 22 is shown in FIG. 2. A voltage is applied to working electrode 48 which measures the potential of the flowstream relative to auxiliary electrode 50 and reference electrode 52. The working electrode assembly includes a stainless steel top 54.

The primary modifications to the HPLC-ECD equipment include (1) choice of column, (2) composition of the mobile phase, (3) choice of operating potential, (4) maintenance of the cell and column, and (5) treatment of associated equipment and supplies. Each one of these will be considered from the point of view of the technical specifications of the piece of equipment being discussed and what must be done to it on that basis. Additionally, the validations of any modifications made (in other words, the proof of the validity of the alteration and its purpose to the assay) will be set forth in the form of validation experiments, demonstration of detector cell sensitivity and of a stabilized baseline.

Much of the refinement of CA assay protocols as defined herein has come from the discovery of how to optimize the separation conditions (chromatographic aspects of the assay) and how to achieve and maintain a high level of sensitivity of the detector cell. At the practical level, these factors add up to an ability to control baseline noise. It is this baseline stabilization and reduction of baseline noise which is the essence of the uniqueness of the invention.

ASSAY ELEMENTS

The necessity to work at one nano-amp (or less) full-scale deflection as defined above, on a regular basis is what imposes the incredible difficulties on the CA assay procedure and the continued attention to the state of the baseline. The reduction in baseline noise, as discussed above and effected by the modifications made to the HPLC-ECD system described herein, allows the system to be maintained at a high level of sensitivity. The issue of baseline noise is also the basis for the 2:1 signal to noise ratio requirement which is believed to be the minimum-sized signal which can be expected to yield reliable data. A more desirable signal:noise ratio would be 5:1 or better.

Good results can be achieved if experimental protocols are closely followed and independent variables are managed as completely as possible. This is usually the case when advanced technologies are employed and CA assays are no exception to this limitation.

The goal of any CA assay is specificity, efficiency, reproducibility, reliability and sensitivity. In the case of HPLC-ECD assays, each stage of the analysis procedure must be optimized so as to not only intensify the final signal on the chromatogram from the CAs, but also to minimize extraneous inteference. The most fundamental aspects of the HPLC-ECD, CA assay are: extraction of CAs from plasma; separation of individual CAs bY HPLC; detection of CAs by ECD; recording of data and quantitation of results; and maintenance of the quality of the techniques used and of the HPLC-ECD apparatus and associated equipment. Each of these will be dealt with in turn.

BORIC ACID EXTRACTION

It will be apparent from the foregoing that a boric acid extraction technique for removing CAs from plasma is preferred. This method is highly reproducible, very quick and simple to perform and offers very high recovery of CAs. The fact that this extraction technique requires two millilitres of plasma is not considered a significant drawback to this method in light of these other factors. The method of Smedes et al [J. Chr. 231:25-39, 1982.] is employed with the sole modification being the use of deoxyepinephrine (DOE) as the internal standard instead of DHBA (dihydroxybenzylamine). In the present chromatographic system, the retention time of the DHBA peak interferes with the elution of NA and A and therefore, an alternative internal standard compound had to be found. DOE elutes shortly after the dopamine peak and thus does not hinder the separation of the other CAs. Use of this standard compound minimizes the length of the chromatogram and thereby reduces the dangers of peak spreading which would occur if any other compound with a prolonged retention time was employed. This internal standard compound (DOE) is preferred but not defined or n-methylepinephrine could also be used.

Figure 4:
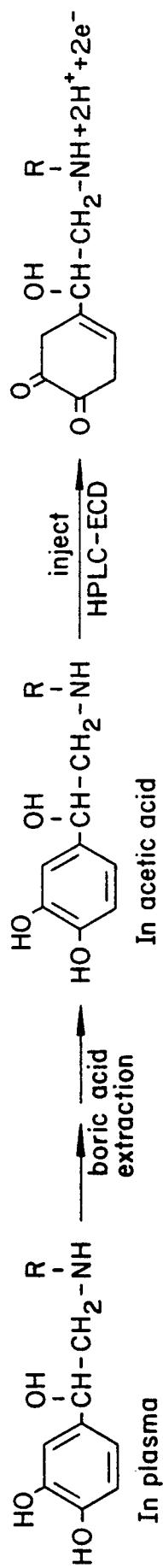
FIG. 4 is a schematic representation of the catecholamine extraction technique of the present invention.

The boric acid extraction technique is very straightforward to carry out. [See FIG. 4 for a schematic representation of CA extraction technique 12.] A solution is prepared, in aqueous alkaline medium, containing diphenylborate (available commercially as diphenylborate ethanolamine, or DPBEA); on contact with plasma, the negatively charged diphenylborate molecule forms a stable complex with the diol group on the CA molecule. To extract this complex out of the plasma, an ion-pairing agent (such as tetraoctylammonium bromide, or TOABr) is introduced; the ion-pairing agent is carried in an organic solvent (e.g. octanol and hexane) which lifts the ion-pair-CA-borate complex out of the plasma-aqueous mixture. This mixture is shaken for a few minutes to ensure that the reaction has gone to completion. This can be accomplished in a reciprocating utility shaker fitted with a utility carrier capable of accommodating a rack of culture tubes positioned horizontally. A suitable unit is commercially available from Eberbach [Eberbach Corporation, Ann Arbor, Mich. 48103] as a 2-speed model (180 or 280 excursions per minute) with an 124-watt (1/6 horsepower) motor.

The solvent phase is separated from the plasma-aqueous phase by centrifugation. The complex-containing solvent phase is then washed with more organic solvent (e.g., octanol) to dissociate the CAs away from both the ion-pairing agent and the borate. To extract the CAs away from the solvent and into a medium suitable for injection into the HPLC-ECD apparatus, a weak acid solution is added to this mixture. Once again, the mixture is shaken for a couple of minutes to ensure that the reaction has gone to completion. The phases are subsequently centrifuged away from each other. The resulting aqueous phase (i.e., the weak acid solution) contains free CAs and is suitable for injection into the HPLC-ECD apparatus.

The preferred diphenylborate derivative is commercially available as diphenylborate ethanolamine (DPBEA). DPBEA of the required purity is available from Aldrich [Aldrich Chemical Company Inc., Milwaukee, Wis. 53233.]. It is carried into the extraction procedure in a solution of ammonium hydroxideammonium chloride containing EDTA. Ammonium chloride and ammonium hydroxide are the preferred components of the aqueous alkaline mixture and are available from BDH Chemical Ltd. in the required level of purity [NH4Cl as BDH Assured Grade], and from Fisher [NH4OH as Fisher Reagent A.C.S. Grade, Fisher Scientific Co., Toronto, Canada ]. EDTA of the required level of purity is available from BDH Chemical Ltd. [as BDH Assured, ACS Grade, BDH Chemical Ltd, Toronto, Canada].

The preferred ion-pairing agent is TOABr. It is carried in a solution that is a mixture of heptane and octanol in the following proportions: n-heptane with 1% n-octanol containing 0.25% (w/v) TOABr. TOABr of the required purity is available from Fluka [Fluka Chemical Corp., Ronkonkoma N.Y. 11779.]. The purpose of the organic solvents is to stabilize the equilibrium of the TOABr and TOABr-CA complexes so as to optimize the extraction of CAs from plasma as opposed to interfering substances; this can best be accomplished by the use of very nonpolar solvents. The mixture of heptane and octanol proposed herein provides the best distribution coefficient of the CAs in a solvent mixture. Heptane of the required purity is commercially available from BDH Chemical Ltd. [BDH Assured Grade, BDH, Poole, G.B.].

Unfortunately, it is difficult to obtain octanol of the required level of purity. Therefore, octanol with as high a level of purity as is available [i.e. BDH G.P.R. Grade n-octanol from BDH, Poole, England] is purchased and purified further in the laboratory. The procedure is as follows: In a separatory funnel in a 1:4 ratio of washsolution:octanol (typically 50 mL:200 mL, wash:octanol), the following sequence of solutions is shaken with the octanol for about two minutes at each step; the phases are allowed to settle away from each other, and the aqueous phase is discarded each time: 1 N sodium hydroxide is shaken with the octanol, three times, consecutively; ultrapure water is shaken with the octanol, three times, consecutively; 1 N nitric acid is shaken with the octanol, three times, consecutively; and finally, ultrapure water is shaken with the octanol three times, consecutively. At the end of the procedure, the octanol is filtered through paper to remove any remaining traces of the washing solutions. This procedure requires one day to proceed to completion and the resulting octanol is stable for up to eight months on the shelf, at room temperature, in a clean, amber glass bottle.

The final solution step of the extraction technique yields the CAs in a medium suitable for injection into the HPLC-ECD apparatus. The preferred carrier solution is dilute acetic acid. Acetic acid of the required level of purity is commercially available from BDH Chemical Ltd. [as Aristar Grade, Acetic Acid, BDH, Poole, England.]. The water that the acetic acid solution is diluted in must be ultrapure, Type I Reagent Grade water, with a minimum resistivity of at least 18 M$\Omega$. A distillation apparatus capable of creating Type I water is commercially available from, inter alia, Millipore. The purity level of the acetic acid and the water in which it is diluted in is the main determinant of the size of the solvent front on the chromatogram. The acetic acid solution is membrane-filtered (e.g., 0.22 $\mu$ pore-size membrane) prior to its use in the extraction procedure because it will be injected directly into the apparatus. Because the NA is the first CA to come out of the preferred column and its peak is, therefore, relatively close to the solvent front, it can be obliterated by a broad solvent front.

The microsyringe which is used to transfer the sample into the HPLC-ECD system is normally made of glass and fitted with a metal plunger (sometimes tipped with Teflon) and a specially adapted needle. It is preferred that the plunger be stabilized with an extended metal handle: this adaptation not only improves the accuracy and reproducibility of the injections but also prevents contamination of the barrel of the syringe interior and does not permit heat from the operator's hand to be transferred to the contents of the syringe. The syringe must be calibrated at regular intervals to ensure that the volume delivered is accurate. It is recommended that a number of such units (with replaceable needles) of varying sizes (e.g., 25-, 50- and 100 $\mu$L maximum delivery volumes) be maintained in the laboratory. Suitable microsyringes are available from, inter alia, Hamilton Syringe Company [Reno, Nev. 89510].

CHROMATOGRAPHIC SEPARATION

Once the CAs have been isolated and concentrated from plasma, they must then be separated from each other in the HPLC apparatus. Reversed-phase columns are the preferred vehicle for separating the CAs; of these, the microparticulate bonded Phenyl column is most preferred. The exact basis for interaction of the column with the CA molecule is not precisely known. While the invention is not to be so limited, it is presumed that there occur interactions of the planar or $\pi$ electron cloud of the phenyl ring of the column with the ring of the CA, probably with the assistance of ion-pair formation with a counterion in the mobile phase. The phenyl column behaves similar to a $C_8$ column because of the juxtaposition of the benzene ring relative to the silicone support base. A reversed-phase, irregular microparticulate (10 $\mu$) silica bonded phenyl column is available through, inter alia, Waters Chromatography Division.

Based on the choice of column and detector in the present instance, a mobile phase of the following constituents is highly preferred: 70 mM sodium phosphate buffer, pH 4.8; 1 mM ethyldiaminetetraacetic acid (EDTA); 5 mM heptanesulfonate (HSA); and 5% (v/v) methanol.

The water which provides the basic framework for the mobile phase must be of the highest purity available. The preferred water for use in the assay of the invention is known as Type I Reagent Grade Water and is created by a filtration system which removes heavy metal ions, minerals, organic materials (including bacteria) and all dissolved particles on special cartridges. [For a more detailed discussion of Type I Reagent Grade Water, the reader is referred to NCCLS Document C3-P2, 1985.] Preferably, the filtration system has four or five replaceable cartridges and a final membrane filter (fitted with a series of 0.45 $\mu$ membranes placed in a sandwich configuration) which effectively sterilizes the effluent. The water which ensues has a minimum resistivity of 10 M$\Omega$, with at least 18 M$\Omega$ being highly preferred (a resistivity of 18.6 M$\Omega$ or better is ideal). A number of companies manufacture such water purification systems, notably Millipore and Barnstead (a division of Sybron). Analysis of the column effluent for water purity should be performed on a regular basis (e.g., monthly). Such an analysis can be obtained, for example, from Barnstead.

In the case of the buffer, there are a number of options in the choice of the buffering agent to be used to maintain the pH of the mobile phase at the desired acidity; such agents include acetate or citrate, with sodium phosphate being preferred. Specifically, mono- and di-basic sodium phosphate buffer made by BDH (Assured Grade, BDH Chemicals Ltd., Toronto), can be used. It is of critical importance that the solutions of acids and bases which are used to adjust the pH of the buffer are also made from high-purity reagents and ultra-pure water. It is assumed that the standard solutions which are used to calibrate the pH meter are as accurate as possible.

The preferred pH for this column is from about 3.5 to about 5.5, with pH of approximately 4.8 being highly preferred under the chromatographic conditions specified herein.

A chelator such as EDTA (ethylenediaminetetraacetic acid) is used to remove heavy metal ions from the system. EDTA is preferred over EGTA because it binds most metal ions (except calcium) better than EGTA does. The cumulative effect of this intervention is an improved baseline and diminished solvent front on the chromatogram. EDTA of the required level of purity is commercially available from BDH Chemical Ltd. [as BDH Assured Grade, BDH, Toronto, Canada]. It is preferred that the level of impurities be maintained at the parts per billion (ppb) level as opposed to the parts per million (ppm) range.

The use of a sulfonate such as heptane sulfonate (HSA) in the mobile phase is necessitated by the CAs themselves and their need for an ion-pairing agent to be used in conjunction with the column. [An alternative would be octylsulfonate.] In the present instance, heptane sulfonate is preferred. Generally, sulfonates which can be used include alky sulfonates having from 4 to 14 carbon atoms. HSA of the required purity can be obtained from Kodak [Laboratory and Research Products Division, Eastman Kodak Company, Rochester, N.Y. 14650.]. It is preferred that the level of impurities present in the material be maintained in the ppb range as opposed to ppm.

The purpose of the sulfonate is to increase the retention of the CAs by the column but not so much as to broaden the peaks unduly. There is a trade-off between retention (and separation) of the peaks versus splaying them. For calculation and reproducibility purposes, the sharper the peaks are, the better. If they are sharp, their height or area can be calculated more precisely and reproduced more easily. Through the use of HSA at a concentration of 5 mM, an added benefit is obtained in that the HSA "scrubs" the detector cell and keeps it and the column clear of any large fatty acids which may have escaped the extraction procedure and the filtration systems surrounding the column.

Finally, it is necessary to have methanol (acetonitrile is an alternative) in the mobile phase partly to counteract the ion-pairing agent (i.e., to diminish peak spreading) and partly to speed up the entire chromatography. An added bonus is that this organic solvent will also, tonically, "scrub" the entire HPLC-ECD system. Methanol of a purity of at least HPLC-grade is suitable for the present invention and can be obtained from BDH (OMNISOLV grade). It is preferred that the level of impurities present in the methanol be restricted to the ppb range (no more than 5 ppb is preferred).

It is emphasized that the conditions described above are most useful for the separation of adrenaline, noradrenaline and dopamine. If it is desired to separate any other CAs (or compounds of similar structure, e.g., drugs) by this system, the concentrations of the constituents of the mobile phase may have to be altered slightly from those described herein.

Preferably, the complete mobile phase is made fresh daily from a series of concentrated solutions kept at 4° C. and made fresh on a weekly basis. Only a small amount (i.e., one liter) of mobile phase is made at one time, as required; immediately before use, it must be ultra-filtered (preferably through an 0.22 $\mu$ pore-sized membrane filter) and de-gassed (for at least fifteen minutes and preferably twenty). This is performed on glassware specifically designed for this purpose. Disposable membrane filters with a pore size of 0.22 $\mu$ are used [such as Millipore's GVWP04700]. The glass filtration assembly is known to those skilled in the art and is readily available commercially from, inter alia, Millipore Corporation [Bedford, Mass. 01730.].

Once the mobile phase is ready for use, it is put into the HPLC's solvent reservoir where it is maintained free of dissolved gases by continuous purging with helium or other inert gas. It is preferred that the solvent reservoir be connected to the gas tank by way of a flow regulator equipped with a filter designed to trap any water vapor that may have found its way into the gas tank. The mobile phase is then transferred into the HPLC system by tubing equipped, at the intake, with another filter ("solvent inlet filter") designed to prevent any particles, which may have been accidentally introduced into the reservoir, from entering the pump. The pump itself is fitted with a series of filters and pulse dampeners which further augment its function of delivering pulseless flow of pure (and particle-free) mobile phase to the column. The pump is set at a pre-determined flow rate and the system is considered to be "up" after the required equilibration period of time has elapsed. The optimal flow rate is determined on the basis of the degree of separation of compounds (seen as peaks on the chromatogram) of interest from each other and from the solvent front. In the present instance, the optimal flow rate was found to be 2.4 to 2.8 mL/min. (this depends, somewhat, on the age of the column).

DETECTION (AND QUANTIFICATION) OF CAS BY ECD

Once the chromatographic conditions have separated the CAs into respective bands, it is up to the electrochemical detector cell to detect the relative amount of each CA within these bands. By implication, high sensitivity of the cell must first be attained and subsequently, maintained. Realistically, among other factors, this will also translate into an ability to maintain baseline noise at a minimum level. Control of baseline noise can be established via chemical and electronic means. The conservation aspects of the optimal functioning of an established level of high sensitivity of the ECD will be discussed hereinafter. Here, the operation of the detector cell in the assay and in the HPLC system is described. The tactics described below are all aimed at reducing noise as the chief method of improving the signal-to-noise ratio of the apparatus.

From the chemical point of view, the use of ultrapure components in all solutions which will ultimately come into contact with the working electrode (WE) cannot be over-emphasized. Included in this area is the de-gassing of the MP and the maintenance of that state by continuously purging the reservoir with an inert gas. Contaminants and air will not only interfere with the baseline by ionizing in response to the electrical field and generating an undesired signal, but will also be deposited on the surface of the WE and passivate it thereby reducing its sensitivity, linearity, operating range and reproducibility. It is emphasized that this precaution (regarding contaminants) also applies to the constituents of the solutions which comprise the acids and bases used to adjust pH and clean the equipment, as well as those which provide the basis of solutions to be used in the extraction procedure and as part of the mobile phase.

The attainment of a satisfactory level of sensitivity within a given electrode configuration will also depend upon the inherent physical characteristics of the ECD. This includes the design of the detector cell, its components, ancillary structures such as the reference electrode and all attendant electronics. In the present instance, the preferred working electrode is made of glassy carbon in a thin-layer configuration with a reference (normally Ag/AgCl) and auxiliary electrode. The thin-layer compartment lies within a sandwich of Kel-F plastic and is created by a groove in a PTFE gasket which is 125 $\mu$ thick.

There are a number of modifications to conventional arrangements of ECD cell compartments and their electronic controls that can be used to augment the signal:noise ratio. Improvements which can be made to the detector cell in an effort to reduce noise include the following: It is recommended that a stainless steel top be used for the WE sandwich compartment; this permits improved grounding of the electrochemical cell better than is possible if the sandwich were made of plastic.

Secondly, it is preferred that the thin-layer compartment be as small as possible (i.e., internal volume 10 $\mu$L or less). Because of the physical restrictions imposed by the HPLC system on the possible configurations of arrangements of the electrodes in the flowstream of the column effluent, the possible modifications to the electrode compartment will also be finite. This problem can be overcome by the use of a thinner gasket between the two halves of the WE compartment (i.e., a 50 $\mu$ PTFE spacer as opposed to an 125 $\mu$ one) and the use of narrow bore tubing connectors on the inlet and outlet aspects of the compartment. This provides the added benefit of reducing peak spreading and tailing, and system dead volume.

Third, it is preferred that the Ag/AgCl reference electrode be filled with a gel of these standards rather than an aqueous solution since the gels are believed to be more stable. [See FIG. 2.]

Improvements which can be made to the electronic controls of the ECD include the recommendation that the electronic controls be fitted with all electronic components which could possibly contribute to the reduction of noise generated by fundamental (including Johnson and shot noise) and non-fundamental (including excess noise) sources and which is ultimately represented as baseline noise and offset on the recording of the HPLC-ECD system. This includes the use of high quality resistors (with a $\leq 1.0\%$ tolerance thereby reducing the amount of fundamental noise); and, the use of 3-pole Butterworth instead of conventional RC-low pass filters (the so-called, "active filter kit") to control for the randomly varying input, analog signal. These modifications have a significant effect on the amount of baseline noise incurred by the system and markedly increase the stability of the cell during its operation.

An electrochemical detector cell assembly and appropriate electronic controls is available from, inter alia, Bioanalytical Systems (BAS).

To permit the cell to function optimally, it is very important to isolate it from stray electrical and magnetic interference. [Ref.: Plotsky, Gibbs and Neill, Endocrinology 102(6):1887-1894, 1978.] This is the purpose for utilizing a large Faraday cage to surround the injector, the column, the cell, its electronic control box, and the waste container. This provides electrical isolation from stray (electromagnetic) impulses in the room which houses the equipment. It is of critical importance that the entire system be properly grounded. Each instrument must be connected to a common ground point by a shielded cable. To prevent a ground loop from developing between the instruments and the large Faraday cage, electrical isolation platforms (e.g., made of lucite) must be placed under the injector, the cell's electronics and the waste container within the large Faraday cage. The power lines supplying the entire HPLC-ECD system must be isolated, protected and properly grounded. It is recommended that an uninterruptable power supply (UPS) be used as the main power source for this equipment.

Because of the extraordinary sensitivity of the ECD cell during operation at 1 nA or less, it has also been found advantageous to use incandescent instead of fluorescent lighting in the room in which the apparatus is located while operating the apparatus in order to further stabilize the baseline by eliminating the additional input of the 60 cycles/sec generated by the fluorescent light fixtures. It was also observed that the cell functioned best when the temperature of the room was maintained below 72° F. At higher temperatures, the baseline noise increased dramatically. Additionally, the level of humidity in the laboratory should be maintained between 30 and 60%. The electromagnetic micro-environment surrounding the ECD is an important contributor to its function at 1 nA or less F.S.D. Care should also be taken to see to it that the cell is not positioned in the path of an air-conditioner as this can also adversely affect its function. It is anticipated that these latter four problems will disappear in the next few years as improvements are made to the design and materials which make up the detector cell.

Figure 6:
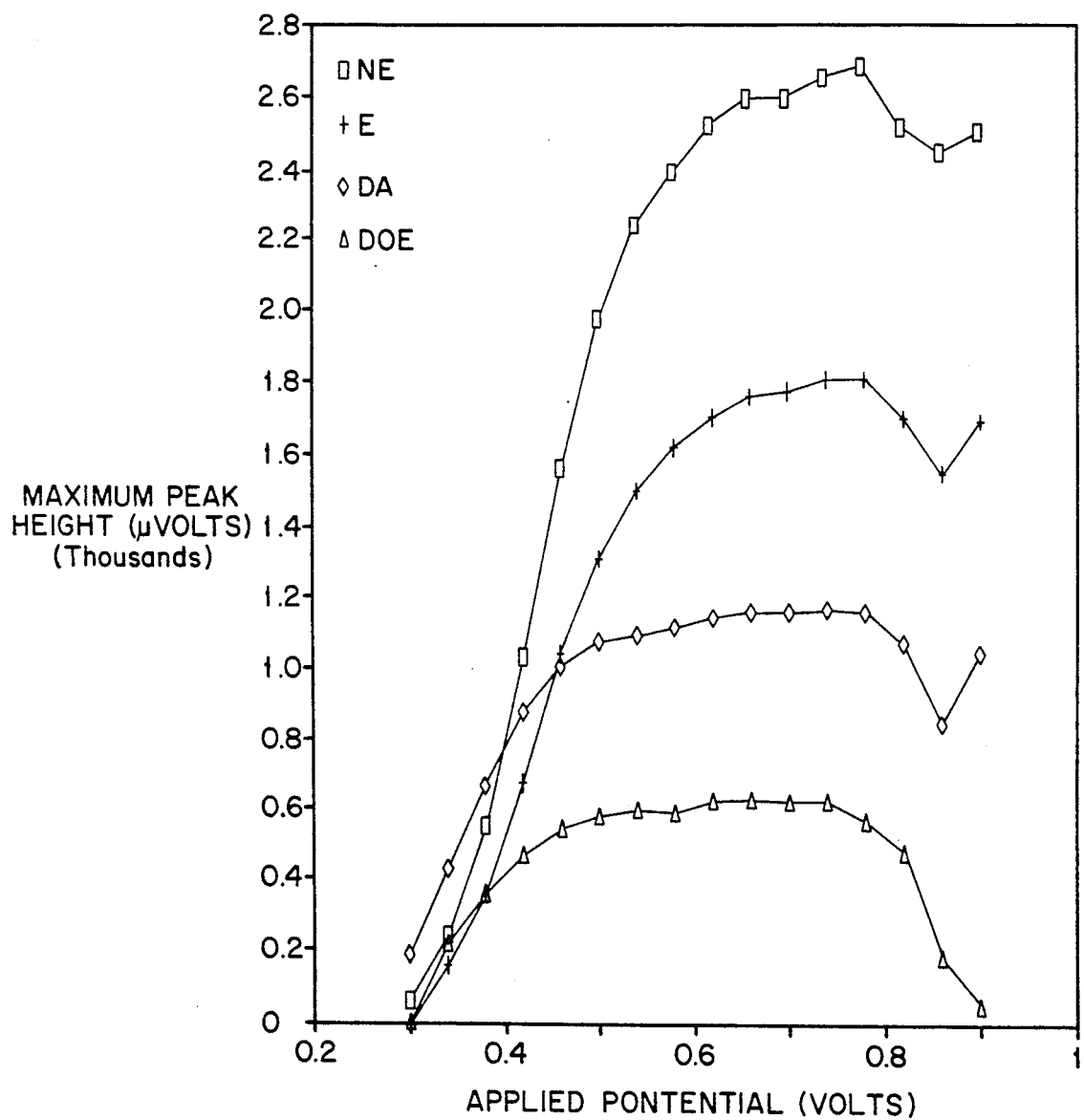
FIG. 6 is a polarogram representing the basis for the selection of the applied or operating potential of the electrochemical detector for the optimum detection of catecholamines under the present chromatographic conditions.
Figure 7A:
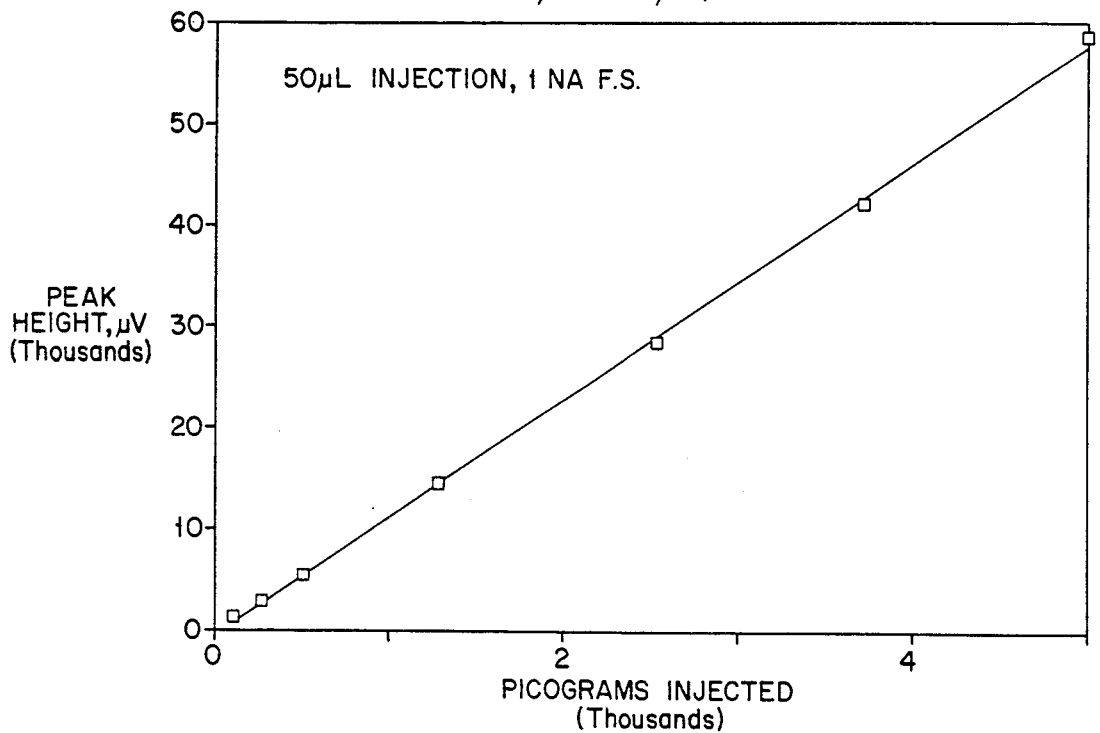
FIG. 7A is an example of a standard curve for norepinephrine.
Figure 7B:
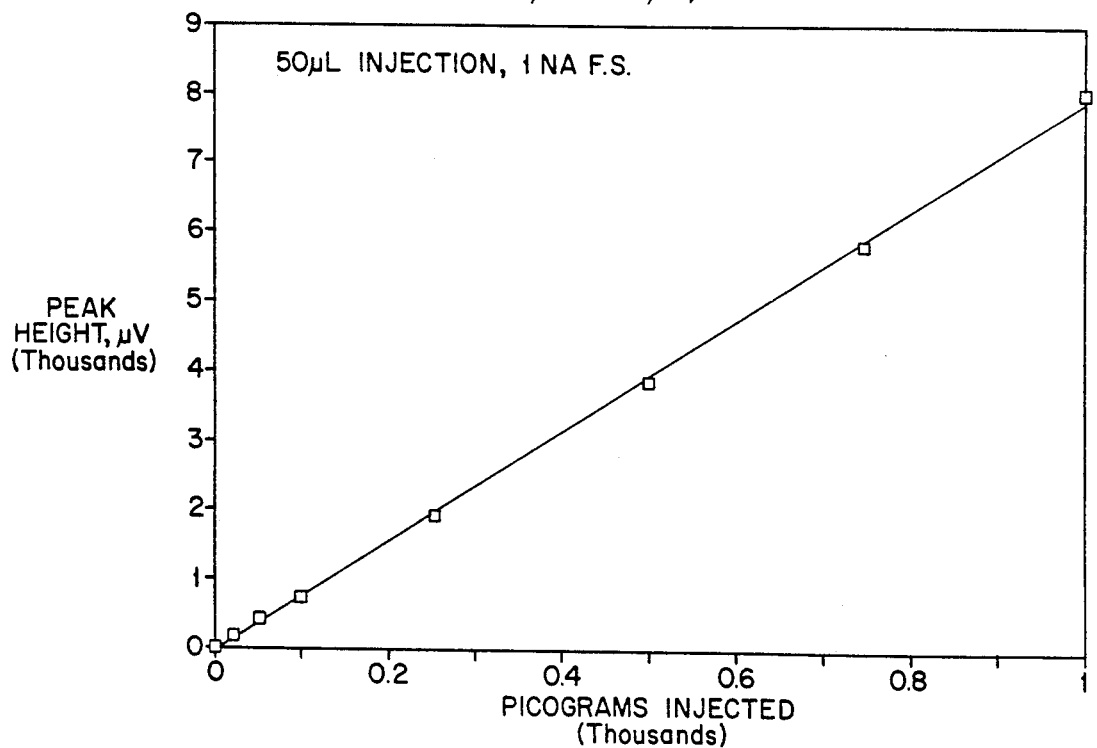
FIG. 7B is an example of a standard curve for epinephrine.
Figure 7C:
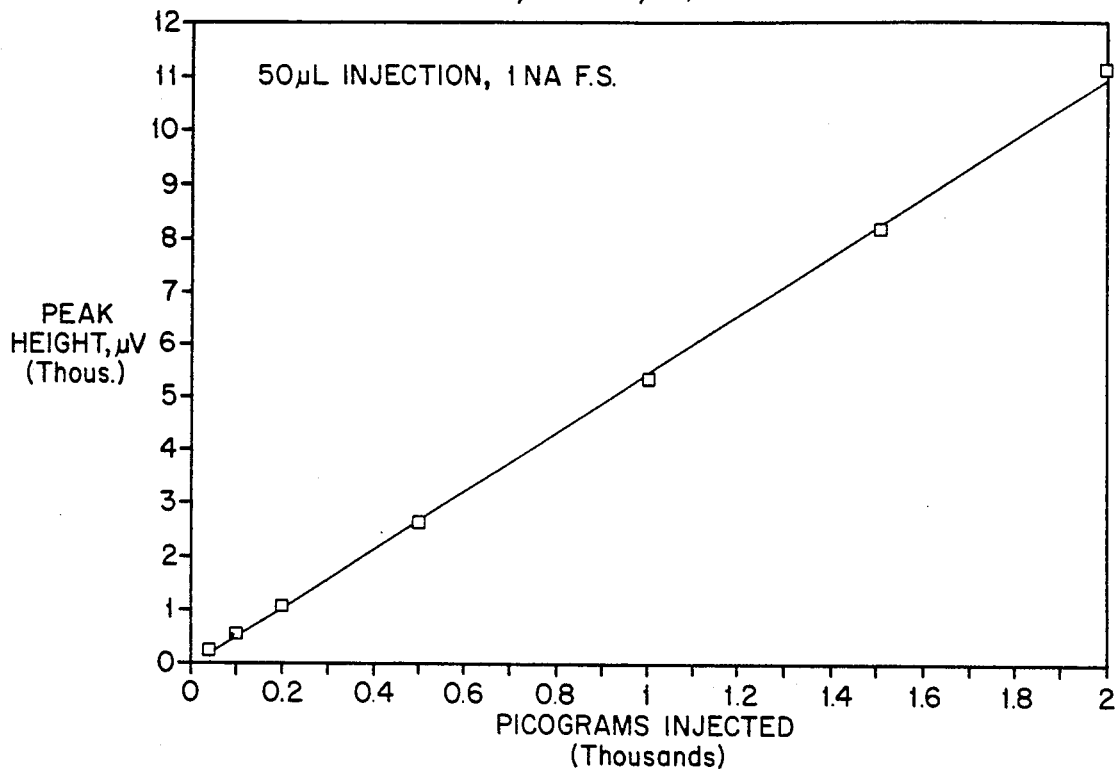
FIG. 7C is an example of a standard curve for dopamine.
Figure 7D:
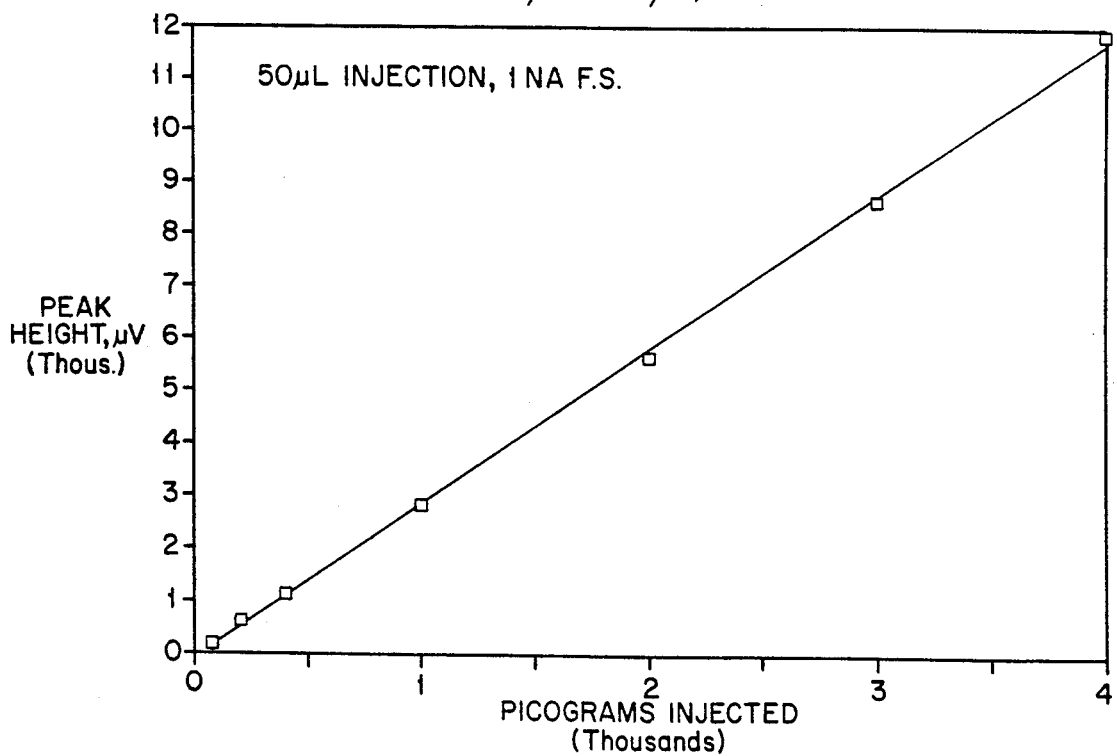
FIG. 7D is an example of a standard curve for deoxyepinephrine (the internal standard used in the assay described herein). These data were obtained from the injection of standard solutions, of varying concentrations, of these compounds.

The exact voltage to be used to obtain maximum oxidation of the analates under the current set of chromatographic operating conditions must be determined. It is emphasized that whenever the chromatography conditions are significantly altered, the optimum operating potential of the electrochemical detector for the analates of interest will also be changed. Optimum operating potentials of the ECD cell are determined by performing hydrodynamic voltammographic studies on the compounds of interest, as follows:

Since it is known that CAs will oxidize to orthoquinones, it is also known that the applied voltage should be positive (as opposed to negative). The HPLC system is set to run at some intermediate speed (say, 2 mL/min.) and the voltage of the cell is set at +0.20 Volts. A standard injection (of, for example, 50 $\mu$L) of a mixture of the CAs of interest, each CA being present in equal proportion, for example, 1000 pg each of NA, A, DA and the internal standard, deoxyepinephrine (DOE) is then made onto the column. Predictably, at +0.20 V there is no response from the CAs and the strip chart recorder tracing (i.e. the chromatogram) will only reveal a small solvent front peak followed by a flat baseline, indicating that no oxidation of the CAs is taking place on the working electrode surface. The voltage is increased in steady increments of, for example, 0.02 or 0.04 V each time, while repeated injections of the standard solution are made. As the voltage is increased, the current response of the CAs also increases until a plateau is reached. On the output of the strip chart recorder, there is observed a series of peaks of ever-increasing height as the voltage is stepped up. But, because each of the CAs has separate physicochemical properties, the height of these peaks changes at a different rate for each molecule. The procedure is stopped at about +0.9 V. A graphic plot is made of the response of each CA (in terms of current) to the applied voltage and the final plot (polarogram) is constructed. FIG. 6 is an example of a polarogram. A dedicated integrator is connected in parallel with a strip chart recorder and the output from the integrator, in $\mu$V, can be used to plot the polarograms. Under the operating conditions described herein, the retention times for NA, A, DA and DOE are about 2.4, 3.4, 5.5 and 7.8 minutes, respectively.

Creating a polarogram is necessary prior to using the system for any analysis. Preferably, the polarogram is performed with very small quantities of CAs. For example, from about 1000 to about 2000 pg of each CA are injected onto the column. Such a small amount of CA is representative of that normally encountered in vivo and, as such, is more realistic in terms of actual operating conditions than would be the use of larger amounts of CAs, despite the fact that the latter might give more sharply defined peaks. It is preferred that the compounds used to make up the CA standard solutions be purchased from Calbiochem-Behring, Division of American Hoechst Corporation, La Jolla, Calif. 92037. It is essential that the CA standards be of the highest available purity, containing neither interfering nor inert contaminants. It has been found that the shelf-life of the CA powders is only six months from the date of manufacture.

Working within the biologically significant concentration region is, in fact, an imperative if the HPLC-ECD equipment is to be of any advantage to an assay. For example, the present use of 1000 picograms of each CA with the range switch of the ECD set at 5 nA is less than one-tenth what has heretofore been used in studies reported in the literature; i.e., most HPLC-ECD assays report a polarogram determined using 10 nanograms of each CA. This latter amount does not represent what is found in real life since humans could never have such high plasma CA levels. Consequently, the ECD would never be required to perform at 10 nA F.S.D. and the utility of demonstrated function in this concentration range is very limited. The only exception to this rule is tissue measurements of CA levels which are in the nanogram region and require higher range settings on the ECD. However, these latter measurements present no methodological challenge because of the high concentrations of CAs involved. Therefore, if one wishes to establish the performance of a system in the more difficult analysis of plasma CAs, one must use representative concentrations to calibrate the machinery.

The usefulness of showing a measurement obtained in an unrealistic concentration range is of limited significance. The reason for the use of such high concentrations of CAs in the past, however, has been simply that heretofore it has not been possible for technical and other reasons to measure physiological, low resting levels of CAs on a routine basis. Furthermore, it is easier to justify an assay technique by obtaining clear data from high concentrations of standards. However, such data have limited applicability to the conditions of the assay as required to quantify resting concentrations of human plasma CAs.

The use of a range setting of 5 nA F.S.D. for the polarogram experiment is one of the lowest heretofore used. It is generally not possible to go any lower than this (e.g., 1 nA) and still use reasonable, i.e., physiological, concentrations of CAs because the peaks become very high and go off-scale. And, as explained above, to go much higher than the physiologically relevant concentration range of CAs is pointless.

While a strip chart recorder connected from the output of the ECD can be used in parallel with an integrator, as described above, the data in the present instance are actually analyzed from the integrator print-out of peak height. This is preferred because it provides an objective measure of peak height that is also independent of the size of the paper used in the recorder (thereby effectively eliminating another source of error). Furthermore, in the digital recording, one has a permanent record of the chromatogram and can re-analyze it as necessary. The strip chart recorder's role is that of a back-up to the integrator in case of a machine-failure or partial power interruption and as an adjunct piece of information to the integrated picture of the chromatographic events that are provided by the integrator. Because the information that the integrator uses is so specific, and has already been electronically integrated (i.e., from an analog to a digital signal), it does not represent "raw data" per se. However, to monitor and control the chromatographic conditions, the "raw data" should be known and represented in real-time.

It must be re-emphasized that integration of peaks on the chromatogram is not a substitute for their separation on the column; samples not properly separated by the column cannot be separated mathematically and still retain validity as data.

The preferred integrator is a Shimadzu C-R5A [the C-R3A is an alternative]. As far as can be ascertained, this particular integrator is the only one currently readily available having the ability to subtract one chromatogram from another. Other integrators having this feature will be equally suitable as they become available. This means that baseline noise can be removed by subtraction of a suitable, control chromatogram from the chromatogram of the run to be analyzed. In the analysis of CAs, this can greatly assist the interpretation of the data collected during research and development (R&D) studies on the assay method by demonstrating the exact source of "junk" peaks. For example, if the baseline chromatogram contains a peak that interferes with one of the CA peaks, it is possible to trace the source of that extraneous peak by changing the composition and/or characteristics of the solution which is being injected. In fact, it is possible to produce a library of such knowledge which is then available as a reference during research activities when unknown plasma samples are being run through the HPLC-ECD system.

SUMMARY OF MAINTENANCE PROCEDURES

Maintenance of the apparatus of the invention is central to the invention as a whole. This maintenance is critical from the standpoint of both reliability and reproducibility of these assays of plasma CAs. While a variety of maintenance techniques and procedures are known, there has heretofore been no coherent methodology for maintaining the plasma CA, HPLC-ECD system running for a prolonged period of time. Apparently innocuous sources of contamination are ultimately manifested as compromised functioning of the HPLC-ECD apparatus. For example: When operating at 1 nA or less F.S.D., the impurities in the mobile phase make a tremendous difference to the baseline noise. Any carry-over from the plasma extraction procedure can destroy the validity of chromatograms entirely. Another possibility is that the column might react with a drug that was given to the individual whose plasma is being analyzed. If this occurs, the column could be rendered incapable of separating the CAs. Alternatively, the detector cell might become passivated by the deposition of particles of unknown origin on its surface (i.e. surface of the working electrode) and thus be rendered insensitive.

There is also the requirement of maintaining the "steady-state" condition of the system; that is, if the entire system is functioning well except for some minor contamination problem, it would not be desirable to either shut it down completely to fix such a thing or to subject the system to a washing procedure which would interfere with normal function. Ideally, maintenance should be compatible with continued function at the desired sensitivity level. None of these issues have heretofore been fully addressed.

TREATMENT OF ASSOCIATED EQUIPMENT

Anything which comes into contact with the assay (and hence, ultimately the HPLC-ECD system) must be maintained scrupulously clean, dust-, lint- and fingerprint-free. In fact, it is preferred that the assay be performed in a laboratory dedicated to that analysis alone with equipment that will only be used in the CA assay. The term, "associated equipment", includes all glassware, plastic ware, tools, and supplies handled during the performance of the assay. In short, every component which will be used must be screened prior to its employment in this laboratory. Additionally, the vessels of the assay should not contribute chemical or particulate matter as a result of having been previously used for another purpose, for example, to contain a highly acidic solution. The glassware itself is thus preferably made of high quality, borosilicate glass. Furthermore, the glassware which holds the CA standard solutions, the solvents (and their repipettes) should be made of amber glass so as to protect the CAs, and the solvents, from degradation by light.

The operator of the CA assay must be vigilant in the laboratory because it is a simple matter for contaminants such as dust and lint to enter the apparatus. For example: when a solution is being transferred from one container to another, it is normally necessary to wipe off the tops of the bottles when the transfer is complete and before the bottles are re-covered. If a tissue is used which leaves a deposit of lint on the container, it is possible for that lint to end up in either the mobile phase reservoir or even be injected as part of the sample (if the solution being transferred happened to be the sample carrier solution). In this simple way, lint could be introduced into the HPLC-ECD system and quickly clog the microscopic filters. This would be manifest on the baseline as noise and erratic baseline signal due to an erratic flow rate. Again, at 1 nA, all such things are plainly exhibited.

Another example of a simple way to introduce a contaminant into the system is as follows: when the system is being repaired, i.e. when a filter is being replaced or when a leak is being fixed by filing the end of the stainless steel tubing to put on a new compression fitting, the system has been filled by methanol in a stepwise manner. Great care must be taken not to handle the ends of the cut tubing with bare fingers because compounds such as normal fatty acids or other chemicals from the fingertips may find their way into the system. Therefore, it is recommended that all such tasks be performed while wearing clean, disposable surgical/examination gloves (e.g., Tru-Touch) thus by-passing the possibility of the problem. The extraordinary sensitivity of the ECD at 1 nA or less F.S.D. demands such careful attention to details.

It will be obvious that this fingerprint issue is very far-reaching: a myriad of equipment parts are handled by the operator in the course of a day in a laboratory. For the purposes of the HPLC-ECD system running at 1 nA, it is imperative that all sources of contamination be eliminated. It is recommended that all tools (e.g., wrenches and files) which will be used on the parts of the apparatus during repairs are maintained grease-free and dedicated to this use only. This is easily accomplished by rinsing the paraphernalia with pure methanol and wiping (if necessary) with a lint-free tissue (e.g., Kim-Wipes). It is further recommended that all surfaces which will be used by the repair procedures or the components of the assay as it is being run, be maintained as clean and lint- and dust-free as possible. This can be accomplished by the use of plastic-coated bench covers which are replaced frequently.

All the glassware and plasticware which is destined to come into contact with any part of the active assay system must be cleaned prior to use. The following discussion will use glassware as the model but it is emphasized that the same procedure must be followed for all immersible and washable equipment which will come into contact with any part of the assay. It is reiterated that this is crucial because, for example, the extraction technique uses strong acids and bases to effect the extraction; any and all molecules present, from whatever source, will also be susceptible/available to this extraction technique. The purpose of the following procedures is to remove all residue from the inside (or contact) surface of the glassware.

The glassware is first subjected to an acid bath (e.g., dichromic-sulfuric acid mixture) to remove all residues from the surface of the glass. This is a standard, laboratory procedure. The glassware is then rinsed in copious quantities of water (preferably distilled) until all traces of the acid have disappeared. The glassware is then washed in an aqueous solution of a non-residue detergent [such as Hemo-Sol]; distilled water is preferred. It is preferred to allow the glassware to soak in these non-scrub detergents for at least two hours (preferably overnight) prior to rinsing the detergent away with copious quantities of water. Distilled water is preferred as the rinsing solution and double-distilled or de-ionized water is preferred for at least the final rinse prior to drying in an oven. The glassware is removed from the oven when it has dried and the tops of the containers are covered to maintain the interiors dust- and lint-free. Each piece of glassware is used only once and after use, it is placed back into the detergent washing solution where it undergoes the washing procedure again. The dichromic-sulfuric acid bath treatment is repeated as required (i.e. when a residue has built up on the contact surface of the glassware again).

Any glassware which will be used to extract the plasma, or transfer or store it, must be siliconized prior to use. That is, the glassware is given a mono-layer coating of silicone on its inside (or contact) surface to prevent the CAs from adhering to the glass. If plasma were allowed to come into contact with "bare" glass, a portion of the CAs contained therein would stick to it. In this event, the concentration of the CAs suspended in the plasma would be diminished unnecessarily. This is a simple source of error that can be readily avoided.

The siliconization can be carried out in the laboratory using a commercially prepared siliconizing solution (from, for example, Serva Feinbiochemica, Heidelberg, W. Ger.) or one can purchase the concentrate (e.g., dichlorodimethylsilane from MCB) and prepare the solution. It is even possible to purchase glassware already siliconized [from I-Chem Research, Hayward, Calif. 94545.]; however, it must be determined that such glassware is appropriate for the CA assay procedures. The glass tubes which are used to collect the blood from the patients and store it in the freezer are purchased pre-siliconized [from Becton Dickinson and Company, Lincoln Park, N.J. 07035]. Siliconizing glassware is a well-known procedure as described, for example, in General Electric's Application Document # AD 20-A.

Due to the harsh conditions of the extraction steps (e.g. 2N $NH_4OH$-$NH_4Cl$), the glassware must be re-siliconized after every use because the silicone layer is stripped by these conditions. It is not necessary to completely strip off the remaining layer prior to re-siliconization of the glassware but if it is desired to do so, this can be accomplished with an alcoholic potassium hydroxide solution [i.e. 25:25:50, (v/v/v) potassium hydroxide:water:ethanol, 95%].

It is recommended that the tubes which are used in the extraction of plasma procedure be 12-mL capacity borosilicate glass culture tubes with screw caps which have Teflon liners. The screw cap tops cannot be subjected to the acid-treatment recommended for the glassware; they must be rinsed well in distilled water and cleaned with pure methanol. The Teflon (polytetrafluoroethylene) does not bind to CAs; therefore, it is not necessary to siliconize the caps. These tubes are readily available commercially from, for example, Canlab [Division of Travenol Canada, Inc., Mississauga, Ontario L4V 1T7.].

MAINTENANCE OF HPLC APPARATUS

The goal of these maintenance and support procedures is to ensure that the apparatus does not add anything significant to the mobile phase by way of either particulate or chemical matter. This is also one of the reasons that the HPLC system is equipped with a series of stainless steel filters with microscopic pores, placed at regular intervals along the flowpath; the filters are specially designed to capture particulate matter. The question of chemical contamination is determined by a multiplicity of factors encompassing all the chemicals which ultimately come into contact with the apparatus, either directly or indirectly. The apparatus should not introduce electrical noise into the system; the apparatus should be maintained leak-free (for the pressure-path of the MP) because leaks are also a source of noise at 1 nA F.S.D.; and the flow through the system must be pulseless. This latter property is largely determined by the quality of the pump but is influenced by many other factors. Before it can be used for the purposes of the CA assay, it is essential that the apparatus be well grounded (discussed above). Regardless of the source of any problems, the maintenance and support procedures must be able to deal with it (i.e., eliminate it).

The basic procedure used to clean the entire flowpath within the HPLC-ECD system is instigated when one of the following occurs: (1) the sensitivity of the cell diminishes by 25% of the maximum attainable signal; (2) if the system suddenly becomes contaminated; (3) if the baseline noise experiences a dramatic and unexplained increase; (4) if any repairs or replacements have to be performed on the apparatus.

The flowpath is cleaned by passing a specified sequence of solutions through it. The sequence of solutions passed through the entire system (including the column and the cell) is as follows: normal mobile phase to pure water (the reference electrode is taken out at this point—it is only able to withstand a 25% methanol solution before it is damaged), then 50:50 (v/v) methanol:water and then pure methanol. Normally, about 150-200 mL of fluid are pumped through the apparatus at each step of the sequence. If necessary, any repairs to the mechanical parts of the system are performed and the detector cell is polished while the system is in pure methanol.

The parts of the pump that require regular changes include the in-line filters, the Teflon gaskets/seals at the back of the pump heads and the compression screws and ferrules on the tubing that join the tubing to the body of the pump. Occasionally, the check valves and pistons must be replaced as well. The pump head seals must be changed promptly, as required, e.g., at three month intervals. It is highly recommended that all new spare parts be sonicated in 50:50 (v/v) methanol:water for thirty seconds before being introduced into the system.

It is very important that none of the compression fittings leak. The integrity of these fittings is determined by two principal factors: the condition of the end of the tubing and the position of the ferrule on the end of the tube relative to the seat. If the end of the tubing is not cut perpendicularly, the tube cannot be seated properly; and, if the ferrule is not positioned at the correct height on the tube relative to the seat, the connection will not be sealed. The net result of both of these things is that the connection will leak; and leaks are manifested as baseline noise at 1 nA F.S.D. (partly because leaks disrupt laminar flow through the system, the flow of MP begins to pulse under these conditions).

The attainment of leak-free connections is facilitated by smooth, symmetrical, perpendicular cuts of the stainless steel tubing. It is preferred that the replacement tubing be purchased professionally pre-cut and the ends machine-polished, the edges (both inside and outside) having been deburred. Such tubing is commercially available from Rainin Instrument Company [Rainin Instrument Company Inc., Woburn, Mass. 01801-4628].

The correct placement of the ferrules is achieved as follows: When new tubing is being installed in the apparatus, the compression screw and the ferrule are placed on the tube in the correct juxtaposition. The compression screw and the ferrule are then held high on the tube while the end of the tube is guided into the seat. The tube is carefully positioned so that the end of the tube is flush with the seat (i.e. completely flat against it). The tubing is held firmly in this position while the ferrule is then allowed to fall down into the seat; it is followed by the compression screw. The assembly is held down firmly while mobile phase (i.e. methanol) is passed through the fitting to ensure that any accumulated air is washed away. With mobile phase flowing through, the fitting is progressively tightened until it stops leaking.

Care must be taken to ensure that fingerprints are not left on any part of the system which might come into contact with the mobile phase. It is of critical importance that the operator of the equipment wear gloves during the performance of any repairs to the system. Normally, by the time all repairs have been effected to the system, about 200 mL of methanol are put through the apparatus. When repairs have been completed, the sequence of wash solutions is repeated in reverse order: from pure methanol to 50:50 (v/v) methanol:water to pure water to mobile phase.

Once again, about 150-200 mL of each solution go through the system at each stage of the sequence; each solution is flushed through the system at the maximum pressure possible for the viscosity of the fluid. It must be borne in mind that, normally, the column cannot tolerate higher than 3500 psi without sustaining damage therefore, care must be taken to prevent a high pressure build-up in the system during the washing sequence. Practically speaking, the 50:50 (v/v) methanol:water solution has a very high viscosity and cannot be put through the system any faster than a rate of approximately 1.2 mL/min without risking damage to the chromatographic bed. Therefore, several hours are required to proceed through this wash sequence of solutions.

Once the HPLC-ECD system has arrived back at the mobile phase stage, the system must then be re-equilibrated. To reestablish a quiet baseline and a stable working electrode, the system must be run for 72 hours at, preferably, 500 psi before any injections are made. The sensitivity of the cell should be determined at the end of that time to affirm that the sensitivity has, in fact, been restored to its previous levels. By the use of the methanol wash, the assumption is made that all the contaminants present on the column, the cell and other parts of the apparatus (such as the filters) are soluble in methanol and will be removed by it. If more drastic cleaning needs to be done to the system, then the procedures outlined in detail elsewhere below must be used.

The methanol wash sequence, described above, is useful for most problems which occur with regularity.

Obviously, one of the most critical components of the HPLC-ECD apparatus is the column. Unless the best capabilities of the column are preserved, it cannot continue to separate the CAs from each other. For example, a reversed-phase column has a life-time of approximately 1200 injections in a normal clinical chemistry laboratory, under good care but not special treatment. In the inventor's experience, when used for CA assaying, these columns only function optimally for the duration of about 300 injections before they show signs of irreparable wear; and after 400 injections, the columns are completely useless. The key issue here is optimal performance of the column; the CA assay demands all components, especially the column, to function at their best on a continuous basis.

The state of the column is assessed by monitoring baseline noise and separation of the peaks on the chromatogram, as well as peak retention times.

The potential sources of contamination of the column include: (i) materials leached from the HPLC system itself, (the system is tonically subjected to an acidic mobile phase that is relatively corrosive), (ii) contaminant constituents of the mobile phase, (iii) compounds from the extraction procedures solutions which have continued through the extraction along with the CAs, and (iv) compounds in plasma which have survived the extraction technique and have come through the system to bind on the column.

If contaminants become deposited on the column, it seems that the only thing which can be used safely in an attempt to remove them is a methanol wash (described above). Due to the intense dependence of the separation of the CAs on the performance characteristics of the column, all other column regeneration techniques are ineffective. This is partly because excess manipulation of the column causes problems such as repacking of the bed, channel formation, dead space at the end of the column, and the like. Other treatments of the column may be too rough for the column integrity. Therefore, if a serious problem develops with the column, the column must be replaced by a new one. It must be appreciated that it is very easy to damage a column made up of 10 $\mu$ particles; at that size, simply bumping the column may cause disruption of the bed. [For these reasons, each column is an individual unto itself and if a column must be replaced, the performance characteristics of the new column must be determined before the new column can be utilized in the CA assay.]

The column is directly preceded by a short guard column (1 cm) designed to filter the mobile phase just before its arrival at the column. The guard column preferably contains an irregular microparticulate silica bonded $C_{18}$ matrix in special packaging designed for this site. Such a guard column is available from, for example, Waters Chromatography Division as a $\mu$Bondapak $C_{18}$ Guard-Pak. It is recommended that the guard column be replaced after every 50 injections (or as required). It is understood that this repair to the HPLC-ECD system, like all others, is performed with the apparatus running on pure methanol only (as opposed to mobile phase).

The appearance of an anomaly in the function of the HPLC-ECD apparatus can be diagnosed by a process of elimination that can only be gleaned from experience. However, because there are relatively few components to the HPLC-ECD system, problems and the attempt at their solution can readily be seen and repairs rapidly effected.

In order to keep the HPLC-ECD system running smoothly at 1 nA (or less) with a quiet baseline, it is necessary to adopt a protocol that will clean the system regularly yet allow it to continue to function. It must be appreciated that the mobile phase is flowing through the system at a rate of 2.8 mL/min. on a continuous basis; this solution has a pH of 4.8, and contains solvents and a detergent; therefore, the mobile phase will continually be eroding the apparatus and passivating the electrode, even if no injections have been made. Contaminants which may have been avoided by scrupulous attention to the constituents of the mobile phase will be created simply by the passage of the mobile phase through the system. Therefore, it is imperative that the entire HPLC-ECD system is subjected to regular "washing" on a daily, weekly and monthly, or bimonthly, schedule. The daily and weekly procedures are followed on a regular basis. The monthly cleaning technique is instigated as required. And, if serious contamination of the system were to occur, there are a number of things which can be done to the system in an effort to remove pollutants. Each of these techniques will be reviewed in turn.

The daily wash treatment is in the form of a special overnight mobile phase whose purpose is to preserve the integrity of the column by dealing immediately with deposited contaminants. The purpose behind the composition of the daily scrubbing solution is to achieve a fine balance between cleaning the system and not disrupting its function (i.e. permitting the cell to maintain high sensitivity and a low noise level). While instructions for a "washing mobile phase" are often included in repair courses on HPLC systems, the issue itself is not addressed in terms of the criticality of the solution composition nor in precise terms of what such solutions should comprise.

The point of this exercise is to make a scrubbing solution whose composition is similar enough to the basic mobile phase that the use of it will not alter the equilibrium condition of the electrode at 1 nA yet the solution will be able to clean the system. It is important to maintain the buffer normally used in the MP as the basic solution for this daily cleaning procedure so as to maintain the equilibrium condition of the ECD's electrodes. A buffer must be present (and be electroconductive) to allow proper operation of the working electrode. If the "cleaning mobile phase" were not electroconductive, there would be a long, re-equilibration period to go through before the cell could function normally once more. Valuable time would thus be wasted waiting for the cell to re-equilibrate and any advantage gained by the use of the overnight cleaning solution would be lost because continuing function of the HPLC-ECD system would have been disrupted.

One of two solutions can be used having the following composition: either a 70 mM sodium phosphate buffer, pH 4.8 with 5 mM HSA and 15% methanol, or the 70 mM sodium phosphate buffer, pH 4.8 with 0.5 mM HSA, 1 mM EDTA and 15% methanol. The choice of the two options is determined by the type of samples that were injected on that particular day. If standards were the principal samples injected on the day in question, then the latter overnight mobile phase is used; if the principal samples injected were extracts of plasma, then the former solution is used. The overnight mobile phase is run through the system with a pressure head of about 500 psi and therefore at a speed of about 0.5 mL/min.

Specifically, the "scrubbing" action is performed by the high methanol and HSA concentrations. The choice of concentrations used is not arbitrary: the reference electrode cannot tolerate higher than 25% methanol in the mobile phase without sustaining damage. As the methanol content of the overnight mobile phase approaches 25%, the re-equilibration time becomes more prolonged. The 15% chosen was decided on the basis of the fact that this concentration will have a significant effect on the contaminants in the system yet will not pull the working electrode so far away from its equilibrium point that it would take longer than one hour to re-establish the baseline at the start of a new day. The high concentration of HSA that is used has the additional benefit of removing any fatty acids which have come through the extraction procedure (from the plasma) and which could deposit themselves on the column and/or the glassy carbon electrode.

The problem of compounds surviving the extraction technique and contaminating the column and the detector cell surface is solved by either improving the extraction procedure itself (so as to ensure that nothing else but the CAs are taken from the plasma or are contributed by the extraction technique's components) or, if this is not possible, then the column is protected from the effects of these compounds. Once again, the guard-column and the overnight mobile phase are the principal solutions to these problems. For example, lipids and fatty acids escape through the extraction procedure and arrive and accumulate at the head of the column and on it. These are subsequently largely removed by the actions of the overnight mobile phase.

One aspect of the contamination issue which has received little or no attention is the problem of analyzing plasma from patients who are receiving a variety of drugs (as opposed to measuring CAs in plasma from healthy subjects). If plasma is essentially drug-free, then it is not necessary to consider whether the drugs can pass through the extraction procedure, how the column will deal with such drugs, or whether the cell will be affected by them. If, however, the plasma is not drug-free, then the effect, if any, on the assay (and the HPLC-ECD system) must be determined.

At the end of every week, the pump and injector (but not the column and the cell) are flushed with the following sequence of solutions: 50 mL pure water, 50 mL 50:50, water:methanol (v/v), 50 mL pure methanol, then 50 mL water:methanol mixture again, and 50 mL pure water before changing to the overnight mobile phase for the weekend. If particularly complex plasmas have been extracted and injected during any work session, this procedure is done at the end of the day as well as on a typical Friday afternoon. In this case, several injections of pure methanol (pre-filtered through the 0.22 $\mu$ membrane and de-gassed) would first be made in an attempt to clear the column of the contaminants.

In some cases, the HPLC-ECD system may be more seriously contaminated. If the serious contaminant is in the pump or injector, then the system must be purged with a solution of nitric acid. Alternatively, if the HPLC-ECD system has been sitting unused, in methanol, for an extended period of time (such as six months), before it can be re-started, it is advisable to purge the pump and injector with nitric acid. Another possibility is that a serious contaminant may have inadvertently entered the system from the mobile phase reservoir or from a particularly complex sample. In the latter case, if compounds have bound to the column, only methanol should be used in the attempt to wash them away. It has been found that many drugs commonly given to patients in hospital can bind, effectively irreversibly to the column and in this case, the column cannot be rejuvenated and must be replaced. However, a proportion of these same compounds may also be deposited on the electrode and will diminish its sensitivity considerably. If the diamond polishing technique (described below) is not effective in restoring the sensitivity of the cell, the cell too can be subjected to the nitric acid treatment. The column, of course, would be completely destroyed by nitric acid and must be by-passed during such a procedure.

For the nitric acid wash, the sequence of cleaning solutions is: mobile phase to pure water, followed by disconnecting the column because the nitric acid would destroy it. About 100 mL of a 6 N solution of nitric acid is passed through the pump and injector. Pure nitric acid which has been diluted in ultrapure water is used because it serves no purpose to clean a surface and then immediately re-deposit contaminants on it. Following that, the system is flushed with copious quantities of water and the pH of the effluent is monitored until all of the nitric acid has been removed. The column is then reconnected and the washing is continued on through 50:50 methanol:water to pure methanol and back again, through the sequence, to mobile phase.

If the glassy carbon electrode does not respond to the diamond polish it too can withstand, and benefit from, the nitric acid wash. However, this is considered to be a "last-ditch" effort to save a cell and is not a routine procedure. In this case, the HPLC-ECD system would be connected in such a way as to by-pass the column and flush the electrode compartment. The technique as described above is followed. However, it must be established, prior to starting a nitric acid wash of the glassy carbon electrode, that all of the connecting tubing can also withstand the nitric acid. If this is not the case, then the glassy carbon cell should be removed from the system and merely rinsed in nitric acid. Care must be exercised so that the wire connector junction on the underside of the working electrode is not corroded by the acid; it is preferred that the acid not come into contact with the junction at all.

As a final note to this section, it must be reiterated that solutions which will enter the HPLC-ECD apparatus must be prefiltered and de-gassed prior to introduction into the system. Once again, the level of purity of the components of these solutions is crucial to the success of maintaining a quiet baseline and a high level of sensitivity of the ECD (i.e., at 1 nA or less F.S.D.).

MAINTENANCE OF ELECTROCHEMICAL DETECTOR

After the assay is operated for a certain period of time, sensitivity of the ECD cell will decrease due to accumulation of impurities on the surface of the working electrode. This contamination occurs to some extent despite all precautions to exclude such pollutants. The mobile phase will start to passivate the electrode from the time it first comes into contact with it: in fact, the working electrode loses sensitivity from the time it becomes equilibrated at a rate of up to 15% (i.e. 15% of maximum attainable signal) per day. In the inventor's experience, when the sensitivity decreases to 75% of maximum attainable signal, the cell is cleaned and rejuvenated with a unique polishing technique designed to take care of this problem.

The criteria for the initiation of the polishing procedure is derived on the basis of the loss of resolution of the epinephrine (A) peak: a 25% reduction in maximum attainable peak size also implies a concomitant increase in baseline noise which would further obscure the peak. When plasma samples containing low, resting levels of epinephrine are being injected, this represents a significant, and unacceptable, loss in sensitivity. Epinephrine is present in plasma in low concentrations and the molecule has a relatively low electroactivity. In practice, the polishing technique described below is necessitated only about every four to six weeks, depending on the types and numbers of chromatograms being run; this is due, in part, to the effectiveness of the daily and weekly regimens for care of the HPLC-ECD system.

The procedure is to first bring the system "down" into methanol, then to take the working electrode assembly out of its mounting and then to take it apart. The top part (stainless steel) of the cell and the gasket (Teflon) are rinsed off with ultrapure water, then briefly (30 seconds) sonicated in 50:50 (v/v) methanol:water (both ultrapure reagents), rinsed with water and oven-dried.

The bottom half of the cell, containing the glassy carbon electrode, is polished with, in sequence, 6 $\mu$ and 0.25 $\mu$ diamond fragments, obtainable as an aqueous paste from, for example, Buehler [Buehler Ltd., Lake Bluff, Ill. 60044.]. It is preferred that natural diamond fragments be used but it is also possible to use synthetic diamond fragments. It is desirable to use 1 μ natural diamond polish in between the 6 μ, and 0.25 μ polish but it is not absolutely necessary. Several drops of water are placed on a circle of diamond polishing cloth (e.g., Microcloth) onto which one to two mL of the paste are squeezed. The cell is placed, face down, onto the paste and with gentle pressure of the hand (applying slightly more pressure than would be exerted by the weight of the wrist alone), the cell is rubbed on the cloth for 30 seconds in a clockwise direction and then for thirty seconds in the counterclockwise direction. If the cloth starts to have heavy black streaks on it during this procedure, it is an indication that excess force is being applied.

The cell is rinsed with copious quantities of water between the different sizes of diamond polish. At the end of the polishing procedure, the cell is rinsed with water and then sonicated briefly (30 seconds) in 50:50 (v/v) methanol:water, rinsed with water once again and dried in a low-temperature oven for about five minutes. Care must be taken not to allow fingerprints to be deposited anywhere near the reactive surface of the cell. The cell is replaced in its sandwich configuration and re-mounted in the apparatus. Care must also be taken to remove any air bubbles which might accumulate while the cell assembly is being re-connected to the system.

If the surface of the glassy carbon is examined under a dissecting microscope, 20× magnification, it is found to be etched with many fine lines running perpendicular to each other. The depth of these grooves should be $\leq 0.02$ μm deep. This is normal but not preferred. At the present time, it is not possible to polish this surface to a mirror-like finish; no mechanical polishing machines are known to exist which are able to file down and polish the surfaces of the plastic and the carbon concurrently. All currently available, laboratory-scale polishers are unable to handle the small size of the cell block and the challenge of the materials which comprise it. It is contemplated that with the appearance and availability of new technologies, this limitation can be overcome in the near future. At present, it is all one can do to insure that the surface of the working electrode does not have any deep gouges or pits on it that would seriously interfere with laminar flow. Similarly, the fewer scratches that are present on the surface of the cell, the better. Finally, there should be no inclusions/particles left on the surface of the electrode.

Heretofore, alumina has been used for polishing. As long as the alumina that is used for this purpose is pure α-alumina (i.e., corundum), the procedure described above will yield acceptable results. If, however, the alumina that is used contains (gamma)-alumina, or any of the other transitional alumina (either alone or in combination with the α-alumina), the polishing exercise will be unsuccessful for the following reasons: Alumina is a universal catalyst and it has been discovered that particles of alumina are often left behind by the polishing procedure in spite of sonication of the working electrode compartment. The leftover alumina remains in the valleys of the scratches on the surface of the electrode and is free to interact with molecules in the flowstream going through the cell (when it is in situ in the HPLC system). This translates into loss of sensitivity and increased baseline noise. Furthermore, on the Mohs scale, only α-alumina has a hardness of 9; (gamma)-alumina and the other transition aluminas are a relatively soft material and hence, not capable of polishing the hard surface of the glass carbon cell. Recommendations in the prior art were that if polishing with alumina was unsuccessful in restoring sensitivity, a new cell (i.e. working electrode) should be purchased. This issue is one of the most problematic aspects of maintaining an HPLC-ECD system at high levels of sensitivity.

In summary, as long as the glassy carbon working electrode is polished with an inert material having a hardness of at least 9 on the Mohs scale, the polishing technique outlined above will be effective in restoring the sensitivity of the working electrode.

EXPLANATION OF VALIDATION OF ASSAY METHODS

Any analytical method that is used must be proven to be effective by the results of specific tests which evaluate the assay technique. A number of criteria including sensitivity, recovery, reliability and reproducibility must be met in a standardized fashion before the method can be considered valid and deemed useful. These criteria must be established before an assay method is used to analyze unknown samples for the analate(s) of interest. Herein, the results of the validation experiments are pertinent chiefly from the point of view of the completeness of the evaluation of the plasma CA assay presented. Additionally, the validation experiments provide a demonstration of the use of the invention described herein. The results summarized below are unique in that these data were all collected at 1 nA F.S.D.

It is important to appreciate that there are a number of possible approaches to an assessment of the effectiveness of an assay. Furthermore, this assessment must be repeated at regular intervals as a quality control measure; it cannot be assumed that the performance of an assay is unchanged by the passage of time. In fact, assays are often capricious. The state of an assay method at any particular point in time, and over time, must be established experimentally.

It is emphasized that the data concerning the state of an assay can change in response to major changes in the assay methodology, such as (for this invention) alterations to MP cómposition. Therefore, the assay evaluation procedures must also be repeated after all major alterations to the assay method or equipment.

The following characteristics of the human, plasma, HPLC-ECD CA assay reported herein will be described below: the condition of the baseline at 1 nA F.S.D., the operating potential of the ECD, repeatability of the injections made onto the HPLC-ECD apparatus, the linearity of the ECD with respect to the CAs and the internal standard, the degree of recovery of the analates (i.e. the CAs) by the entire assay procedure and the inter-, and intra-assay variability (i.e., reliability and reproducibility) are presented. Additionally, there will be an explanation of the interpretation of chromatograms generated by the injection of a variety of samples (including standards and extracts of unknown samples) into the HPLC-ECD apparatus and the collection of data from these chromatograms (with particular emphasis on chromatograms produced by the dedicated integrator as opposed to data collected from the output of a strip-chart recorder). Details, as required, are provided in this text or with the accompanying Figures.

BASELINE MONITORING

In the case of the HPLC-ECD CA assay presented herein, the ability to maintain a quiet baseline at 1 nA or less F.S.D. is the most fundamental characteristic of the HPLC-ECD apparatus' participation in the assay method. The condition of the baseline is one of the major determinants of the limit of sensitivity of the entire CA assay because it is the final contributor to the discrimination and detection of the analate(s) (i.e., the baseline demonstrates the actual signal:noise ratio of the apparatus). Whatever advances have been made in extracting the CAs away from the sample matrix and separating them away from each other chromatographically can all be negated by a noisy baseline. The elucidation of an optimal mobile phase composition as described above must be ascertained experimentally.

Figure 3A:
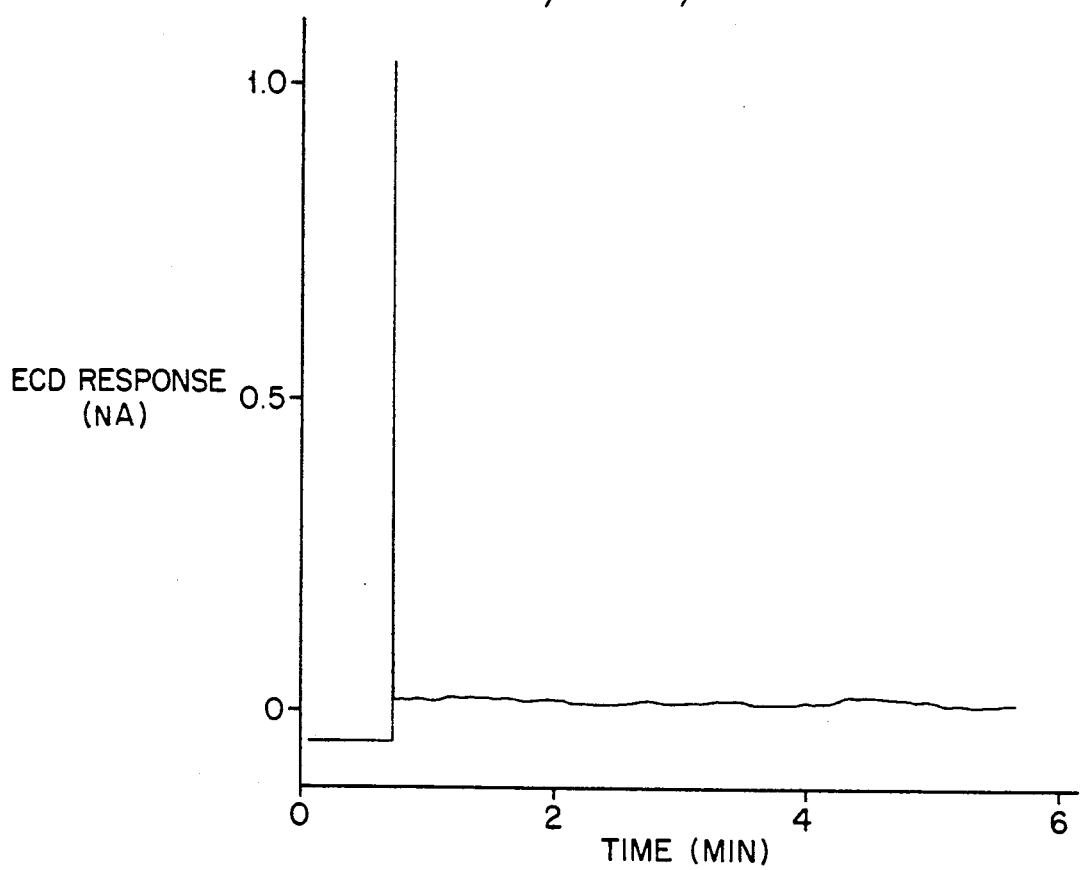
FIG. 3A is a recorder tracing of an example of a baseline of the present invention.
Figure 3B:
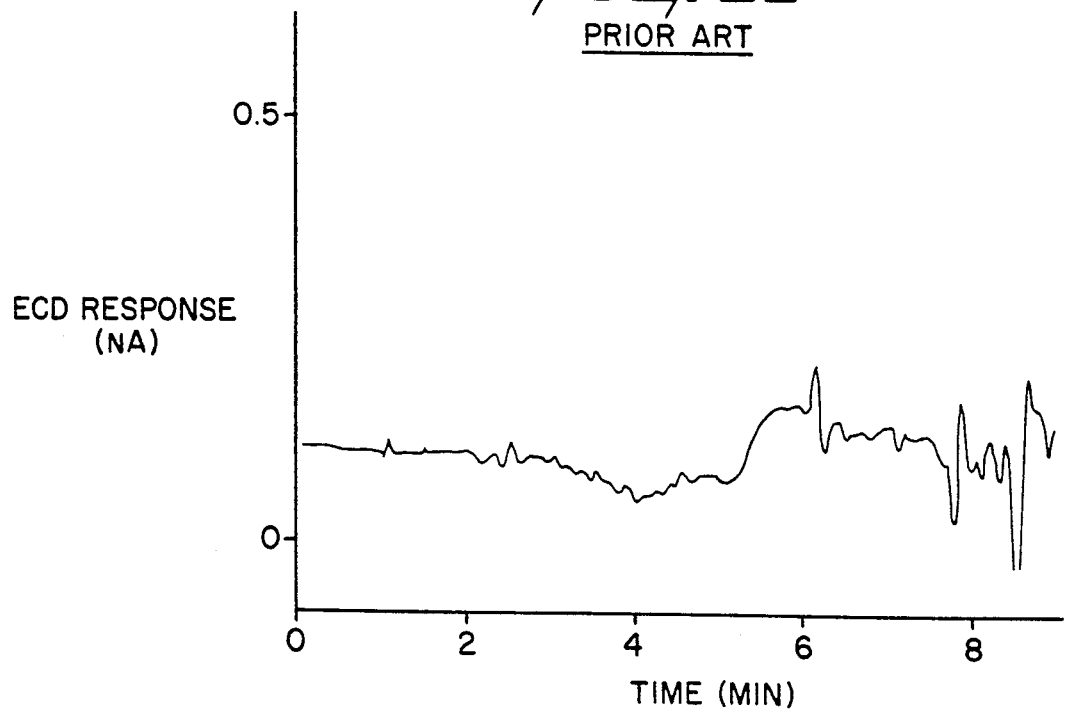
FIG. 3B is a recorder tracing of an example of a baseline of the prior art.

The actual state of the baseline can be discerned on a continuous basis, as long as the ECD cell is on. Careful attention must be paid to the state of the baseline because it will manifest problems with the HPLC-ECD equipment before these problems have had an opportunity to affect (i.e., interfere with) the chromatographic separation and/or the electrochemical detection of the compounds of interest. Any problems that arise can thus be dealt with before critical analyses have been ruined by equipment failures. In both clinical and research settings, the samples which are assayed for their CA content are often obtained at special points in time and/or under special circumstances which cannot be reproduced at will. The normal state of the baseline at 1 nA F.S.D. of the HPLC-ECD CA assay reported herein is shown in FIG. 3A.

The greatest single contributor to baseline noise is the purity of the chemicals used to make up the mobile phase (and the extraction solutions). This issue has been dealt with extensively above.

DETERMINATION OF OPERATING POTENTIAL

The continuing, optimum, functioning of the electrochemical detector cell is one of the most critical aspects of the HPLC-ECD method. It is fair to state that the evaluation experiments for the CA assay as a whole are really fundamentally concerned with characterizing the state of the cell at 1 nA or less F.S.D. One of the first things which needs to be established is the optimum operating potential of the working electrode with respect to the analates of interest. This is determined by creating a polarogram and has been covered earlier in this document. Based on the data, an operating potential of +0.72 V (vs. Ag/AgCl) is recommended in the present instance.

REPEATABILITY OF INJECTIONS

From here on, the discussion will focus on the results of injected samples. It is important to establish the reproducibility of the injection skills of the operator of the HPLC-ECD apparatus. This is done by the performance of serial injections of a representative sample into the apparatus and the mathematical determination of the repeatability (via the coefficient of variation of repeat injections) of the resulting peaks on the chromatogram. In the present instance, the following concentrations of CA standards were injected five times in a row, with the cell equilibrated on 1 nA F.S.D.: 2500 pg. NA; 500 pg. A; 1000 pg. DA; and, 2000 pg. DOE. The coefficients of variation in all cases were below 2%. The corresponding retention times for NA, A, DA, and DOE are 2.4, 3.4, 5.5 and 7.8 minutes, respectively.

It is important to appreciate the difference between the ECD's ability to detect CAs from standard solutions injected directly onto the column as opposed to the cell's ability to visualize CAs extracted from complex matrices. These two qualities are not equivalent and must be determined independently of each other. The ECD cell's ability to discriminate CAs in a standard solution is dependent only upon the purity of the standards, the success of separation by the column (therefore, one obtains an evaluation of the chromatographic abilities of the system) and the degree of sensitivity of the cell (determined, in part, by the condition of the baseline). On the other hand, the discrimination of CAs from "junk" peaks on the chromatogram of an unknown sample is an assessment of the entire assay (including the assay's ability to remove CAs from the sample matrix [plasma], concentrate and separate [by HPLC] the CAs away from interfering substances and detect [by ECD] the remainder as representative of the physiological condition which generated the molecules). This physiological consideration is quite a different matter and will be dealt with in greater detail below.

DETERMINATION OF LINEARITY

Figure 5A:
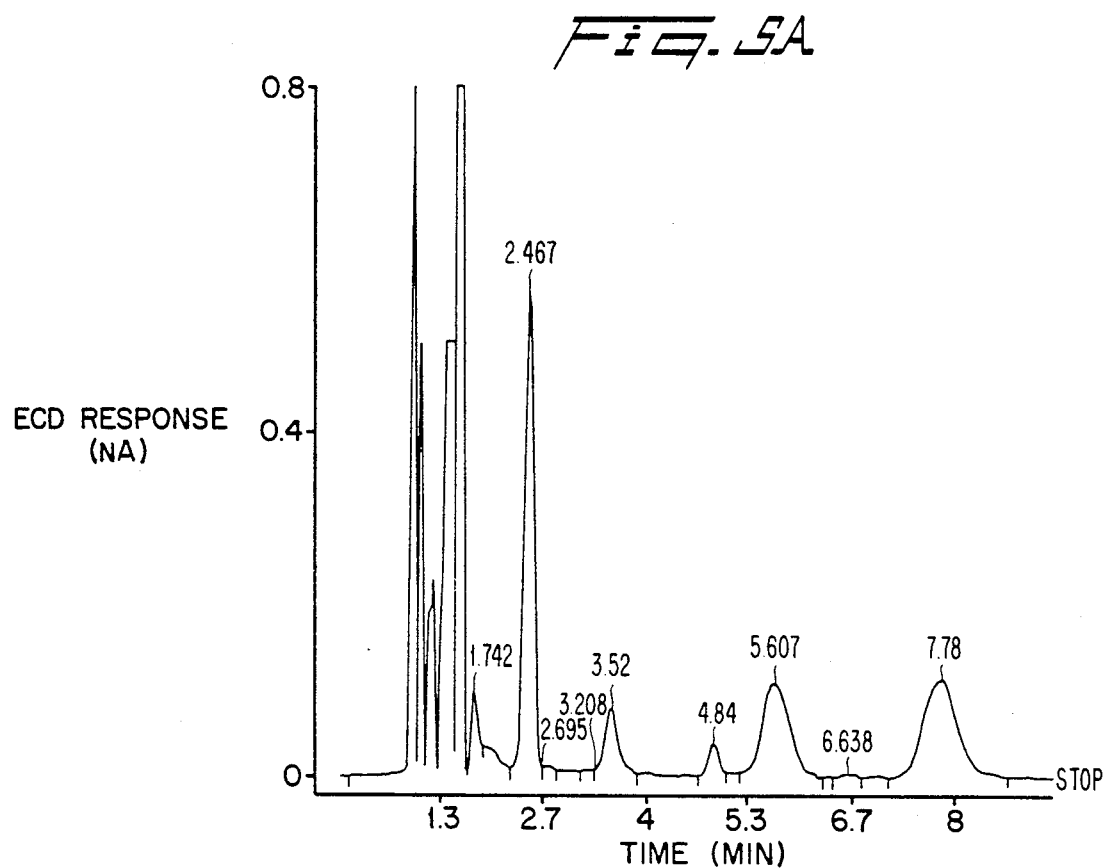
FIG. 5A is an integrator tracing of an example of a chromatogram produced by injection of a standard solution of catecholamines into the HPLC-ECD apparatus of the invention set at one nanoamp full scale deflection.

The linearity and sensitivity of the detector cell define and delineate its ability to detect CAs at all. This ability is ascertained by performing multiple injections of standard solutions of CAs (prepared from CA powders) onto the HPLC-ECD apparatus. This type of injection generates a simple chromatogram, consisting only of a solvent front and (a) peak(s) corresponding exactly to the kind and amount of CA present in the standard solution. Identity of individual peaks is determined on the basis of injection of solutions containing single CAs appropriately diluted. FIG. 5A represents an example of a chromatogram produced by the integrator following injection of a 50 $\mu$L sample containing the following quantities of CA standards: 500, 100, 200 and 400 pg. of NA, A, DA and DOE, respectively. [The ECD was set at 1 nA F.S.D. and the retention times were: 2.5, 3.5, 5.6 and 7.8 min. for NA, A, DA and DOE, respectively.]

Linearity experiments are carried out by preparation of a series of solutions, representing a wide, but physiologically relevant concentration range and the performance of serial injections of these solutions, preferably in (at least) triplicate. The important factor is the amount of the substance [CA] injected onto the column, and not the concentration of the solution from which that injection came. A standard "curve" is then plotted of detector response (in $\mu$V) versus CA concentration. The ensuing relationship should be linear and pass through the origin.

Examples of four such curves are shown in FIG. 7 A–D for the detector set at 1 nA F.S.D. Peak height was measured at seven concentration points, injected in triplicate, on the same day. The lowest point on the curve corresponds to 50% of the normal resting plasma CA values, and the highest point on the curve corresponds to the maximal concentration normally found in subjects under stress (of, say, a maximal exercise test). More specifically, the quantities injected in this instance were:

| Picograms injected in 50 μL | | | |
|---|---|---|---|
| NA | A | DA | DOE |
| 100 | 20 | 40 | 80 |
| 250 | 50 | 100 | 200 |
| 500 | 100 | 200 | 400 |
| 1250 | 250 | 500 | 1000 |
| 2500 | 500 | 1000 | 2000 |
| 3750 | 750 | 1500 | 3000 |
| 5000 | 1000 | 2000 | 4000 |

A representative set of linear regression equations obtained for the present invention are:

NA: $y = 11.59x - 320.78$; $r = 1.00$
A: $y = 7.94x - 42.29$; $r = 1.00$
DA: $y = 5.48x - 88.86$; $r = 1.00$
DOE: $y = 2.96x - 106.90$; $r = 1.00$

The sensitivity of the ECD at 0.5 nA F.S.D. is particularly suited to the lower portion of the physiologically relevant concentration range of the CAs (the so-called, low resting levels). Therefore, another set of standard curves was derived from a test of the linearity of the ECD while set at the more sensitive 0.5 nA F.S.D. Triplicate injections were made of each of the following amounts of CAs:

| Picograms Injected in 50 μL | | | |
|---|---|---|---|
| NA | A | DA | DOE |
| 100 | 20 | 40 | 80 |
| 250 | 50 | 100 | 200 |
| 500 | 100 | 200 | 800 |
| 1250 | 250 | 500 | 1000 |
| 2500 | 500 | 1000 | 2000 |

A representative set of linear regression equations obtained for these calibration curves are as follows:

NA: $y = 20.75x - 89.55$; $r = 1.00$
A: $y = 13.92x + 24.51$; $r = 1.00$
DA: $y = 9.90x - 8.25$; $r = 1.00$
DOE: $y = 5.33x - 12.96$; $r = 1.00$

Figure 5B:
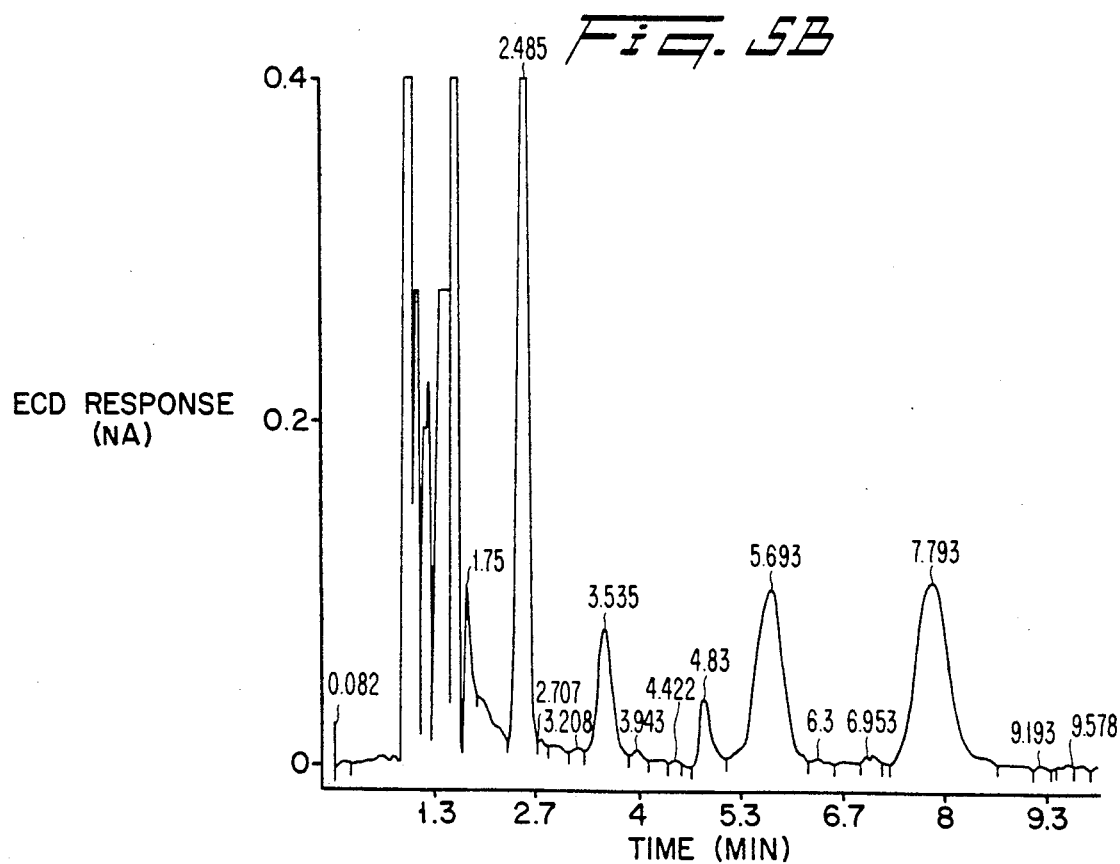
FIG. 5B is an integrator tracing of an example of a chromatogram produced by injection of a standard solution of catecholamines into the HPLC-ECD apparatus set at one half nanoamp full scale deflection.

An example of a chromatogram produced by the injection of standards with the ECD set at 0.5 nA F.S.D. is shown in FIG. 5B. This chromatogram was produced (by the integrator) upon injection of a 50 μL sample containing the following quantities of CA standards: 500, 100, 200 and 400 pg. of NA, A, DA and DOE, respectively. The retention times were 2.5, 3.5, 5.7 and 7.8 minutes for NA, A, DA and DOE, respectively.

These kinds of experimental data also yield a type of curve known as a measured versus expected curve. Since the physical amount of CA injected on the column is known, this is a test of how well that actual amount was predicted by the calculation method which is used in the laboratory (i.e., in the present instance, the integrator) to interpret the chromatograms. The slope of this curve should be as close to unity as possible and deviations from it represent the degree of error inherent in the analysis method.

DETERMINATION OF % RECOVERY

These experiments validate the extraction method and determine the efficiency of the entire assay. Recovery experiments consist of subjecting a physiological matrix (containing a known amount of CA) to the entire assay procedure and determining the losses incurred during the procedure. An abbreviated version of this assessment is run every time the assay is used by the addition of an internal standard to the matrix being extracted. In the present invention, DOE (deoxyepinephrine) is employed as the internal standard instead of the more commonly used DHBA (dihydroxybenzylamine).

The actual set of recovery experiments used to evaluate the CA assay method are performed as follows: a series of samples of blank plasma (that is, plasma devoid of CAs) is spiked with a number of standard concentrations of CAs which represent the physiological range. The different concentration levels are then extracted and injected on the column and the losses are discerned from the results by comparison with injected, unextracted standard solutions (this is known as "absolute recovery"). [Typical values obtained in these experiments are in the 80–100% range.] The relative recovery of the analytes of interest is also calculated: this is the recovery of an analate in terms of the recovery of the internal standard. [Typical values obtained employing this calculation are in the 90–125% range.] This latter calculation assumes that the reaction of each CA to the assay procedure will be identical, and this may or may not be the case.

In the present invention, this experiment has been performed by extracting triplicate repetitions of three concentrations representing a high, medium and a low value from the human physiological range. The concentrations used are as follows:

TABLE 1

| | Picograms Injected in 50 μL | | |
|---|---|---|---|
| | HIGH | MEDIUM | LOW |
| NA | 5000 | 2500 | 500 |
| A | 1000 | 500 | 100 |
| DA | 2000 | 1000 | 200 |
| DOE | 4000 | 2000 | 400 |

The entire experiment is usually performed about twice a year and after all major changes or modifications made to the HPLC-ECD system.

An abbreviated version of this assessment is run every day by the inclusion of the internal standard to the sample before it is extracted and the calculation of the daily, % Absolute Recovery. In this way, it is possible to keep track of the extraction procedure and chromatographic conditions on an on-going basis. Because this particular assessment of the assay uses a great deal of blood, it is common practice to choose only a single concentration point (e.g., the medium concentration) to be evaluated at regular intervals (e.g., once a month).

The information contained in the results of the recovery experiments have important implications for the detection limits of the assay: the detection limit is the major manifestation of the degree and extent of baseline noise. However, even if baseline noise is minimal, poor (i.e., low extraction of analates will yield an unsatisfactory chromatogram (i.e., poor recovery of analates yields small peaks on the chromatogram unless the sample came from an individual with exceptionally high CA levels). Therefore, the baseline noise and the degree of extraction of analates will be the primary determinants of the utility of the assay and will delineate the boundaries of the efficacy of the assay.

The results of the planned series of recovery experiments will depend, to a great extent, on the quality of the plasma used to perform the test. Blank plasma means plasma without CAs but also infers plasma without CA-like molecules of a structure sufficiently similar to the CAs so as to interfere with their discrimination by the column and cell. Included in this restriction are substances which would elute at the same time as the NA (i.e., very close to the solvent front) and obliterate it plus substances which interfere with the elution of the other CAs. This plasma normally comes from a pool maintained by the laboratory and collected from subjects who are not taking any drugs which have a similar structure to the CAs and/or compounds which are susceptible to the extraction technique.

INTERPRETATION OF CHROMATOGRAMS

It is important to appreciate that extracts of plasma generate a complex chromatogram which contains not only CA peaks but also peaks whose origin is obscure. [See FIG. 5C for an example of a chromatogram produced by the integrator in response to injection of a 50 $\mu$L sample of an extract of human plasma. (The boric acid technique reported herein was used to extract the CAs from the plasma.) The retention times of the NA, A and DOE peaks were at 2.6, 3.5 and 7.8 minutes, respectively. The ECD was set at 1 nA F.S.D. ] These additional peaks are derived from a number of sources, including: substances in plasma which have survived the extraction procedure, breakdown products of the standard CAs added, substances carried forward from the extraction procedures' solutions, contaminants in the mobile phase, breakdown products from the column and substances washed through the system.

It is very difficult to trace the origin of individual, interfering peaks but this must be attempted to the fullest extent possible. One way of tracing the source of some interfering peaks is to extract blank plasma which has not had standard CAs added to it. The ensuing chromatograms serve as true "system blanks", that is, they depict the minimum noise level generated by the extraction procedure and the HPLC-ECD apparatus. These chromatograms can be subtracted from the chromatograms generated by the spiked, blank plasma extracts to obtain a clear impression of the CA peaks. This subtraction function is performed by a Shimadzu C-R5A (or C-R3A), dedicated integrator, described previously. It is extremely important that the chromatograms which are subtracted are fundamentally equivalent to each other. For example: a chromatogram generated by unspiked blank plasma is the only one which can be subtracted from a chromatogram generated by spiked blank plasma. These experiments provide an assessment of the amount of background noise that can be expected to be imposed on all chromatograms produced by the assay.

Another way of tracing the origin of interfering substances present on the chromatograms of unknown samples is to subject a buffer solution to the extraction procedure, instead of plasma. This will demonstrate the peaks which are left over from the constituents of the extraction solutions themselves. One of these contaminants could be a breakdown product of DPBEA; another could be an impurity in the octanol. It must be borne in mind that the extraction procedure is essentially a strong, solvent-acid-base wash treatment of the plasma; as such, the extracting solutions will have the power to take any susceptible molecule along with them. Included here are impurities in the chemicals which comprise the extracting solutions themselves (and impurities in chemicals which were used to make up these extraction solutions, such as acids used to adjust the pH). This is yet another demonstration of the need to use only ultrapure chemicals in this assay and in conjunction with this equipment.

When interpretation of unknown sample chromatograms is performed, careful confirmation of peak identity is essential for ensuring that the appropriate peaks are quantified and that there are no impurities co-eluting with the compounds of interest (i.e. the CAs). The preferred method is to compare the retention times of peaks from standard injections to the retention times of the peaks on the chromatogram from the plasma extract. It is pointed out, however, that coincidence of retention times is not proof of identity of chemical species.

Amperometric detection offers the possibility to perform on-line characterization of electroactive solutes. This can be accomplished by essentially running a polarogram on every single blood sample extract: repeated injections of the sample extract are made at varying voltages (in increments of 0.08 V) and the relative current ratios ($\phi$) are computed. This is simply the ratio of the detector's current response at any given potential to that of its maximal response. When $\phi$ is plotted as a function of applied potential, a hydrodynamic voltammogram results. A curve generated by injection of an unknown sample can then be compared to a curve generated by the injection of a standard solution. If there are three CAs, then there will be three curves.

Because this latter procedure is very time-consuming, it is often necessary to take peak identification on faith, i.e., experience from the evidence of the matching retention times of chromatograms generated by standard injections. The use of the internal standard helps to confirm the comparative properties of the chromatograms. As long as the subjects of the study are not taking any drugs which might interfere with the separation, this is a safe assumption. However, if the subjects of the study have ingested anything which has a molecular structure similar to that of the CAs, the chromatograms resulting from the analysis of their plasma could be quickly rendered meaningless.

If it is desired to subtract noise away from the chromatogram to obtain a clearer picture of the CA peaks, plasma obtained from the subjects of the study must be used for this purpose. First of all, plasma from an individual must have the CAs removed from it and then this plasma must be extracted. The ensuing chromatogram (i.e., from CA-free plasma) can then be subtracted from the chromatogram(s) of interest (i.e., containing CAs to be quantified). It must be emphasized that if subtraction of chromatograms will be performed in the course of an experimental study, it is imperative that every single individual subject in the study act as his/her own control; that is, neither CA-free plasma from another subject nor CA-free plasma obtained from a pool can be used as a (chromatographic) subtraction blank for the chromatogram of the unknown plasma extract of any one subject.

Another way of identifying unknown peaks involves spiking the plasma with standard CAs prior to extraction. This will yield a chromatogram with exaggerated CA peaks; the difference in height between the spiked and the non-spiked plasma chromatograms represents the actual CA content of the plasma. This technique also serves to confirm the identity of the CA peaks on the chromatogram. The major disadvantage of this method of identification is that it requires more plasma than is normally available for analysis. Compared to other verification techniques, however, it requires less plasma than some of the other methods described above.

The blood to be used in validation experiments should be comparable to that which will ultimately be measured by the assay: most often, this would be normal, adult human blood, free from drugs and taken from people who are healthy and not under any significant psychological stress (the latter requirement arising from the role of CAs as neurotransmitters in the brain as well as stress hormones in the periphery). This would not, however, be a valid standard for pediatric studies. Ideally, the source of that blood should remain the same over the lifetime of the assay in that laboratory. Most clinical laboratories create their own "plasma pools" from which standardized aliquots are taken whenever necessary.

The evaluation of the extraction method should also include an assessment of how susceptible the extraction is to interference by substances of similar structure but not of interest to the operator of the assay. In this instance, interfering substances are defined as those which are susceptible to the extraction techniques employed by virtue of their chemical similarity to the CAs and which will be displayed on the chromatogram at a retention time which obscures the CA peaks. These substances may originate from a multiplicity of sources within the individual under study and include endogenous as well as administered substances.

Interfering compounds are a problem in CA studies for a variety of reasons but also as a possible cause of the so-called, "false-positive" assay test results. Because the final assessment of the native CA levels in the sample of interest is gleaned from the chromatograms, interfering compounds which co-elute with the CAs and obscure the natural peak shapes of the pure compounds (i.e., the CAs) thus give rise to incorrect interpretation of peaks. Therefore, it is extremely important to be aware of the possibility of this source of error and to exercise vigilance in controlling the effect(s) of such interfering compounds on the chromatograms and, ultimately, the CA study. Knowledge about such interference is gleaned partly from experience and partly from the knowledge of which drugs or CA-like substances the subject under study may have ingested.

Validation of the HPLC-ECD CA assay's performance in a particular laboratory over time can be accomplished, principally, by two avenues: (1) by performing a series of experiments which determine the inter- and intra-assay variability at regular intervals; and (2) by comparing the new method's (e.g., HPLC-ECD with boric acid extraction) results with those obtained utilizing established methods (e.g., REA). The practical limitations of these options, as they apply to CA assays, are the principal reasons for the decisions made and the choice of experiments which are ultimately performed. The issues normally involved in the decision-making process as to which option should be chosen include the amount of time and plasma required to complete the experiments and any special equipment requirements. Of the two major approaches, the test of variability experiments are the most straight-forward to carry out. This point will be elaborated upon below.

INTER-, AND INTRA-ASSAY VARIABILITY

For inter- and intra-assay variability, the systematic and random errors are determined for the method being evaluated. While it is impossible to completely eliminate sources of error from any procedure undertaken, it is possible to characterize, quantify and attempt to minimize that error.

The intra-assay variability is the systematic error inherent in the method, error that will be present on a daily basis. This is evaluated by analyzing the same blood sample (spiked with a known quantity of CAs) repeatedly on the same day. Ideally, if an assay will be covering a wide concentration range, the variability of the method should be characterized across that range. Considering the plasma requirements of such an experiment, this is generally not a practical option. The alternative is to assay a single concentration level, within the physiologically significant range. Using the medium concentration level set forth above, in the description of dealing with the recovery experiments, it is possible to assay five samples of plasma on the same day. [Typical results obtained in this type of experiment (expressed as coefficients of variation) are: 6.0% (NA), 1.8% (A), 1.4% (DA) and 1.1% (DOE).]

Inter-assay variability is an estimate of the random error which can be expected to creep into the assay method over a longer period of time. Typically, the unit of time used to evaluate this is one week. Once again, the more repetitions that are possible on a single sample the better, and, it would be advantageous to cover the physiologically relevant concentration range. The compromise position is to select a mid-range concentration level and evaluate it (rather than a high concentration range which would not show perturbations as readily). [Typical results obtained from this kind of experiment (expressed as coefficients of variation) are: 1.07% (NA), 2.20% (A), 4.22% (DA) and 1.67% (DOE).]

COMPARISON OF METHODS

Validation of the assay against other techniques such as the REA requires the possession of all the equipment and technical expertise necessary to perform both assays. In this case, the same sample must be subjected to both assay procedures and the results of the two methods compared. This is often not a realistic option, for a number of reasons.

Alternatively, a reference sample service could be employed as is done with many complex analyses (e.g., estrogen receptor). This involves the analysis of samples sent by the service to the individual laboratory, the determination of the CA content of the samples by the receiving lab, the return of the results to the central lab, and the receipt (from the central laboratory or source of the service) of the interpretation of these results in comparison to results obtained by other laboratories analyzing the same sample. This type of quality control measure standardizes an analytical field and renders results from different labs comparable. In the absence of such practices, it is not possible to consider results from different laboratories equivalent and inter-changeable. This has implications for the usefulness of an analytical procedure in interpretations of data obtained from both research and clinical environments and reported in the literature. At the present time, this service is not available for CA assays.

Ideally, all of the techniques described above should be used to evaluate the performance of an individual laboratory's CA assay protocol.

It will be appreciated that the methods described herein can be employed so as to take advantage of the functioning of an ECD at a high sensitivity level (i.e., 1 nA or less, F.S.D.) on a continuous basis for the purposes of a broad range of analytical needs other than the analysis of biogenic amines. Other analytical needs include, but are not limited to, ECD of electroactive molecules (or their derivatives) as taken from: water samples (e.g., those obtained from natural sources and effluents); products of synthetic chemistry including polymers, plastics and other chemicals; raw materials; plating baths; gunshot residues; agricultural products including animal feeds; drugs, beverages and foods; cosmetics.

The invention is illustrated by the following examples.

EXAMPLE 1

A. Preparation of Glassware

The following procedures are performed on all glassware which will ultimately come into contact with the assay and/or attendant equipment (including the HPLC-ECD apparatus). This includes all of the glassware used to prepare the mobile phase and its constituents and the components of the extraction procedure (i.e., erlenmeyer flasks, graduated cylinders, bottles, etc.).

Firstly, and prior to initial use of the glassware in the CA laboratory, the glassware is subjected to a dichromic-sulfuric acid bath. The glassware is soaked in the acid solution overnight and the acid is subsequently rinsed away with copious quantities of water, preferably distilled. The glassware is then washed in a solution of a substantially residue-free detergent, such as Hemo-Sol, diluted in water (preferably distilled water). The glassware is soaked in the detergent solution for at least two hours, preferably overnight. The detergent is rinsed away with copious quantities of distilled water; a final rinse is performed using double-distilled or de-ionized water before the glassware is oven-dried. Once the glassware has dried, it is stored with all orifices covered.

Each piece of glassware is used only once and after use, it is placed back into the detergent washing solution where it undergoes the washing procedure again. The dichromic-sulfuric acid bath treatment is repeated only as required (i.e., when a residue has built up once again on the contact surface of the glassware).

Any glassware which will be used to extract the plasma (i.e., the CA-containing matrix to be analyzed) or to transfer or store it must be siliconized prior to use. That is, a mono-molecular layer of silicone must be deposited on the contact surfaces of glassware destined to come into contact with the sample to be analyzed. Amongst the types of glassware which must be siliconized are the culture tubes (in which the extractions are carried out) and the transfer, glass, pasteur pipettes. A siliconizing solution is prepared into which clean glassware (directly from the oven after washing as described above) is dipped momentarily and then the glassware is baked in a high-temperature oven. The siliconizing solution is either a commercially prepared cocktail (e.g., from Serva Feinbiochemica) and the manufacturers' directions for the preparation of the glassware are followed; or, alternatively, a 5% solution of dichlorodimethylsilane in a clean hydrocarbon or chlorinated hydrocarbon solvent is prepared in the laboratory and used to siliconize the glassware.

In the present instance, a 5% solution of dicholorodimethylsilane is made up in reagent-grade toluene. The clean glassware (used directly from the oven after washing as outlined above) is immersed in the siliconizing solution, the excess is drained away and the glassware is baked in a 300° F. oven for two hours. The siliconized glassware is rinsed with distilled water after the baking treatment to remove any excess silane and oven-dried. After the glassware has cooled, it is stored covered to protect it from dust. If too much silicone has been deposited on the contact surface of the glassware, that surface will appear slightly cloudy in the light.

The integrity of the silicone-layer coating is ascertained from the appearance of the glass: if well-defined beads of water form on the silane-coated surfaces, the monolayer has not been damaged by use. If water cannot form discrete beads on the coated surface, the item must be re-siliconized. Normally, the culture tubes must be re-siliconized after each use due to the corrosive effects of the ammonium hydroxide-ammonium chloride solution used in the extraction procedure. In this case, they are washed after use, dried and re-siliconized. It is not necessary to remove the remnants of the silicone coating between treatments but if it is desired to do so, this can be accomplished with an alcoholic potassium hydroxide solution. The glassware should be soaked in the following solution for at least 30 to 60 minutes, and preferably overnight: 25:25:50 (v/v/v) potassium hydroxide:water:95% ethanol. After soaking in this stripping solution, the glassware should be rinsed thoroughly with distilled water and then washed in a substantially residue-free detergent and rinsed as described above. After drying, the glassware can be re-siliconized.

In the present instance, disposable glass transfer pipettes are used for large-volume dilution of solutions such as the mobile phase (normally made in 1-liter batches). Specifically, these pipettes (2-, 5- and 10-mL calibrated, borosilicate glass) are purchased sterilized and individually-wrapped and are discarded after each use.

B. Preparation of HPLC-ECD Equipment

In order to sustain continued function at 1 nA F.S.D., the HPLC-ECD apparatus must be maintained in top operating condition for use by the CA assay. The preferred components of this apparatus have been specified herein above. It is recommended that all chemicals used on the equipment in conjunction with the operation of the CA assay be of high purity (i.e., with contaminants limited to $\leq 5$ ppb).

All repairs made to the apparatus are made only while the HPLC-ECD system is running on pure methanol. If the system has been in use prior to the start of repairing (i.e. contains mobile phase), it must first be brought into pure methanol. This is accomplished by changing the running solution from mobile phase to pure water (the reference electrode is taken out at this point and placed in a solution of 3 N NaCl) to 50:50 (v/v) methanol:water to pure methanol. About 150 mL of each fluid are passed through the system at each of these steps. Any and all solutions which will ultimately come into contact with the apparatus are filtered through an 0.22 $\mu$ pore-size membrane filter and degassed (in a special glass filtration apparatus designed specifically for this purpose) for at least 20 minutes prior to use in the apparatus.

Repairs commence at the end of the HPLC-ECD system most distal from the ECD and progress towards it, in geographic sequence. For example, if the inlet filter in the mobile phase reservoir needs replacing, it is done first followed by repairs downstream from that site such as pump head seals, compression fittings and in-line filters. Care is taken to ensure that no greasy fingerprints or dust or lint are introduced into the system during repairs. Any new parts which are fitted into the HPLC-ECD apparatus as replacements are subjected to sonication for 30 seconds in 50:50 (v/v) methanol:water (both ultrapure) prior to installation in the apparatus. The operator of the equipment wears surgical gloves when handling the parts of the apparatus and during the repair procedures.

The column is disengaged from the system during all repairs to the pump and injector. This is accomplished upstream of the guard column by flipping a switch on the injector thereby causing the mobile phase to exit the system at that point (i.e., between the injector and the column).

Whenever compression fittings or pump heads are repaired, care is taken to ensure that air does not enter the system as a result of the repair procedures. This can be prevented by opening compression fittings downstream from the repair site to allow air to escape from the system rather than being conducted through it. Therefore, as each repair is made, methanol is pumped through that site in the system to purge any accumulated air away.

Care must also be taken to ensure that all fittings are tight and not leaking. Leaks along the flowpath of the mobile phase disrupt laminar flow through the HPLC-ECD system and create pulsations in the flowrate; these pulsations are ultimately manifested as baseline noise at 1 nA F.S.D. If compression fittings must be re-made by re-cutting the connecting tubing in the system and putting on new ferules and compression screws, care must be taken to ensure that the tubing is cut in as perpendicular a cut as is possible. This can be accomplished with the aid of very small tube cutting tools specifically designed for this purpose. It is preferred that tubing which must be repaired be replaced, if at all possible, with professionally pre-cut tubing which has smooth ends with perpendicular cuts.

Once all of the repairs to the system have been completed, the Guard-Pak is changed. The very last thing to be cleaned is the detector cell's glassy carbon working electrode. This is accomplished by the use of 6 $\mu$ and 0.25 $\mu$ diamond paste. (It is desirable to use 1 $\mu$ diamond polish in between the 6 $\mu$ and 0.25 $\mu$ but it is not absolutely necessary). Several drops of water are placed on a circle of diamond polishing cloth onto which one or two mL of the paste are squeezed out. The cell (i.e., the glassy carbon electrode compartment) is placed, face down, onto the paste and with gentle pressure of the hand (applying slightly more pressure than would be exerted by the weight of the wrist alone) the cell is rubbed on the cloth for 30 seconds in a clockwise direction and then for 30 seconds in a counterclockwise direction. The cell is rinsed with copious quantities of water in between use of the different sizes of diamond polish. At the end of the procedure, the cell is rinsed with water and then sonicated briefly (30 seconds) in 50:50 (v/v) methanol:water, rinsed again in water and dried in a low temperature oven for about five minutes. The detector cell is then re-assembled, taking care not to leave any air bubbles inside the sandwich.

The HPLC-ECD system is brought back "into" the mobile phase by running the following sequence of solutions through it: pure methanol to 50:50 (v/v) methanol:water to pure water (the reference electrode is re-inserted into the system at this point) to mobile phase. About 150 mL of each solution are put through the system at each stage. Once the system has returned to mobile phase, it is run at 500 psi for three days and three nights to re-attain equilibrium of the cell at 1 nA F.S.D.. The methanol wash just described is performed at least once a month.

The HPLC-ECD system is run on methanol as a cleaning measure when the sensitivity of the detector cell has diminished by 25% of the maximum attainable signal OR if the system has suddenly become contaminated 0 if the baseline noise experiences a dramatic and unexplained increase OR when repairs or replacements are to be performed on the apparatus. Under the conditions of care described herein, the lifetime of a column (e.g., $\mu$Bondapak Phenyl column) is about 300 injections and the lifetime of a glassy carbon electrode is about one year. The only way to clean the column is by the use of solvent washes (i.e., the methanol rinse described above). If these measures are not effective in restoring the column, it must be replaced.

An abbreviated version of the methanol wash sequence described above is run every weekend to clean the apparatus; in this case, only 50 mL of each fluid are run through the system at each step. At the end of every day, the apparatus is flushed with one of two possible overnight mobile phases: either a 70 mM sodium phosphate buffer, pH 4.8 with 5 mM HSA and 15% methanol OR the 70 mM sodium phosphate buffer, pH 4.8 with 0.5 mM HSA, 1 mM EDTA and 15% methanol. The choice of the two options is determined by the type of samples that were injected on that particular day. If CA standards were the principal samples injected on the day in question, then the latter overnight mobile phase is used; if the principal samples injected were extracts of plasma, then the former solution is used. The overnight MP is run through the system with a pressure head of about 500 psi (therefore, at a speed of about 0.5 mL/min). Mobile phases are not re-cycled.

If the pump or injector become seriously contaminated OR if the apparatus has not been used in some time OR before the system is used for the first time, the system must be purged with nitric acid. If the diamond polishing technique did not restore the sensitivity of the working electrode of the detector cell, it too can be cleaned with nitric acid. The column must be disconnected from the system during the nitric acid procedure. In this case, the apparatus is flushed with the following series of solutions: MP to pure water (remove reference electrode and disconnect column at this point), 100 mL of 6 N nitric acid, then pure water until the effluent is neutral (now the column can be re-connected to the system), 50:50 (v/v) methanol:water, pure methanol, then back again through 50:50 (v/v) methanol:water, pure water (replace reference electrode), then mobile phase. About 150-200 mL of fluid are passed through the apparatus at each stage of this washing sequence of solutions (with the exception of the nitric acid and the water used to flush it out of the system). It is important that the nitric acid which is used to clean the apparatus contain at most very low amounts of impurities (i.e., the nitric acid should be at least reagent grade quality). If the nitric acid procedure does not restore the apparatus (i.e., low baseline noise at 1 nA F.S.D.) and the sensitivity of the cell, the major pieces of equipment must be replaced (including the pump and the injector).

To improve the stability of the detector cell at 1 nA F.S.D., the working electrode compartment is fitted with a stainless steel top and the detectors' electronic controls are modified to reduce fundamental and non-fundamental noise as much as possible (e.g., by the use of 3-pole Butterworth as opposed to regular low-pass RC filters and resistors with $\geq 1\%$ tolerance). [It is recommended that as other improvements to the apparatus become commercially available, they are all incorporated into the equipment so as to enhance detector cell function at 1 nA F.S.D.] The flowstream of the MP is fitted with additional pulse dampeners and in-line filters. The injector, the column, the cell, its electronics and the waste container must all be enclosed in a large Faraday cage. This cage is connected to a common ground point as are all of the instruments contained therein. Each instrument inside the Faraday cage is resting on an electrical isolation platform (made of, e.g., lucite) to prevent the formation of a ground loop between the instruments via the cage. Each part of the entire HPLC-ECD assembly (including the integrator(s)) is plugged into a separate power circuit and grounded. It is preferred that an uninterruptable power source be used. Preferably, the room in which the HPLC-ECD apparatus is assembled is climate-controlled (i.e., the temperature of the room is maintained between 68° and 72° F. with a humidity level of 30-60%). It is preferred that this laboratory also be furnished with incandescent lighting (as opposed to fluorescent).

The potential of the reference electrode must be checked periodically against a standard reference source.

The outputs of the strip chart recorder and the integrator must be calibrated and matched as closely as possible prior to their use in conjunction with the HPLC-ECD apparatus. [N.B. It must be borne in mind that the strip chart recorder and integrator are set to run in parallel.] Normally, the strip chart recorder is set to run at 1 inch/min and the Shimadzu is placed on a speed setting of 3 (signifying a chart speed of 0.8 inch/min). Peak height (in $\mu V$) rather than peak area is used to calculate the data emanating from the integrator. Before unknown samples are injected into the HPLC-ECD system, both the HPLC-ECD and recording apparatus must be calibrated by the injection of serial standard solutions containing known amounts of the samples of interest.

It is important that all equipment (including the HPLC-ECD apparatus itself) which will be used to run the CA assay be dedicated to that use alone and maintained clean (including grease-, dust-, and lint-free). For example, the wrenches and files which will be used to repair the HPLC-ECD equipment must be rinsed with methanol to remove machining oils. These tools are then air-dried and stored in such a way so as not to collect dust or lint.

C. Preparation of Solutions

All chemicals which are destined to participate in the CA assay or which will ultimately come into contact with the HPLC-ECD system must be as ultrapure as commercially obtainable. This factor is an important determinant of the ability of the apparatus to maintain low baseline noise and a high sensitivity level on a continuous basis of function at 1 nA F.S.D. It is preferred that the level of impurity in all chemical compounds used in conjunction with the CA assay be limited to 5 ppb or less. The water which forms the basis of the mobile phase and many of the other solutions used by the apparatus and/or assay must be Type I Reagent Grade Water (with a preferred resistivity of at least 18 $M\Omega$). The solutions required by the assay can be divided into five main groups: (i) solutions required for the care and maintenance of all the equipment associated with the assay, (ii) mobile phase components, (iii) CA standard solutions, (iv) extraction solutions, and (v) catecholamine-free plasma.

(i) The solutions which are required for the maintenance of the equipment include the acid mixture in which the glassware is soaked prior to its employment in the CA assay (preferably, this acid bath consists of a mixture of dichromic and sulfuric acids); dish-washing solution (preferably consisting of a non-residue detergent, such as Hemo-Sol, dissolved in distilled water); Type I Reagent Grade water, which is used to rinse all the glassware and equipment associated with the assay; and in which ALL the solutions {other than the dish-washing but including the dish-rinsing} required, and used, by the assay are made); the 3 M NaCl solution in which the ECD's reference electrode is stored; the standard solutions used to calibrate the pH meter; the 10 N nitric acid solution used to clean out the HPLC-ECD apparatus; the methanol that is used to clean the apparatus on a regular basis; and, obviously, the water:methanol mixtures used to clean the apparatus normally. It is highly preferred that the NaCl, the nitric acid and the methanol that is used in these cleaning and maintenance solutions also be of high purity (i.e., HPLC-grade). The major consideration involved in the choice of standards used to calibrate any equipment (such as the pH meter) is that the standards chosen must be accurate.

(ii) The mobile phase contains four components. The methanol is purchased commercially as HPLC-grade and is used to obtain a final concentration in the mobile phase of 5% (v/v). The methanol is dispensed directly from the commercial stock bottle by the use of an amber glass repipette. The buffer that makes up the aqueous base of the mobile phase is 70 mM sodium phosphate with a pH of 4.8 that has been adjusted using a 10 N solution of ultra-pure acetic acid. The mobile phase contains (in final concentrations) 5 mM heptanesulfonate and 1 mM EDTA. The complete mobile phase must be freshly made immediately prior to use and then filtered through an 0.22 $\mu$ pore-size membrane filter and de-gassed (for at least 20 minutes) prior to introduction into the HPLC-ECD system.

(iii) The CA standard solutions are all made up in an 80 mM acetic acid (ultrapure) solution which has been prefiltered through the 0.22 $\mu$ membrane. The CA standard solutions are prepared and stored in clean amber glass bottles at $+5°$ C. and are never used if they are older than 48 hours. The basic solution of standards, from which all other concentrations are diluted, contains, in 50 $\mu L$: 5 ng norepinephrine, 1 ng epinephrine, 2 ng dopamine and 4 ng deoxyepinephrine (the internal standard). This basic, standard solution is used to calibrate the apparatus and determine the sensitivity of the detector cell. It is preferred that this solution be made fresh as required for use in the assay. It is recommended that a surgical mask be worn when the CA powders are being weighed out from the commercial stock bottles.

A separate solution containing only deoxyepinephrine is made up (to a final concentration of 4 ng/50 $\mu L$) in 80 mM acetic acid. This is used to spike the unknown samples prior to their participation in the extraction procedure; its function is to control for losses incurred to the original sample during extraction.

(iv) The solutions required by the extraction procedure can be made in advance and stored, in amber glass bottles at +5° C., for up to six months (with the exception of the buffer which can only last for two months). It is very important that all of the components of the extraction solutions are ultrapure chemicals, with a desired level of contaminants of $\leq 5$ ppb. The solutions required are: 2 M $NH_4OH$-$NH_4Cl$, pH 8.5 containing (at a final concentration of) 0.2% (w/v) diphenylborate ethanolamine (DPBEA) and 0.5% (w/v) EDTA; n-heptane+1% n-octanol containing 0.25% tetraoctylammonium bromide (TOABr); pure n-octanol; and 80 mM acetic acid. With the exception of the acetic acid, these solutions are dispensed via repipettes (either amber glass or Teflon).

(v) Catecholamine-free plasma is obtained by collecting blood from a peripheral vein of a fasted, healthy adult (human) volunteer who has not ingested, within at least the preceding ten days (preferably 14 days), any drugs or other substances which have a molecular structure similar to the CAs. People who are chronic users of anti-histamines are not suitable subjects. At least 100 mL of blood are collected from a subject at one time. The blood is collected into silicone-lined tubes and preferably without hemolysis. The blood is centrifuged to separate the cells away from the plasma. The plasma is then subjected to repeated freezing and thawing cycles on solid carbon dioxide and under cold running water, respectively (preferably at least ten times). At the end of this procedure, the plasma is centrifuged and filtered through a membrane (e.g., 0.45 $\mu$ pore-size) to remove the fibrin strands and clots. The plasma is frozen at minus 70° C. in 8 ml aliquots (in silicone-lined tubes) to be thawed out as required. Generally, during experimental procedures which require the use of this plasma, plasma from different volunteers is not mixed within a single experiment unless it was pooled prior to the freezing and thawing protocol.

D. Collection of Unknown Samples

The following discussion will focus on the collection of human plasma as the model system. Subjects are chosen according to the problem being studied within the research or clinical protocol.

It must be borne in mind that if the following, suggested protocols, are not adhered to in essence, the results of the CA study will be rendered meaningless very quickly. It cannot be overemphasized that the study of CA levels in physiological fluids of intact organisms, especially humans, is intimately intertwined with their psychological state; any perturbations to that state by the experimenters will be reflected as elevated CA levels in physiological fluids. Elevations thus created obscure the natural CA fluxes in response to internal, physiological stimuli. Catecholamines are neurotransmitters and hormones; by definition, then, to study CAs' physiological role, the experimenters cannot modulate the internal, natural rhythm of CAs without destroying the very thing which they are attempting to study. This limitation imposes some serious experimental difficulties which simply cannot be ignored.

It is imperative that subjects participating in CA studies act as their own controls; if a subject is to be followed throughout the course of the evolution of some clinical problem, the subject must have a blood sample drawn at the point of initial contact with the researchers and/or clinicians and at regularly maintained and fixed intervals thereafter. It is preferred that this interval be chosen on the basis of the circadian rhythms of the CAs.

If the subject is to be followed throughout some acute procedure, such as an exercise test, blood samples are obtained prior to, during and following the procedure; the entire procedure must be repeated within seven to ten days thereafter to establish the reproducibility of the protocol. If a number of individuals are participating in a CA study, the data obtained from them as individuals may be pooled as relative changes rather than as absolute numbers. This is different from studies in which an accurate CA concentration must be known and compared between individuals for a specified purpose. In either case, subjects must always be age-, sex-, and weight-matched; it is preferred that they are also matched as to state of health and level of physical fitness.

If a subject is to be followed throughout the course of some clinical condition (e.g., after a myocardial infarction or following a subarachnoid hemorrhage following rupture of a cerebral artery aneurysm or during a psychiatric crisis), it is imperative that a sample of blood is obtained as soon after admission to hospital as possible and before ANY drugs have been administered. This establishes that individual's "baseline CA state" and progress in the individual's condition is determined relative to this starting point. Samples are thereafter obtained at least once a day (preferably twice) at a standardized time (e.g., once in the morning and once in the evening) and in a standardized fashion until the resolution of the physiological problem or crisis. Collection of samples for assay of CAs is always accompanied by collection of other physiological information (including heart rate and blood pressure) and collection of information regarding nutrition and drugs ingested and/or administered. The subject's level of alertness must also be noted (i.e., a person who is asleep is not equivalent, in a CA sense, to a person who is awake).

Collection of plasma is always performed according to the following protocol: The fasted subject is fitted with an indwelling catheter (size 18 needle or less is preferred) connected via flexible tubing and a three-way stopcock to an intravenous (i.v.) physiological saline solution. The i.v. drip is set to run at some slow speed (such as 0.4–0.6 mL/min). Either an artery or a vein is suitable. It is preferred that the site of this line, in the body, remain constant throughout the time of study. [If a subject is being monitored throughout a hospital stay and will progress from an arterial to a venous line, it is preferred that a sample of blood be obtained from both lines on the day that the cross-over is made.]

After the i.v. line has been established, the subject is left alone to sit quietly, without any stimulation (this includes conversations and reading) for at least twenty minutes. The position of the body must be standardized throughout the course of the study. The most appropriate posture to be adopted is seated, with the back positioned vertically and the shins hanging down rather than positioned horizontally. The twenty minute-quiet period must be observed even if the i.v. line was already in place. For example, if the patient is in a ward, the patient must not be spoken to or be allowed to move around for the twenty minutes preceding the collection of the sample for CA analysis.

Similarly, if the subject of study is a patient in hospital, any nursing procedures (e.g., physiotherapy to clear the chest) must be stopped at least twenty minutes prior to the collection of the sample for CA analysis. [This latter recommendation assumes that the patient has already been fitted with an in-dwelling catheter connected to an i.v. drip via a three-way stopcock. If the patient does not have a three-way stopcock added to his/her i.v. line, the i.v. line must be modified accordingly and the patient must be allowed to rest quietly for twenty minutes following the adjustment prior to the collection of the blood sample.]

Blood is withdrawn from the subject via the three-way stopcock: two or three mL are first withdrawn from the line to eliminate the i.v. fluid; then ten mL of blood are withdrawn into a heparinized plastic syringe and the blood is immediately transferred into a cold, silicone-lined tube in an ice bucket which can be covered and protected from the light. The stopcock is simultaneously turned around so that the i.v. solution once again flushes the i.v. line clear of blood thereby preventing clot formation inside the tubing. The cover is placed on the ice bucket as soon as the blood has been transferred. The subject is not to be engaged in conversation during this procedure. The blood is returned to the analysis laboratory as soon as is practicable and preferably within one hour of collection.

The red blood cells are centrifuged away from the plasma in a darkened, refrigerated centrifuge (i.e., the blood is spun for ten minutes at $1,200 \times g$). The plasma is separated from the cells and placed into cold, silicone-lined tubes in 2.5 mL aliquots. If the plasma will be used immediately, it is maintained on ice, and in the dark, until it is extracted; otherwise, the sample is frozen at minus 70° C., or lower, until analysis. Plasma samples are stable at these temperatures for one year with minimal loss of analate. If a frozen sample is to be assayed for CAs, it is thawed quickly by passing cold water over the test tube as it is shaken, only until all of the ice inside the tube has melted; the sample is then immediately placed on ice and in the dark until it is extracted. It is preferred that samples be withdrawn from the freezer only immediately before they will be extracted.

Occasionally, the use of an active i.v. line is contraindicated. In this case, for the purpose of sampling of blood for CA assay over some period of time, the patient can be fitted with a heparin lock. This involves the insertion of an indwelling catheter into a superficial vein (preferably just below the fold on the inside of the elbow); this catheter is connected to a short piece of intravenous tubing and terminates in a three-way stopcock. The line is filled with a heparin solution (heparin lock flush solution U.S.P. @ 100 U heparin/mL isotonic aqueous solution) and the stopcock key is positioned so that no fluid can escape from the line. The entire assembly can be secured onto the patient's arm with skin tape and then wrapped with bandages so that it is protected. The patient is full mobile but has a suitable blood sampling site ready.

When it is desired to sample blood, the patient is asked to sit quietly for twenty minutes (as described above) prior to the collection of the sample. With the arm stabilized on some piece of furniture, the bandages are removed. The heparin must first be removed from the line and then blood is sampled and treated as described previously. The line is flushed with sterile, physiological saline to remove any remaining blood before being filled again with the dilute heparin-in-saline solution. The line can be closed and re-wrapped again as described above. As long as aseptic techniques and proper procedures are followed, and assuming that the catheter does not become dislodged, this kind of catheter arrangement is stable for at least one week. Once again, the emphasis is on not raising the endogenous levels of the CAs as a result of the sampling procedure.

It is not appropriate to collect blood for CA analysis by direct venipuncture. Venipuncture has the effect of raising the plasma CAs because of the stress to the individual associated with the procedure; this, then, invalidates the CA assessment as it relates to the physiological phenomenon under investigation. Therefore the collection technique must be as non-invasive as possible.

As a final note, the need to know what (if any) drugs have been ingested, and their effects on both the endogenous CA levels and on the assay, cannot be overemphasized. These drugs cannot disrupt normal function nor in any way alter it (i.e., they cannot affect the sympathoadrenal system by altering either the synthesis, release and/or metabolism of the CAs).

As far as the assay is concerned, it is vital to the integrity of the chemistry of the various reactions employed therein that any drugs that have been ingested by the subject do not adversely affect the ability of the steps of the assay to perform as required. For example: if a drug were to alter the pH of the first extraction solution used on the plasma, the CAs might not be fully removed from the plasma during that step; alternatively, if the drugs themselves are extracted from plasma and are injected onto the column, something about their inherent chemical structure might be attracted to the column and bind to it (temporarily or permanently). This would have the effect of diminishing the number of active sites on the column available for the CAs to bind; this, in turn, would diminish the degree of separation and/or resolution of the CAs by the column and thus compromise the final chromatogram. Alternatively, the drugs might precipitate on the detector and render it insensitive to the CAs in the flowstream. Another possibility is that the drugs might bind, or otherwise inactivate, the CA molecules in the sample, thereby completely annulling the purpose of the assay.

Therefore, close attention must be paid to the possibility that substances ingested by the subject have an affect(s) on the sympathoadrenal system and/or the CA assay.

Finally, it is important to reiterate that CA concentrations in physiological fluids and tissues are always considered in light of physiological data.

E. Extraction of Catecholamine from Sample

Human plasma will be used as the model system. It is preferred that the procedures described herein below be carried out in a fume hood. Two milliliters of plasma are placed into a cold, silicone-lined reaction tube (preferably glass and with a screw cap, Teflon-lined lid) to which 250 $\mu$L of the internal standard solution are added (concentration of the standard solution is 4 ng DOE per 50 $\mu$L 80 mM acetic acid). To this mixture is added 1 mL of a 2 M $NH_4OH$-$NH_4Cl$ buffer containing 0.2% (w/v) DPBEA and 0.5% (w/v) EDTA. Finally, add 5 mL of an heptane-1% octanol solution containing 0.25% (w/v) TOABr. The tube is tightly closed and the "cocktail" is shaken for two minutes at high speed (e.g., 280 excursions per minute) in a reciprocating utility shaker. The sample is then centrifuged at $1,200 \times g$ for 5 minutes in a refrigerated centrifuge.

The tube is removed from the centrifuge and the upper organic layer of the contents is lifted off using a siliconized, glass pasteur pipette and transferred into a clean, empty, siliconized tube. To this new tube are now added 2 mL of pure octanol and 250 μL of an ultrapure, and membrane filtered, solution of 80 mM acetic acid. The sample is sealed and shaken vigorously once again for two minutes. The tube is centrifuged in the refrigerated centrifuge for 5 minutes at 1,200×g.

The tube is removed from the centrifuge and the upper, organic layer is carefully lifted away from the lower, aqueous layer by vacuum suction. This organic layer is discarded. The aqueous phase is transferred into a chilled, small plastic tube with a tight-fitting lid, with the aid of a siliconized pipette. This small tube contains the sample to be injected into the HPLC-ECD apparatus and this extract is stable, on ice, for only one hour. It is possible to make two injections of the sample during this time but if any more injections are required, it is recommended that another aliquot of the same sample be thawed and extracted. It is preferred that unknown samples be analyzed by the CA assay in duplicate (i.e. two aliquots of the same original sample are analyzed, in series, on the same day).

If it is desired to extract any other solutions (such as CA standard solutions or CA-free plasma, etc.), the same protocol as described above is performed on the sample of interest; all quantities, proportions and compositions of extracting solutions are maintained as described.

F. Detection and Quantification of Catecholamine

Before an unknown sample can be injected into the HPLC-ECD system for analysis, the sensitivity, linearity and reproducibility of the electrochemical detector must be determined. It is preferable to use a sample extraction technique which will return as close to 100% of the sample as possible (i.e., as close to 100% absolute recovery as possible). It is assumed that the optimal mobile phase composition and chromatographic procedures, as well as the optimal operating potential of the ECD, have been chosen for the compounds of interest. An amperometric ECD is highly preferred for the analysis of CAs.

In the present instance, a chromatography column (size: 30 cm×3.9 mm, L.×I.D.) composed of irregularly-shaped, 10 μ particulate silica (average pore size: 125 Å; range: 50-300Å) bonded with phenyl side-chains is highly preferred. [Furthermore, the column should be end-capped; have a carbon loading of at least 8%; and have a typical efficiency of about 30,000 plates/meter at its optimal linear velocity.] The preferred column is a μBondapak Phenyl column made by Waters Chromatography Division.

Prior to the utilization of the CA assay for the analysis of unknown samples, the reliability (e.g., inter-, and intra-assay variability) and reproducibility of the entire CA assay procedure must be established. The elucidation of the performance characteristics of the assay must be verified at regular intervals as a quality control measure and after any changes to either the equipment (e.g., installation of a new column) or to the assay conditions (e.g., alteration of composition of mobile phase). During operation of the assay, the recovery of the sample and the absolute level of sensitivity of the HPLC-ECD system are monitored on a daily basis.

It is assumed that the HPLC-ECD apparatus is capable of sustaining operation at 1 nanoamp or less F.S.D. on a continuous basis with a very low level of baseline noise (i.e., with better than a signal:noise ratio of 2:1, with 6:1 or better being highly preferred).

The samples which are normally injected into the HPLC-ECD apparatus for analysis include: pure water and pure 80 mM acetic acid (these delineate the size of the solvent front and any contaminants derived from the water and/or acetic acid); CA standard solutions (these define the retention times of the individual CAs as well as providing information on the sensitivity of the ECD); extracted water, extracted buffer, extracted CA standards and extracted CA-free plasma (these provide information on the level of contaminant carry-over from the constituents of the extraction solutions and from the plasma itself to the final chromatogram); and the extracted, unknown plasma samples.

Samples are transferred into the HPLC-ECD system using a micro-syringe (normally glass and fitted with a stabilized plunger and a replaceable stainless steel needle which has a specially adapted tip suitable for use with an HPLC system) and some injector apparatus. The volume of sample injected onto the column can be up to 100 μL but it is recommended that no more than 50 μL are injected as a matter of course. The HPLC column is very sensitive to overloading and peak resolution on the chromatograms quickly becomes blurred. Injection volumes of ≦50 μL are preferred if at all possible, with 10-20 μL injections being highly preferred. It is preferred that the injector be electrically connected to the recording device(s) used in the HPLC-ECD assembly so that the injection of the sample onto the column will also trigger the start of the recording of the chromatogram. This is particularly important if chromatograms must be subtracted from each other.

The use of an electronic integrator instead of the traditional strip chart recorder permits the collection of unambiguous data regarding the peak heights (or areas) on the resulting chromatograms. This effectively eliminates an important source of error from the CA assay protocol. The integrator is programmed to print-out the height (or area) of the peaks of interest on the chromatogram and to ignore the other peaks. The information is presented in μV at the appropriate retention times. The integrator can also be programmed to calculate the recovery of the sample based on the recovery of the internal standard and to report the concentration of the unknown analate(s) in the original sample injected into the HPLC-ECD apparatus. The preferred instrument is a Shimadzu C-R3A dedicated integrator because it permits subtraction of chromatograms and is fully programmable.

It is recommended that a strip chart recorder be connected to the HPLC-ECD apparatus in parallel with the integrator. The strip chart recorder provides a real-time trace of the events taking place within the system and facilitates rapid analysis of problems which develop. The strip chart recorder is tonically recording the baseline as long as the HPLC-ECD system is running.

If a sample is injected into the HPLC-ECD apparatus for the purpose of generating a chromatogram that will be used as a subtraction chromatogram, it is extremely important that this subtraction sample be injected as close as possible to the time of the injection of the sample from whose chromatogram it will be subtracted (i.e., on the same day and within two hours of the injection of the sample from which it will be subtracted). Additionally, the injection volumes must be identical. For example, if it is desired to subtract a chromatogram of pure acetic acid from the chromatogram of a solution of CA standards, the acetic acid injection must be the same volume (e.g., 50 μL) as the injection of standards will be (e.g., also 50 μL). It is important that the two injections follow one another on the same day rather than have been injected on two different days. Because the sensitivity of the detector cell changes every day, each day that the system is operating is a case unto itself.

Furthermore, only certain chromatograms are appropriate subjects for subtraction from others. For example, only a chromatogram obtained from extraction of blank plasma (i.e. CA-free) is a suitable subtraction chromatogram for a chromatogram obtained from extraction of spiked blank plasma. The chromatogram of a patient cannot be clarified by subtraction of a chromatogram obtained from the extraction of blank plasma. In this latter case, the patient must, again, act as his/her own control. If it is desired to perform this subtraction maneuver, an aliquot of the individual patient's plasma must be subjected to the freezing and thawing procedure described above before it can be extracted as "blank plasma" and used to generate a subtraction chromatogram.

The only chromatogram which is "universally" applicable as a subtraction chromatogram would be a chromatogram of injected pure 80 mM acetic acid (with the proviso that the volume of the acetic acid injection be identical with the volume of the sample injection). However, such a chromatogram would only be appropriate fodder for subtraction on the day that it was injected. On any other day, a new injection would have to be made and used. This particular subtraction maneuver is a useful technique because it eliminates the interference of the solvent front onto the chromatogram of interest. For example, if the norepinephrine concentration of the injected unknown sample turns out to be high, it will probably be represented (on the chromatogram) by a peak broad enough to be partially obscured by the width of the solvent front. If this interference could be electronically eliminated, the calculation of the peak height of the norepinephrine would thus be rendered more accurate and the final calculations of NA concentration would thus be more closely representative of the original NA concentration in the sample.

Another technique which can be employed to clarify the complex chromatograms of unknown samples is to extract, in parallel, one aliquot of the original sample with only the internal standard added to it and another aliquot of the sample spiked with a known amount of all three CAs (i.e. added standards). This would generate two chromatograms: one with a number of characteristic peaks on it and another with all of these plus exaggerated CA peaks. These two chromatograms could then be subtracted away from each other to obtain a more accurate assessment of the original CA concentration in the sample extracted. It is preferred that this entire procedure (i.e., extracting two versions of one sample, spiked and unspiked, and then subtracting the ensuing chromatograms) and be carried out in duplicate.

If this particular spiking and subtraction technique is to be employed with any regularity, the reproduciblity of the procedure in the laboratory and on the apparatus must first be established. Obviously, prior to the adoption of this procedure as a routine protocol, one of the primary requirements which must be met is possession of sufficient quantity of sample so as to permit quadruple analysis (i.e., quadruple analysis of one sample translates into a requirement for posses ion of 9 mL of the original plasma sample which means a blood sample of almost twenty mL, depending on the hematocrit of the individual in question).

Once an acceptable final chromatogram has been obtained, a simple mathematical calculation converts the peak heights back into plasma concentrations. In performing this calculation, a number of other properties of the HPLC-ECD CA assay must be taken into consideration mathematically including the sensitivity of the detector for the individual compounds of interest, the absolute recovery of the analate(s), the chromatographic efficiency and the efficiency of the injections, and the inter-and intra-assay variability of the assay. These calculations can be performed manually or else the integrator can be programmed to perform them. The final result is reported as pg CA/mL plasma.

EXAMPLE 2

The CA assay and HPLC-ECD maintenance techniques described in Example 1 above ca be utilized without modification to assess the CA content of other physiological fluids obtained from humans including cerebrospinal, lymphatic and other extracellular fluids.

If it is desired to analyze cerebrospinal fluid (CSF) for CA content, the procedure described in Example 1(D) above must be followed for the treatment of the withdrawn sample(s). The basic conditions of collection of the sample which must be met are that the CSF sample be collected non-traumatically (i.e., without blood) and aseptically; that the sample of CSF be placed into a cold, silicone-lined test-tube; that the sample be maintained in the dark; and that the sample is frozen or analyzed as soon as is practical but dealt with within one hour of collection. It is preferred that the sample be centrifuged prior to freezing and/or analysis to ensure that any red blood cells that may be present are eliminated from the sample.

In this case (i.e., obtaining the CSF sample), the subject will have been administered certain drugs prior to and during the procedure and it is imperative that the identity of those drugs is known. The exact clinical condition of the patient at the time of the sample must also be known. It is preferred that a sample of plasma be obtained simultaneously with the withdrawal of the CSF sample. [This serves to confirm (if not establish) the CSF catecholamine content relative to the plasma values thus assisting in tracing the source of the CAs (e.g., if elevated in one fluid but not the other).] Under these conditions, it is also very important to know the patient's heart rate and blood pressure status as well as their Glasgow Coma Score, or equivalent (i.e., some assessment of the patient's level of consciousness and/or cognition). It is very important that the fluid collection technique employed not contribute to the elevation of endogenous CA levels as a result of the collection procedure (i.e., the collection of the sample must not stimulate the sympathoadrenal system). In spite of the fact that a subject who is having CSF withdrawn is already traumatized to some extent, it is very important not to exacerbate the situation.

Extracellular fluid (ECF) collection is subject to the same constraints as collection of CSF. In general, these physiological fluid samples, which will be analyzed for CA content, must be collected atraumatically, maintained in silicone-lined tubes, on ice and in the dark prior to analysis or freezing.

The extraction, separation, detection and quantification of blank CSF and ECF is accomplished using the techniques and cascades of events described in Example 1 (A-F, inclusive) above. The chromatographic and maintenance techniques described are followed without modification.

Once again, it is very important to identify the effects of any ingested foreign substances (including drugs) on the sympathoadrenal system, on the integrity of the CAs in the sample and on the CA assay itself.

[This latter stipulation includes any alterations in the chemical micro-environment of either the extraction protocol or the HPLC-ECD apparatus. This alteration can be in the guise of the formation of temporary or permanent bonds between the chemical species thereby leading to chemical or mechanical inhibition of optimal activity of the components of either the extraction method or the apparatus.]

EXAMPLE 3

The CA assay techniques outlined in Example 1 (A-F inclusive) above can also be applied, without modification, to the study of free CAs in human urine. [That is, the extraction, chromatography and maintenance techniques are all the same as described above.] The only procedural difference is the addition of a step involving pre-treatment of the urine (e.g., deproteinization) prior to the start of the extraction procedure, the recording of the daily urine output, and the confirmation of kidney function by determination of creatinine clearance. Care must be taken to see to it that the CA content of the urine is preserved throughout. The final result is reported as $\mu g$ excreted /24 hours.

Once again, the clinical state of the patient is very important as is the reason and rationale for measuring the patient's free CAs in urine. Additionally, the effect(s) of any ingested foreign substances on the sympathoadrenal system and on the CA assay (from both the chemical and equipment points of view) must be known.

[This latter stipulation includes any alterations in the chemical micro-environment of either the extraction protocol or the HPLC-ECD apparatus. This alteration can be in the guise of the formation of temporary or permanent bonds between the chemical species thereby leading to chemical or mechanical inhibition of optimal activity of the components of either the extraction method or the apparatus.]

A possible additional complication in this instance is the effect of an ingested drug on the fate of the CAs in the urine sample. For example, the drug mandelamine is metabolized to formaldehyde; formaldehyde in the urine destroys catecholamine. Therefore, a patient who is receiving this drug is not a suitable candidate for a CA study requiring an accurate urinary CA assessment.

EXAMPLE 4

The CA assay techniques described in Example 1 (A-F inclusive) above can also be applied without modification to the analysis of CA levels in (human) physiological tissues. The only difference to the protocols outlined above would be the addition of a step dealing with the collection and pre-treatment of the tissue(s) samples. Once again, the emphasis is on not contributing to the traumatization of the individual from which the sample is collected (CAs are intimately involved in the stress response). Before it can be subjected to the CA extraction procedure, the tissue sample must be pre-treated in such a way as to remove unwanted compounds and materials (such as blood cells) yet preserve the integrity of the CAs contained therein. A number of possible means of accomplishing this end exist including taking the CAs out of the tissue by chemical extraction after disruption of the tissue (e.g., by sonication or homogenization), taking the CAs out of the disrupted tissue by concentrating them on a column or other attractive and selective matrix, taking the CAs out of the (disrupted) tissue by selective precipitation of the CAs (by, for example, the use of antibodies), or by the removal of the tissue matrix away from the CAs. Whatever pre-treatment method is chosen, it must preserve the integrity of the CA molecules in the sample while at the same time eliminating interfering substances. Additionally, the integrity of the sample must be proven and the efficiency (e.g., % recovery) of the pre-treatment method as well as its reproducibility and reliability must be established prior to the employment of the technique in the assay of unknown samples for their CA content.

EXAMPLE 5

The assay techniques described above in Example 1 can be used to assay for other CAs in human plasma (including CA derivatives and metabolites, other biogenic amines and their metabolites). The only modification(s) to the protocols outlined above is(are) to the composition of the mobile phase (i.e., the relative proportions of the constituents will have to be altered to accommodate the separation and resolution of compounds other than the primary CAs) and to the relative proportions of the constituents of the extraction solution(s) (i.e., the composition of some of the extraction solutions may have to be modified slightly to accommodate the different CA-like molecules and their functional groups). The exact change(s) to be made is(are) determined on the basis of results obtained during experiments utilizing standard compounds. Once the optimal chromatographic conditions have been established for separation of the compounds of interest, the unknown samples can be analyzed.

The maintenance procedures used on all the equipment and apparatus remain the same as described above. The only change that would likely be evident is that the apparatus would not have to be run at a very high level of sensitivity and the equipment would be much easier to maintain in top operating condition. That is, because the levels of CAs in tissues are often much higher than in plasma, the ECD could be run at 10 nA F.S.D. or higher. Under the conditions of care described herein, this would not represent as serious a challenge to the equipment (or the laboratory) as maintaining 1 nA F.S.D. does.

EXAMPLES 6

The CA assay techniques described in Example 1 (A-F inclusive) above can also be used to measure the levels of other CAs derived from human cerebrospinal, lymphatic and other extracellular fluids. The only modifications which are made to the protocols described are those summarized in Examples 2 and 5.

EXAMPLES 7

The CA assay techniques described in Example 1 (A-F inclusive) above can also be used to measure the levels of other CAs found in human urine. The only modifications made to the standard protocols are those summarized in Examples 3 and 5 above.

EXAMPLES 8

The CA assay techniques described above in Example 1 (A-F inclusive) can also be used to measure the levels of other CAs in (human) tissue samples. The only modifications which must be made to the standard protocols are those summarized in Examples 4 and 5 above.

EXAMPLE 9

The CA assay techniques described above in Example 1 (A-F inclusive) can also be used to assay for CAs from sources other than human physiological fluids or tissues. These alternate sources include physiological fluids and/or tissues derived from other mammals, other vertebrates, invertebrates, plants or chemical compounds (synthetic or natural and including drugs). If the sample is being collected from a live being, care must be exercised during the sampling procedure so as to not unduly traumatize the being in the process of this collection. [We do not yet know what function(s) CA-like molecules serve for plants but it is a rational precaution to attempt to collect the sample as gently as possible.] The chromatography and extraction techniques will be identical to those described in Example 1 but the sample will have to be pre-treated before it can be extracted. The pre-treatment method chosen must remove unwanted materials and substances before the sample is subjected to the extraction technique; this pre-treatment regimen must be suitable to the source of the CAs and be designed to preserve the CAs. Once again, the most critical elements to be practiced during this pre-treatment regimen are the collection of the original sample into cold tubes (with or without preservative), the maintenance of the sample in the dark (and/or frozen), and away from proteolytic enzymes. [As discussed herein above, the CA family of molecules contains small molecular weight compounds with very subtle structural differences; many of them decompose upon exposure to light and are unstable in alkaline solutions and at temperatures greater than $+5°$ C. There is a tremendous number of things that we do not yet know about CA dynamics in other organisms. For example, we do not yet know how CA-like molecules are made or stored or metabolized in plants; until such time as these things are elucidated, it is prudent to be conservative in the treatment of the samples.] The essential components of the extraction and chromatographic techniques remain the same and the care and maintenance of the equipment is unaltered.

EXAMPLE 10

The CA assay techniques described in Example 1 (A-F inclusive) above can also be used to assay CA-like molecules derived from other sources such as other mammals, other vertebrates, invertebrates, plants or drugs (synthetic or natural). The modifications which must be made to the standard protocols include those described in Example 5. [That is, the chromatography conditions (and possibly the extraction conditions) will have to be adjusted slightly to accommodate the different functional groups of these molecules. The major components of the chromatographic procedures remain the same as described and the care and maintenance of all the equipment is the same.]

As a final note of interest, the techniques described in Examples 1-10 above can be combined with the assessment of CA concentrations of physiological fluids and tissues in vivo (this latter achievement resulting from the use of in vivo voltammetric electrodes which have recently become available).

There exists, in clinical and research settings, a significant need for a kit which presents the most critical elements of the CA assay in an accessible and clear fashion and which thereby permits facile use of the HPLC-ECD technology in the measurement of human plasma CA levels. That is, an assembly of the most critical components of the assay are packaged together with appropriate instructions in such a way as to facilitate the performance of the assay. This kit could be made available commercially and the performance of the assay (and hence, the kit) among users could be standardized via the laboratory of the supplier of the kit.

Much of the apparatus used by the CA assay described herein comprises equipment normally found in biochemical laboratories. Such items include low-speed refrigerated centrifuges, solvent cupboards, stand-up refrigerators with freezers ($-20°$ C.), pH meters, fume hoods, hot/stir plates, balances, washing- and acid-bath facilities and assorted glassware (e.g., graduated cylinders, erlenmeyer flasks and a variety of bottles). On-line access to vacuum, air and distilled water is assumed. The CA assay requires these items along with certain other, specialized pieces of equipment in order to be performed in any particular laboratory setting.

The purpose of the kit is to make specific recommendations regarding larger items which the CA assay requires, and, to supply the special items required for optimal performance of the assay but not normally readily available. The inclusion of specific instructions for the orchestrated use of this equipment under a variety of applications conditions is assumed.

The recommendations for ancillary equipment required by the CA assay include the following items: a fine balance (that is, capable of measuring grams to at least four decimal places); an ultracold freezer capable of at least $-70°$ C.; an apparatus for creating Type I Reagent Grade Water plus a supply of replacement cartridges and filters including the final membrane filter assembly (this latter micron-filter sandwich must be replaced more frequently than the main cartridges); a dish-washing facility capable of rinsing glassware with distilled water (and preferably with Type I water); a high temperature oven (capable of attaining at least 300° F.); a supply of a noble (or inert) gas (such as nitrogen or helium); a reciprocating utility shaker (capable of 280 excursions per minute) fitted with a suitable carrier attachment capable of accommodating a rack of culture tubes positioned so that the long-axis of the tubes is placed horizontally during the shaking procedure; a small, tank-type ultrasonic cleaner; automatic micropipettes (with graded selections from 1-1000 $\mu L$); glassware (including amber glass storage bottles and repipettes); 12 mL capacity, borosilicate glass culture tubes with teflon-lined screw caps; plastic and glass pasteur pipettes; thermometers capable of reaching $+360°$ C. and $-100°$ C; lint-free tissue (e.g., Kim-Wipes) and cotton gauze sponges (sterile and non-sterile). Additionally, the glass filtration assembly used by the assay requires a bracket to hold the pieces of the assembly in place. A perspex frame, built according to the dimensions of the filtration glassware plus the stir-plate used, is recommended. Similar perspex frames need to be acquired to accommodate any small, solution stock bottles which have repipettes fitted on them.

It is recommended that the laboratory in which the human, plasma CA assay will be carried out be climate-controlled and, preferably, electrically isolated from the building in which it is housed. It is preferred that the laboratory itself be grounded [If this feature has not been accommodated by the architectural design of the building in which the laboratory is housed, this can be accomplished by the use of grounded copper strips along the walls.]; and that the temperature of the room be maintained between 68° and 72° F. with a humidity level of about 30–60%. Furthermore, it is preferred that the laboratory in which the assay will be carried out be dedicated to this analysis technique alone. It is assumed that each piece of electrical equipment involved in the CA assay is plugged into a separate power circuit with shielded wires and is properly grounded (i.e., without the formation of ground loops).

In addition to these biochemical equipment requirements, facilities for physiological monitoring and assessment are required for the performance of CA studies in humans. The most fundamental assessments include the measurement of heart rate and blood pressure. The minimum equipment requirements here are a sphygmomanometer and a stethoscope and/or a small, portable electrocardiograph. Any other physiological parameters which are required by the study must also be assessed and recorded. It is especially important to have facilities which permit this monitoring to occur in a non-threatening environment and which includes facilities for the setting up of intravenous lines and the support of individuals thus equipped. Non-threatening environments are created through a combination of colors and furniture and the mood created by the attitudes of the staff employed there. The insertion of intravenous lines requires trained personnel and suitable equipment (including catheters, tubing, tubing adapters, connections and administration facilities, intravenous fluids, heparin- and heparin-and-saline solutions, gauze sponges, skin tape, bandages, syringes and blood collection tubes, etc.). These requirements are normally satisfied within clinical research facilities.

The actual components of the supplied kit can be described within five main categories: blood collection supplies, small assay supplies, large assay supplies, chemicals and operating instructions. The kit includes multiples of critical components of the assay which must be replaced frequently. Each of these will be considered in turn.

The special blood-collection supplies required by the CA assay include a three-way stopcock adaptation for an intravenous line, sterile physiological saline suitable for intravenous administration, syringes [with and without heparin] (3-, and 10-mL size) for collecting the blood from the i.v. line, siliconized tubes (2-, and 10-mL size) for storing and transferring the blood, and a portable ice bucket (preferably square, with a light-excluding lid and a carrying handle).

The small equipment supplies required by the assay include a set of tools for repairing the HPLC-ECD equipment. These tools comprise a set of Allen keys, a set of small wrenches (including a hex set), a small crescent wrench, two strap wrenches, roundnose pliers, a small screwdriver with a selection of heads, a small rubber-nosed hammer, large and fine scissors, fine forceps and long-nosed hemostats, a micro tube-cutter, and a fine, metal file. It is recommended that a supply of professionally prepared, suitably sized, stainless steel tubing be maintained in the laboratory to be used to replace connecting tubing on the HPLC-ECD apparatus.

Other small equipment supplies required by the assay include the diamond paste and cloth required to polish the working electrode; the guard-column assembly and replacement inserts; the pulse dampeners and in-line filters required by the HPLC-ECD apparatus; the replacement parts for the apparatus (the specific components required are usually identified by the manufacturer of the individual piece of apparatus); insulated wires for making the connections between the apparatus and the power supply and ground sources; fine stainless steel tubing for connecting the parts of the HPLC-ECD apparatus (the ends of the tubing should be cut in a perpendicular fashion and the rough edges removed); the glass filtration assembly and suitable replacement filters; glass micro-syringes with stabilized plungers and replaceable needles, adapted for use in the HPLC-ECD system; an in-line filter and flow monitor (regulators) for the connection to the gas tank housing the gas used to purge the solvent reservoir; and regular, laboratory-type ice buckets.

Large equipment items required by the assay include the components of the HPLC-ECD system itself. These comprise the solvent reservoir, the pump, injector, column, detector and data recording device(s), effluent collection facilities and the large Faraday cage which houses this equipment. It is preferred that an uninterruptable power source be used to power all of the equipment. All modifications possible are made to the apparatus so as to facilitate continued function at a sensitivity level (on the ECD) of 1 nA, or less, F.S.D., that is to reduce sources of fundamental and non-fundamental noise. Such modifications include using 3-pole Butterworth instead of traditional RC low-pass filters in the ECD electronics and using resistors with $\leq 1\%$ tolerance; fitting the working electrode compartment with a stainless steel top; and, fitting the pump with in-line filters and extra pulse dampeners. This is a field of rapidly evolving technology; it must therefore be recommended that as improvements to the underlying materials and components of this equipment become available, they are adopted into the CA assay protocol and equipment.

The chemicals which the CA assay uses should all be of a purity level such that contaminants are limited to $\leq 5$ ppb. These are commercially available as "HPLC-grade" (or, occasionally, "ultra-pure") chemicals. This stipulation applies to all chemical compounds which will be used in the extraction procedure and by the mobile phases as well as chemicals used to clean the glassware (such as the nitric acid) and chemicals used to develop the assay proper (such as the CAs standards used to determine the optimal mobile phase composition).

The chemicals thus designated include the acetic acid which forms the basis of the solution which carries the CAs onto the column; the nitric acid which is used to clean the system; the ammonium and sodium hydroxides which are used by the extraction procedure and the mobile phase; the ammonium chloride; the methanol; the EDTA; the HSA; the octanol; the heptane; the TOABr; the toluene used in the siliconizing solution; the sodium phosphates; and the standard CAs. The use of Type I water cannot be over-emphasized. Additionally, the precision of the standard solutions used to calibrate various pieces of machinery (such as the pH meter) is assumed.

The only special chemicals which are required by the blood collection techniques described herein are the heparin solutions needed for the syringes and the intravenous lines.

It must be borne in mind that the body of this document has been written using human plasma as the model system. As such, this matrix requires minimal pre-treatment prior to having the CAs extracted out of it. If other sources of CAs are used, the pre-treatment methods of the matrix must be evolved in such a way as to remove undesired materials and substances but to preserve the integrity of the CAs. Any extract prepared from other sources and containing CAs must be suitably prepared for extraction and injection into the HPLC-ECD system set at 1 nA F.S.D.. In other words, the pre-treatment (and pre-extraction) techniques employed must not (ultimately) contribute particular or chemical contamination to the HPLC-ECD apparatus and must be compatible with the operation of the apparatus. The purity level of any chemicals involved in this maneuver must adhere to the $\leq 5$ ppb contaminants rule specified above.

All of the critical components of the CA assay supplies are supplied in appropriate containers. This means that chemicals are shipped as required to preserve their integrity (e.g., on ice or in amber glass) and arrive in dated lots. It is assumed that the kit furnishes recommendations for the handling, storage and care of all critical components of the CA assay.

The fifth major constituent of the CA assay kit includes the instructions for the performance of the complete assay. These instructions can be presented in a variety of possible ways including the written (i.e., printed) form and/or on a cassette tape and/or on an electronic (e.g., compact) disk and/or in video form. The pertinent instructions include directions for preparing the glassware; directions for the maintenance and care of all equipment associated with the CA assay as a whole; instructions for the collection and treatment of samples to be analyzed for their CA content; instructions for the extraction of sample matrices; and, instructions for the separation, detection and quantification of CAs and related molecules derived from said matrices. These instructions will also include directions for the obtainment and analysis of CAs and other, related molecules (based on the $\beta$-phenylethylamine nucleus) from a multiplicity of sources other than human plasma and including cerebrospinal fluid, extracellular fluid, urine, physiological tissues and extracts (from vertebrate and invertebrate sources), plant materials or their derivatives and a variety of chemical compounds (including synthetic and natural drugs).

Additionally, instructions are included which describe the establishment and maintenance of the performance characteristics of the CA assay in the individual laboratory: these include the determination of the specificity, efficiency, reliability, variability, reproducibility and sensitivity of the assay protocol. Instructions for the standardization of the assay technique over an extended period of time are also included.

Instructions must also be included which describe strategies for problem-solving the difficulties which arise with the operation of the assay or the apparatus involved in it.

While in accordance with patent statutes, a best mode and preferred embodiment has been set forth, the scope of the present invention is measured by the scope of the attached claims.

What is claimed is:

1. A method for the assaying of low concentrations of an oxidizable or reducible biogenic amine or derivative or metabolite thereof, comprising the steps of:
    (a) preparing a sample of at least one said compound, said sample being suitable for quantitative analysis;
    (b) injecting said sample into a high pressure liquid chromatography apparatus to thereby form a chromatogram, said apparatus including:
        (1) a chromatography column containing a quantity of microparticulate material as a stationary phase;
        (2) a mobile phase passing through said stationary phase, said mobile phase comprising the following components:
            (a) from about 50 mM to about 250 mM of a buffer having a pH of from about 2 to about 8;
            (b) from about 0.1 mM to about 10.0 mM of a chelating agent;
            (c) from about 0.1 mM to about 10.0 mM of an alkyl sulfonate, said alkyl sulfonate having from about 4 to about 14 carbon atoms; and
            (d) from about 0.1% to about 10% by volume methanol in water solution;
        (3) an injector for injecting said sample;
        (4) a pump for pumping said mobile phase through said stationary phase; and
        (5) a guard column positioned upstream of said chromatography column;
    (c) eluting said compounds from said chromatography column;
    (d) passing said eluted compounds through an electrochemical detector cell thereby producing a current output from said detector;
    (e) measuring and integrating the current output from said electrochemical detector to obtain a quantitative analysis of said compound; and
    (f) maintaining a substantially constant base line noise at a sensitivity of said electrochemical detector cell sufficient to measure the quantity of said compound present in resting, human plasma by maintaining all portions of said apparatus contacting said mobile phase and said stationary phase substantially residue-free, wherein the signal to noise ratio of said current output is at least 2 to 1.

2. A method as claimed in claim 1, wherein said compound is natural or synthetic, and is derived from the fluids and tissues of vertebrates, invertebrates or plants.

3. A method as claimed in claim 2 wherein said fluids and tissues comprise blood, cerebrospinal fluid, lymphatic fluid, urine, other extracellular fluids, tissues or tissue extracts.

4. A method as claimed in claim 3, wherein said fluids and tissues are derived from mammals.

5. A method as claimed in claim 4, wherein said mammals are humans.

6. A method as claimed in claim 4, wherein said fluid is plasma.

7. A method as claimed in claim 6, wherein said plasma is human plasma.

8. A method as claimed in claim 7, wherein said human plasma is collected non-traumatically and under aseptic conditions, and wherein said non-traumatic collection procedures include withdrawing a plasma sample via an indwelling catheter inserted into the subject from whom the plasma is being withdrawn at least ten minutes prior to the withdrawal of the sample.

9. A method as claimed in claim 1, wherein said compound is extracted from a source by the steps of binding said compound contained in said source to a carrier thereby forming a carrier complex, extracting the complex from the source, and recovering the compound from the carrier complex.

10. A method as claimed in claim 9, wherein said carrier comprises a boron derivative.

11. A method as claimed in claim 9, wherein said extraction includes forming a polar complex of said compound and said boron derivative in an aqueous medium, combining said complex in an aqueous medium with an organic solution containing a counterion for said complex, thereby forming a substantially non-polar complex miscible in said organic solution, separating said organic solution containing said nonpolar complex from said aqueous medium, and washing said organic solution with an aqueous acid solution to thereby liberate said compound from said non-polar complex and separating said acid solution containing said compound from said organic solution.

12. A method as claimed in claim 11, wherein said boron derivative is diphenylborate ethanolamine, wherein said counterion is tetraoctylammonium bromide, wherein said aqueous medium is ammonium chloride-ammonium hydroxide buffer, wherein said organic solution is a mixture of heptane and octanol, and wherein said acid is acetic acid.

13. A method as claimed in claim 11 wherein said boron derivative, said aqueous medium, said organic solution, said counterion, and said aqueous acid solution are comprised of chemicals and reagents having a level of impurity no greater than about 10 ppm.

14. A method as claimed in claim 9, wherein said extraction method is monitored by the addition of an internal standard to the sample matrix prior to extraction.

15. A method as claimed in claim 14, wherein said internal standard does not interfere with the extraction method, and wherein said internal standard does not adversely affect the integrity of the compounds being extracted, and wherein said internal standard does not interfere with the discrimination of the peaks of interest on the chromatogram.

16. A method as claimed in claim 15, wherein said internal standard comprises a catecholamine-like compound.

17. A method as claimed in claim 16, wherein said compound is deoxyepinephrine.

18. A method as claimed in claim 9, wherein sample preparation equipment used in extracting said compound from said source includes a friction-reducing coating over all surfaces contacting said compound to thereby reduce the level of adherence of said compound to said surfaces.

19. A method as claimed in claim 18, wherein said friction-reducing material comprises a silicone-containing material.

20. A method as claimed in claim 18, wherein said sample preparation equipment is washed with an acid prior to initial utilization of said equipment in said extraction method, followed by rinsing said equipment with water to remove said acid.

21. A method as claimed in claim 20, said sample preparation equipment is utilized in said method to prepare a plurality of samples by the steps of:
 (a) washing said equipment with a substantially residue-free aqueous solution of detergent;
 (b) rinsing said washed equipment with distilled water;
 (c) preparing said sample with said equipment;
 (d) removing said sample from said equipment; and
 (e) repeating said detergent washing step and said distilled water rinsing step prior to contacting said equipment with another said sample.

22. A method as claimed in claim 1, including injecting at least one sample into said apparatus, thereby decreasing the level of sensitivity of said electrochemical cell, said sensitivity being thereby increased to a level higher from said decreased level by passing a solution through said apparatus at a superficial velocity of from about 2 to about 200 cm/min. for a period of from about 1 to 15 hours, said solution comprising said mobile phase, the amount of methanol in said solution being less than the threshold amount necessary for disruption of the reference electrode in said cell, and containing sufficient quantity of an alkyl sulfonate so as to flush fatty acids from the apparatus.

23. A method as claimed in claim 1, wherein said method includes cleaning said high pressure liquid chromatography apparatus which comprises the steps, in sequence, of displacing said mobile phase with a first quantity of water, displacing said water with a first quantity of a methanol/water mixture having from about 30 to about 70 vol. % methanol, displacing said methanol/water mixture with methanol, displacing said methanol with a second quantity of said methanol/water mixture, displacing said second quantity of said methanol/water mixture with a second quantity of said water and displacing said second quantity of water with a fresh quantity of said mobile phase.

24. A method as claimed in claim 23, wherein the purity of said water is at least Type I Reagent Grade Water with a minimum resistivity of 10 M$\Omega$, and wherein said methanol has a level of impurity of no greater than about 10 ppm.

25. A method as claimed in claim 1, wherein said method includes cleaning said high pressure liquid chromatography apparatus by the steps of, in sequence, displacing said mobile phase with a first quantity of water, disconnecting said guard-column, said chromatography column and said detector from the injector and the pump, washing said pump and said injector with a quantity of acid, flushing said acid from said pump and said injector with a quantity of water sufficient to result in a substantially neutral effluent, reconnecting said chromatography column, said guard-column and said detector to said pump and said injector, displacing said water with a first quantity of a methanol/water mixture having from about 30 to about 70 vol. % methanol, displacing said methanol/water mixture with methanol, displacing said methanol with a second quantity of said methanol/water mixture, displacing said second quantity of said methanol/water mixture with a second quantity of said water and displacing said second quantity of water with a fresh quantity of said mobile phase.

26. A method as claimed in claim 25, wherein said acid comprises nitric acid, wherein said water comprises Type I Reagent Grade water with a minimum resistivity of 10 M$\Omega$, and wherein said methanol has a level of impurity no greater than about 10 ppm.

27. A method as claimed in claim 1, wherein said chromatography column comprises a microparticulate bonded silica.

28. A method as claimed in claim 27, wherein said microparticulate bonded silica comprises alkylphenyl groups having from 7 to 12 carbon atoms bonded to silica particles.

29. A method as claimed in claim 28, wherein said silica particles are irregularly-shaped.

30. A method as claimed in claim 29, wherein said irregularly-shaped silica particles are about 10 $\mu$ in size.

31. A method as claimed in claim 28, wherein said alkylphenyl is ethylphenyl.

32. A method as claimed in claim 1, wherein said method further includes filtering said mobile phase, degassing said filtered mobile phase, and purging said degassed mobile phase with an inert gas prior to passing said mobile phase through said stationary phase.

33. A method as claimed in claim 32, wherein said filter comprises a membrane filter having a pore size of at least about 0.22 $\mu$.

34. A method as claimed in claim 32, wherein said inert gas comprises nitrogen or a noble gas.

35. A method as claimed in claim 1, wherein said buffer, said chelating agent, said alkyl sulfonate, said methanol and said water in said mobile phase each have a level of impurity of no greater than about 10 ppm.

36. A method as claimed in claim 1, wherein said buffer is sodium phosphate having a pH of about 4.8, and wherein said sodium phosphate buffer has a concentration of about 70 mM.

37. A method as claimed in claim 1, wherein said chelating agent is a chelator of heavy metal ions.

38. A method as claimed in claim 37, wherein said chelator of heavy metal ions is EDTA, and wherein said EDTA has a concentration of 1 mM.

39. A method as claimed in claim 1, wherein said alkyl sulfonate is heptanesulfonate, and wherein said heptanesulfonate has a concentration of about 5 mM.

40. A method as claimed in claim 1, wherein flow of said mobile phase through said apparatus is pulseless.

41. A method as claimed in claim 1, wherein said apparatus is electrically isolated.

42. A method as claimed in claim 41, wherein said pump, said injector and said detector are grounded.

43. A method as claimed in claim 41, wherein said injector, said column and said detector are contained in a Faraday cage.

44. A method as claimed in claim 1, wherein said electrochemical detector cell includes an electrically conductive cap.

45. A method as claimed in claim 1, wherein said electrochemical detector includes electronic controls which are modified to reduce fundamental and non-fundamental noise, and wherein said reduction of fundamental and non-fundamental noise permits the electrochemical detector to maintain a level of sensitivity sufficient to measure the quantity of adrenaline in resting, human plasma.

46. A method as claimed in claim 45, wherein said level of sensitivity of the electrochemical detector is at least one nanoamp full scale deflection.

47. A method as claimed in claim 1, including the steps of monitoring said signal to noise ratio and maintaining said signal to noise ratio above a pre-determined level by maintaining the functional integrity of the electrodes of the electrochemical detector, said electrodes including a glassy carbon working electrode and a stable (gel-filled) reference electrode.

48. A method as claimed in claim 47, wherein said predetermined level of signal to noise ratio is at least about 2 to 1.

49. A method as claimed in claim 47, wherein said predetermined level of signal to noise ratio is at least about 4 to 1.

50. A method as claimed in claim 47, wherein said predetermined level of signal to noise ratio is at least about 8 to 1.

51. A method as claimed in claim 47, wherein the functional integrity of said glassy carbon working electrode is maintained by polishing the working electrode with a polishing medium or compound having a hardness of at least 9 on the Mohs scale, and wherein said polishing step takes place only when the HPLC-ECD apparatus has substantially pure solvent as the mobile phase.

52. A method as claimed in claim 51, wherein said polishing step includes:
(a) exposing said working electrode to polishing compound in the form of an aqueous phase for a period of time ranging from about 30 seconds to about 2 minutes,
(b) removing said polishing compound by the action of water, and
(c) subjecting the polished electrode to sonication to further remove particles of the polishing compound.

53. A method as claimed in claim 52, wherein steps (a), (b) and (c) of the polishing step are performed sequentially with a polishing compound having polishing fragments of about 6 $\mu$ size and a polishing compound having polishing fragments of about 0.25 $\mu$.

54. A method as claimed in claim 53, wherein said polishing compound comprises natural diamond fragments.

55. A method as claimed in claim 53, wherein said electrode is subjected to said sonication treatment in a solution comprising a mixture of methanol and water, and wherein said methanol has a level of impurity no greater than 10 parts per million, and wherein said water comprises Type I Reagent Grade Water with a minimum resistivity of 10 M$\Omega$.

56. A method as claimed in claim 1, wherein said step of integrating the current output from said electrochemical detector is performed on an integrator having a means for subtracting a baseline noise component produced by said mobile phase.

57. A method for the assaying of low concentrations of an oxidizable or reducible compound comprising the steps of:
(a) preparing a sample of at least one of said compounds, said sample being suitable for quantitative analysis;
(b) injecting said sample into a high pressure liquid chromatography apparatus to thereby form a chromatogram, said apparatus including:
(1) a chromatography column containing a quantity of microparticulate material as a stationary phase;
(2) a mobile phase passing through said stationary phase, said mobile phase comprising the following components:
(a) from about 50 mM to about 250 mM of a buffer having a pH of from about 2 to about 8;
(b) from about 0.1 mM to about 10.0 mM of a chelating agent;
(c) from about 0.1 mM to about 10.0 mM of an alkyl sulfonate, said alkyl sulfonate having from about 4 to about 14 carbon atoms; and
(d) from about 0.1% to about 10% methanol in water solution;
(3) an injector for injecting said sample;

(4) a pump for pumping said mobile phase through said stationary phase; and (5) a guard column positioned upstream of said chromatography column;

(c) eluting said compounds from said chromatography column;

(d) passing said eluted compounds through an electrochemical detector cell thereby producing a current output from said detector;

(e) measuring and integrating the current output from said electrochemical detector to obtain a quantitative analysis of said compound; and (f) maintaining a sensitivity of said electrochemical detector cell at about 1 nanoamp or less full scale deflection by maintaining all portions of said apparatus contacting said mobile phase and said stationary phase substantially residue-free, wherein the signal to noise ratio of said current output is at least about 2 to 1.

58. A method as claimed in claim 57, wherein the signal to noise ratio of said current output is at least about 8 to 1.

59. A method as claimed in claim 1, wherein a plurality of samples are injected sequentially into said high pressure liquid chromatography apparatus and wherein said sensitivity is maintained throughout for assaying of said plurality of samples.

60. A method as claimed in claim 57, wherein a plurality of samples are injected sequentially into said high pressure liquid chromatography apparatus and wherein said sensitivity is maintained throughout for assaying of said plurality of samples.

* * * * *